US011339201B2

(12) United States Patent
Garrett-Thomson et al.

(10) Patent No.: US 11,339,201 B2
(45) Date of Patent: May 24, 2022

(54) VARIANT PD-L1 POLYPEPTIDES, T-CELL MODULATORY MULTIMERIC POLYPEPTIDES, AND METHODS OF USE THEREOF

(71) Applicant: ALBERT EINSTEIN COLLEGE OF MEDICINE, Bronx, NY (US)

(72) Inventors: Sarah C. Garrett-Thomson, New York, NY (US); Steven C. Almo, Pelham, NY (US); Ronald D. Seidel, III, Larchmont, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 16/098,983

(22) PCT Filed: May 17, 2017

(86) PCT No.: PCT/US2017/033042
§ 371 (c)(1),
(2) Date: Nov. 5, 2018

(87) PCT Pub. No.: WO2017/201131
PCT Pub. Date: Nov. 23, 2017

(65) Prior Publication Data

US 2019/0153065 A1 May 23, 2019

Related U.S. Application Data

(60) Provisional application No. 62/338,128, filed on May 18, 2016.

(51) Int. Cl.
*C07K 14/705* (2006.01)
*A61K 9/00* (2006.01)
*C07K 14/74* (2006.01)

(52) U.S. Cl.
CPC ...... *C07K 14/70532* (2013.01); *A61K 9/0019* (2013.01); *C07K 14/70521* (2013.01); *C07K 14/70539* (2013.01); *C07K 2319/20* (2013.01); *C07K 2319/30* (2013.01)

(58) Field of Classification Search
CPC ........ C07K 14/70539; C07K 14/70521; C07K 14/70532
USPC ........................................................ 424/134.1
See application file for complete search history.

(56) References Cited

U.S. PATENT DOCUMENTS

| | | | |
|---|---|---|---|
| 5,635,363 | A | 6/1997 | Altman et al. |
| 6,197,302 | B1 | 3/2001 | Hirsch et al. |
| 6,211,342 | B1 | 4/2001 | Hirsch et al. |
| 6,268,411 | B1 | 7/2001 | Schneck et al. |
| 6,696,304 | B1 | 2/2004 | Davies |
| 7,098,306 | B2 | 8/2006 | Economou et al. |
| 7,186,804 | B2 | 3/2007 | Gillies et al. |
| 7,670,595 | B2 | 3/2010 | Gillies et al. |
| 8,992,937 | B2 | 3/2015 | Hansen et al. |
| 9,284,349 | B2 | 3/2016 | Tsunoda et al. |
| 9,359,424 | B2 | 6/2016 | Le Maoult et al. |
| 9,494,588 | B2 | 11/2016 | Springer et al. |
| 2002/0006664 | A1 | 1/2002 | Sabatini |
| 2002/0031520 | A1 | 3/2002 | Economou et al. |
| 2004/0038349 | A1 | 2/2004 | Hilbert et al. |
| 2004/0161817 | A1 | 8/2004 | Benton et al. |
| 2004/0209363 | A1 | 10/2004 | Watts et al. |
| 2005/0003431 | A1 | 1/2005 | Wucherpfennig et al. |
| 2005/0009012 | A1 | 1/2005 | Holzberg et al. |
| 2005/0100926 | A1 | 5/2005 | Chen et al. |
| 2006/0034865 | A1 | 2/2006 | Hildebrand et al. |
| 2006/0269515 | A1 | 11/2006 | Denis-Mize et al. |
| 2007/0036752 | A1 | 2/2007 | Gillies et al. |
| 2007/0148162 | A1 | 6/2007 | Bhardwaj et al. |
| 2007/0286843 | A1 | 12/2007 | Pfizenmaier et al. |
| 2008/0199485 | A1 | 8/2008 | Kundig et al. |
| 2008/0219947 | A1 | 9/2008 | Linette et al. |
| 2008/0269070 | A1 | 10/2008 | Ramseier et al. |
| 2010/0159594 | A1 | 6/2010 | Hansen et al. |
| 2011/0002956 | A1 | 1/2011 | Weiner et al. |

(Continued)

FOREIGN PATENT DOCUMENTS

| | | | |
|---|---|---|---|
| CN | 1791675 | A | 6/2006 |
| CN | 101418309 | A | 4/2009 |
| CN | 101448951 | A | 6/2009 |
| JP | 2000515363 | A | 11/2000 |
| JP | 2004501364 | A | 1/2004 |
| JP | 2005506058 | A | 3/2005 |
| JP | 2007530021 | A | 11/2007 |
| JP | 2009537175 | A | 10/2009 |
| JP | 2010524506 | A | 7/2010 |
| JP | 2012516854 | A | 7/2012 |
| JP | 2015537043 | A | 12/2015 |

(Continued)

OTHER PUBLICATIONS

Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).

(Continued)

*Primary Examiner* — Yan Xiao
(74) *Attorney, Agent, or Firm* — Fox Rothschild LLP

(57) ABSTRACT

The present disclosure provides variant PD-L1 immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

18 Claims, 25 Drawing Sheets

Specification includes a Sequence Listing.

(56) References Cited

U.S. PATENT DOCUMENTS

| | | | |
|---|---|---|---|
| 2011/0268737 | A1 | 11/2011 | Favier et al. |
| 2011/0318380 | A1 | 12/2011 | Brix et al. |
| 2012/0003220 | A1 | 1/2012 | Chen |
| 2012/0121577 | A1 | 5/2012 | Weidanz et al. |
| 2012/0177595 | A1 | 7/2012 | Wong et al. |
| 2012/0264161 | A1 | 10/2012 | Scholler et al. |
| 2013/0017199 | A1 | 1/2013 | Langermann |
| 2013/0149305 | A1 | 6/2013 | Ostrand-Rosenberg |
| 2014/0046026 | A1 | 2/2014 | Garcia et al. |
| 2014/0162293 | A1 | 6/2014 | Springer et al. |
| 2014/0242077 | A1 | 8/2014 | Choi et al. |
| 2015/0071987 | A1 | 3/2015 | Selvaraj |
| 2015/0224186 | A1 | 8/2015 | Nakagawa |
| 2015/0232532 | A1 | 8/2015 | Ostrand-Rosenberg |
| 2015/0374788 | A1 | 12/2015 | Paulsen et al. |
| 2016/0011204 | A1 | 1/2016 | Almo et al. |
| 2016/0083477 | A1 | 3/2016 | Klein et al. |
| 2016/0090407 | A1 | 3/2016 | Hosse et al. |
| 2016/0114019 | A1 | 4/2016 | Li et al. |
| 2016/0152725 | A1 | 6/2016 | Cheung et al. |
| 2016/0175397 | A1 | 6/2016 | Umana et al. |
| 2016/0304580 | A1 | 10/2016 | Ellmark et al. |
| 2016/0362465 | A1 | 12/2016 | Nishimura et al. |
| 2017/0044229 | A1 | 2/2017 | Garcia et al. |
| 2017/0058015 | A1 | 3/2017 | Seidel et al. |
| 2017/0334951 | A1 | 11/2017 | O'Reilly et al. |
| 2018/0064795 | A1 | 3/2018 | Sugiyama |
| 2018/0208626 | A1 | 7/2018 | Scheinberg et al. |

FOREIGN PATENT DOCUMENTS

| | | | |
|---|---|---|---|
| WO | 97/028191 | A1 | 8/1997 |
| WO | 2001/090747 | A2 | 11/2001 |
| WO | 2002/072631 | A2 | 9/2002 |
| WO | 2002/087613 | A1 | 11/2002 |
| WO | 2002/093129 | A2 | 11/2002 |
| WO | 2002/102299 | A2 | 12/2002 |
| WO | 2004/029197 | A2 | 4/2004 |
| WO | 2004/111190 | A2 | 12/2004 |
| WO | 2007/136778 | A2 | 11/2007 |
| WO | 2008/019888 | A2 | 2/2008 |
| WO | 2008/116468 | A2 | 10/2008 |
| WO | 2008/134461 | A2 | 11/2008 |
| WO | 2010/037395 | A2 | 4/2010 |
| WO | 2010/091122 | A1 | 8/2010 |
| WO | 2011/066342 | A2 | 6/2011 |
| WO | 2011/066389 | A1 | 6/2011 |
| WO | 2012/127464 | A2 | 9/2012 |
| WO | 2012/175508 | A1 | 12/2012 |
| WO | 2013/003761 | A1 | 1/2013 |
| WO | 2014/083004 | A1 | 6/2014 |
| WO | 2014/093118 | A1 | 6/2014 |
| WO | 2015/112541 | A2 | 7/2015 |
| WO | 2015/164815 | A1 | 10/2015 |
| WO | 2015195531 | A1 | 12/2015 |
| WO | 2016/014428 | A2 | 1/2016 |
| WO | 2016000619 | A1 | 1/2016 |
| WO | 2016/025642 | A1 | 2/2016 |
| WO | 2016/029043 | A1 | 2/2016 |
| WO | 2016/030350 | A1 | 3/2016 |
| WO | 2016/164937 | A2 | 10/2016 |
| WO | 2016/168771 | A2 | 10/2016 |
| WO | 2017/023779 | A1 | 2/2017 |
| WO | 2017/059819 | A1 | 4/2017 |
| WO | 2017/151818 | A2 | 9/2017 |
| WO | 2017/151940 | A2 | 9/2017 |
| WO | 2017/201131 | A1 | 11/2017 |
| WO | 2019/051126 | A1 | 3/2019 |

OTHER PUBLICATIONS

Aina, et al.; "Identification of novel targeting peptides for human ovarian cancer cells using 'one-bead one-compount' combinatorial libraries"; Mol. Cancer Ther.; vol. 4, No. 5, 8 pages (May 2005).

Arduin, et al.; "Highly reduced binding to high and low affinity mouse Fc gamma receptors by L234A/L235A and N297A Fc mutations engineered into mouse lgG2a"; Molecular Immunology; vol. 63, pp. 456-463 (2015).

Baldi, et al.; "Recombinant protein production by large-scale transient gene expression in mammalian cells: state of the art and future perspectives"; Biotechnol. Lett.; vol. 29, pp. 677-684 (2007).

Bowers, et al.; "Coupling mammalian cell surface display with somatic hypermutation for the discovery and maturation of human antibodies"; PNAS; vol. 108, No. 51, p. 20455-20460 (Dec. 20, 2011).

Cafri, et al.; "Development of novel genetic cancer vaccines based on membrane-attached ?2 microglobulin"; Ann. N.Y. Acad. Sci.; vol. 1283, pp. 87-90 (2013).

Cebecauer, et al.; "Soluble MHC-Peptide Complexes Induce Rapid Death of CD8+ CTL"; The Journal of Immunology; vol. 174, pp. 6809-6819 (2005).

Center for Disease Control and Prevention; "How Many Cancers are Linked with HPV Each Year?"; 4 pages (2016).

Chames, et al.; "Bispecific antibodies for cancer therapy; The light at the end of the tunnel?" mAbs; vol. 1, No. 6, pp. 539-547 (Nov.-Dec. 2009).

Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).

Crisci, et al.; "Virus-like particles: The new frontier of vaccines for animal viral infections"; Veterinary Immunology and Immunopathology; vol. 148, pp. 211-225 (2012).

Czajkowsky, et al.; "Fc-fusion proteins: new developments and future perspectives"; EMBO Mol. Med.; vol. 4, pp. 1015-1028 (2012).

Das, et al.; "Generation of murine tumor cell lines deficient in MHC molecule surface expression using the CRISPR/Cas9 system"; PLoS One; vol. 12, No. 3, 19 pages (Mar. 16, 2017).

Desmond, et al.; "A systematic review of T-cell epitopes in hepatitis B virus: identification, genotypic variation and relevance to antiviral therapeutics"; Antiviral Therapy; vol. 13, pp. 161-175 (2008).

Dimasi, et al.; "The design and characterization of oligospecific antibodies for simultaneous targeting of multiple disease mediators"; Journal of Molecular Biology; 393(3): p. 672-692 (2009).

Doussal, et al.; "Phage display of peptide /major histocompatibility complex"; Journal of Immunological Methods; vol. 241, pp. 147-158 (2000).

Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).

Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).

Engelhard; "Structure of peptides associated with MHC class I molecules"; Current Opinion in Immunology; vol. 6, pp. 13-23 (1994).

Goel, et al.; "Plasticity within the Antigen-Combining Site May Manifest as Molecufar Mimicry in the Humoral Immune Response"; The Journal of Immunology; vol. 173, pp. 7358-7367 (2004).

Gough, et al.; "The HLA Region and Autoimmune Disease: Associations and Mechanisms of Action"; Current Genomics; vol. 8, pp. 453-465 (2007).

Greten, et al.; "Peptide-?2-microglobulin-MHC fusion molecules bind antigen-specific T cells and can be used for multivalent MHC-lg complexes"; Journal of Immunological Methods; vol. 271, pp. 125-135 (2002).

Grupp, et al.; "Adoptive Cellular Therapy"; Curr Top Microbiol Immunol.; 344: p. 149-172 (2011).

Guo, et al.; "Different length peptides bind to HLA-Aw68 similarly at their ends but bulge out in the middle"; Nature; vol. 360, pp. 364-366 (Nov. 26, 1992).

Hansen, et al.; "Phage display of peptide/major histocompatibility class I complexes"; Eur. J. Immunol.; vol. 31, pp. 32-38 (2001).

(56) References Cited

OTHER PUBLICATIONS

Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).

Hug, et al.; "T-cadherin is a receptor for hexameric and high-molecular-weight forms of Acrp30/adiponectin"; PNAS; vol. 101, No. 28, p. 10308-10313 (Jul. 13, 2004).

Hugues, et al.; "Generation and use of alternative multimers of peptide/MHC complexes"; Journal of Immunological Methods; vol. 268, pp. 83-92 (2002).

Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).

Karaki, et al.; "Is There Still Room for Cancer Vaccines at the Era of Checkpoint Inhibitors"; Vaccines; vol. 4, No. 37, 24 pages (2016).

Khan, et al.; "Adjustable Locks and Flexible Keys: Plasticity of Epitope-Paratope Interactions in Germline Antibodies"; The Journal of Immunology; vol. 192, pp. 5398-5405 (2014).

Kim, et al.; "Single chain MHC I trimer-based DNA vaccines for protection against Listeria monocytogenes infection"; Vaccine; vol. 30, pp. 2178-2186 (2012).

Krautwurst, et al.; "Identification of Ligands for Olfactory Receptors by Functional Expression of a Receptor Library"; Cell; vol. 95, pp. 917-926 (Dec. 23, 1998).

Kushnir, et al.; "Virus-like particles as a highly efficient vaccine platform: Diversity of targets and production systems and advances in clinical development"; Vaccine; vol. 31, pp. 58-83 (2012).

Lenormand, et al.; "HLA-DQA2 and HLA-DQB2 Genes Are Specifically Expressed in Human Langerhans Cells and Encode a New HLA Class II Molecule"; The Journal of Immunology; vol. 199, No. 8, pp. 3903-3911 (Apr. 15, 2012).

Liu, et al.; "Attaining High Transient Titers in CHO Cells"; Genetic Engineering & Biotechnology News; vol. 35, No. 17, 3 pages (Oct. 1, 2015).

Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).

Mallone, et al.; "T Cell Recognition of Autoantigens in Human Type 1 Diabetes: Clinical Perspectives"; Clinical and Developmental Immunology; vol. 2011, 16 pages (2011).

Margalit, et al.; "Induction of Antitumor Immunity by CTL Epitopes Genetically Linked to Membrane-Anchored ?2-Microglobulin"; The Journal of Immunology; vol. 176, pp. 217-224 (2006).

Mcallister, et al.; "Adaptation of Recombinant HEK-293 Cells to Growth in Serum Free Suspension"; Animal Cell Technology: Products from Cells, Cells as Products; 3 pages (1999).

Miao, et al.; "Transient expression of fluorescent fusion proteins in protoplasts of suspension cultured cells"; Nature Protocols; vol. 2, No. 10, pp. 2348-2353 (2007).

Mizukoshi, et al.; "Identification of ?-fetoprotein-derived peptides recognized by cytotoxic T lymphocytes in HLA-A24 + patients with hepatocellular carcinoma"; Int. J Cancer; vol. 118, pp. 1194-1204 (2006).

Mott, et al.; "The Solution Structure of the F42A Mutant of Human Interleukin 2"; J. Mol. Biol.; vol. 247, pp. 979-994 (1995).

Muller, et al.; "Random peptide libraries displayed on adeno-associated virus to select for targeted gene therapy vectors"; Nature Biotechnology; vol. 21, No. 9, pp. 1040-1046 (Sep. 2003).

Naidoo, et al.; "Toxicities of the anti-PD-1 and anti-PD-L1 immune checkpoint antibodies"; Annals of Oncology; vol. 26, pp. 2375-2391 (2015).

Nielsen, et al.; "MHO Class II epitope predictive algorithms"; Immunology; vol. 130, pp. 319-328 (2010).

Oates, et al.; "ImmTACs: Novel bi-specific agents for targeted cancer therapy"; OncoImmunology; vol. 2, No. 2, 3 pages (Feb. 2013).

Obermann, et al.; "Peptide-?2-microglobulin-major histocompatibility complex expressing cells are potent antigen-presenting cells that can generate specific T cells"; Immunology; vol. 122, pp. 90-97 (2007).

Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).

Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, pp. 21181-21187 (1995).

PCT International Search Report and Written Opinion, dated Oct. 10, 2017 in connection with PCT International Application No. PCT/US2017/33042, 17 pages.

Ponstingl, et al.; "The Rule of Antibody Structure: The Primary Structure of a Monoclonal lgG1 Immunoglobulin (Myeloma Protein Nie)"; Hoppe Seylers Z Physiol Chem.; vol. 357, No. 11, pp. 1571-1604 (Nov. 1976). [English translation of Abstract Only].

Poosarla, et al.; "Computational De Novo Design of Antibodies Binding to a Peptide With High Affinity"; Biotechnology & Bioengineering; vol. 114, No. 6, pp. 1331-1342 (Jun. 2017).

Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).

Ramani, et al.; "A secreted protein microarray platform for extracellular protein interaction discovery"; Analytical Biochemistry; vol. 420, pp. 127-138 (2012).

Reche, et al.; "Sequence Variability Analysis of Human Class I and Class II MHC Molecules: Functional and Structural Correlates of Amino Acid Polymorphisms"; Journal of Molecular Biology; vol. 331, No. 3, pp. 623-641 (Aug. 15, 2003).

Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).

Shah, et al.; "Bio-layer Interferometry for Measuring Kinetics of Protein-protein Interactions and Allosteric Ligand Effects"; Journal of Visualized Experiments; vol. 84, 11 pages (2014).

Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).

Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).

Stadinski, et al.; "Diabetogenic T cells recognize insulin bound to lAg7 in an unexpected, weakly binding register"; PNAS; vol. 107, No. 24, pp. 10978-10983 (Jun. 15, 2010).

Taube, et al.; "Lentivirus Display: Stable Expression of Human Antibodies on the Surface of Human Cells and Virus Particles"; PLoS One; vol. 3, No. 9, 12 pages (Sep. 2008).

Torres, et al.; "The immunoglobulin constant region contributes to affinity and specificity"; Trends in Immunology; vol. 29, No. 2, pp. 91-97 (Jan. 10, 2008).

Toukam, et al.; "Targeting Antibody Responses to the Membrane Proximal External Region of the Envelope Glycoprotein of Human Immunodeficiency Virus"; PLoS One; vol. 7, No. 5, 10 pages (May 2012).

Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).

Venkatakrishnan, et al.; "The Structural Biology of Hepatitis B Virus: Form and Function"; Annu. Rev. Virol.; vol. 3, No. 1, pp. 429-451 (Sep. 29, 2016).

(56) References Cited

OTHER PUBLICATIONS

Wen, et al.; "Construction and screening of an antigen-derived peptide library displayed on yeast cell surface for CD4+ T cell epitope identification"; Methods Mol. Biol.; vol. 1061, pp. 245-264 (2013).
Whitehead, et al.; "Optimization of affinity, specificity and function of designed influenza inhibitors using deep sequencing"; Nat. Biotechnol.; vol. 30, No. 6, pp. 543-548 (Apr. 29, 2013).
Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).
Wu, et al.; "Simultaneous targeting of multiple disease mediators by a dual-variable-domain immunoglobulin"; Nature Biotechnology; 25: p. 1290-1297 (2007).
Xu, et al.; "Cytokine release syndrome in cancer immunotherapy with chimeric antigen receptor engineered T cells" Cancer Letters; 343(2): p. 172-178 (2014).
Ziauddin, et al.; "Microarrays of cells expressing defined cDNAs"; Nature; vol. 411, pp. 107-110 (May 3, 2011).
Azuma, et al.; "B7-H1 is a ubiquitous antiapoptotic receptor on cancer cells"; Immunobiology; vol. 111, No. 7, pp. 3635-3643 (Apr. 1, 2008).
Crawford, et al.; "Use of baculovirus MHC/ peptide display libraries to characterize T-cell receptor ligands"; Immunological Reviews; vol. 210, pp. 156-170 (2006).
Wang, et al.; "Using a baculovirus display library to identify MHC class I mimotopes"; PNAS; vol. 102, No. 7, pp. 2476-2481 (Feb. 15, 2005).
GENBANK:AEV43323.1; "Fc IgG1 heavy chain constant region, partial [*Homo sapiens*]"; 2 pages (Jul. 25, 2016).
Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).
Strohl; "Optimization of Fc-mediated effector functions of monoclonal antibodies"; Current Opinion in Biotechnology; vol. 20, pp. 685-691 (2009).
Buonaguro, et al.; "Translating Tumor Antigens into Cancer Vaccines"; Clinical and Vaccine Immunology; vol. 18, No. 1, pp. 23-24 (Jan. 2011).
Carey, et al.; "A soluble divalent class I MHC/lgG1 fusion protein activates CD8+ T cells in vivo"; Clinical Immunology; vol. 116, pp. 65-76 (2005).
Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).
De Charette, et al.; "Turning tumour cells into antigen presenting cells: The next step to improve cancer immunotherapy?"; European Journal of Cancer; vol. 68, pp. 134-147 (2016).
GENEBANK:NP_001009066.1; 2 pages (2003).
HLA Nomenclature; "HLA Alleles Numbers"; 2 pages (Mar. 17, 2015).
Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).
Karin, et al.; "Reversal of Experimental Autoimmune Encephalomyelitis by a Soluble Peptide Variant of a Myelin Basic Protein Epitope: T Cell Receptor Antagonism and Reduction of Interferon? and Tumor Necrosis Factor ? Production"; J. Exp. Med.; vol. 180, pp. 2227-2237 (Dec. 1994).
Lazar-Molnar, et al.; "Crystal structure of the complex between programmed death-1 (PD-1) and its ligand PD-L2"; PNAS; vol. 105, No. 30, pp. 10483-10488 (Jul. 29, 2008).
Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).
Medina, et al.; "PD-1 Pathway Inhibitors: Immuno-Onology Agents for Restoring Anititumor Immune Responses"; Pharmacotherapy; vol. 36, No. 3, pp. 317-334 (2016).
Motz, et al.; "Tumor Endothelium FasL Establishes a Selective Immune Barrier Promoting Tolerance in Tumors"; Nat. Med.; vol. 20, No. 6, pp. 607-615 (Jun. 2014).
Ochoa-Garay, et al.; "The Ability of Peptides to Induce Cytotoxic T Cells In Vitro Does Not Strongly Correlate with Their Affinity for the H-2Ld Molecule: Implications for Vaccine Design and Immunotherapy"; Molecular Immunology; vol. 34, No. 3, pp. 273-281 (1997).
Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).
Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).
Repana, et al.; "The Network of Cancer Genes (NCG): a comprehensive catalogue of known and candidate cancer genes from cancer sequencing screens"; Genome Biology; vol. 20, No. 1, 12 pages (2019).
Rocha-Zavaleta, et al.; "Interleukin-2 (IL-2) receptor-?? signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).
Schmittnaegel, et al.; "A New Class of Bifunctional Major Histocompatibility Class I Antibody Fusion Molecules to Redirect CDS T Cells"; Molecular Cancer Therapeutics; vol. 15, No. 9, pp. 2130-2142 (Sep. 2016).
Schumacher, et al.; "Neoantigens in cancer immunotherapy"; Science; vol. 348, No. 6230, pp. 69-74 (Apr. 2, 2015).
Stamper, et al.; "Crystal structure of the B7-1/CTLA-4 complex that inhibits human immune responses"; Nature; vol. 410, pp. 608-611 (Mar. 29, 2001).
Itham, et al.; "Activation of antigen-specific T cells by artificial cell constructs having immobilized multimeric peptide-class I complexes and recombinant B7-Fc proteins"; Journal of Immunological Methods; vol. 249, pp. 111-119 (2001).
Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).
Wang, et al.; "Molecular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).
White, et al.; "Soluble Class I MHC with ?2-MicroglobulinCovalently Linked Peptides: Specific Binding to a T Cell Hybridoma"; J Immunol; vol. 162, pp. 2671-2676 (1999).
Zheng, et al.; "B7-CTLA4 interaction enhances both production of antitumor cytotoxic T lymphocytes and resistance to tumor challenge"; PNAS; vol. 95, pp. 6284 6289 (May 1998).
Lin, et al.; "The PD-1/PD-L1 complex resembles the antigen-binding Fv domains of antibodies and T cell receptors"; PNAS; vol. 105, No. 8, pp. 3011-3016 (Feb. 2008).

FIG. 2A

*Mus musculus* PD-L1

Amino acids 1-18 = signal

Amino acids 240-260 = transmembrane

```
  1 MRIFAGIIFT ACCHLLRAFT ITAPKDLYVV EYGSNVTMEC RFPVERELDL LALVVYWEKE
 61 DEQVIQFVAG EEDLKPQHSN FRGRASLPKD QLLKGNAALQ ITDVKLQDAG VYCCIISYGG
121 ADYKRITLKV NAPYRKINQR ISVDPATSEH ELICQAEGYP EAEVIWTNSD HQPVSGKRSV
181 TTSRTEGMLL NVTSSLRVNA TANDVFYCTF WRSQPGQNHT AELIIPELPA THPPQNRTHW
241 VLLGSILLFL IVVSTVLLFL RKQVRMLDVE KCGVEDTSSK NRNDTQFEET (SEQ ID NO:71)
```

FIG. 2B

*Homo sapiens* PD-L1

```
  1 mrifavfifm tywhllnaft vtvpkdlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipgni lnvsikiclt
241 lspst(SEQ ID NO:72)
```

FIG. 2C

```
                 10        20        30        40        50        60
Mouse   MRIFAGIIFTACCHLLRAFTITAPKDLYVVEYGSNVTMECRFPVERELDLLALVVYWEKE  60
        MRIFA  IF   HLL AFT+T PKDLYVVEYGSN+T+EC+FPVE++LDL AL+VYWE E
Human   MRIFAVFIFMTYWHLLNAFTVTVPKDLYVVEYGSNMTIECKFPVEKQLDLAALIVYWEME  60

Mouse   DEQVIQFVAGEEDLKPQHSNFRGRASLPKDQLLKGNAALQITDVKLQDAGVYCCIISYGG  120
        D+ +IQFV GEEDLK QHS++R RA L KDQL  GNAALQITDVKLQDAGVY C+ISYGG
Human   DKNIIQFVHGEEDLKVQHSSYRQRARLLKDQLSLGNAALQITDVKLQDAGVYRCMISYGG  120

Mouse   ADYKRITLKVNAPYRKINQRI-SVDPATSEHELICQAEGYPEAEVIWTNSDHQPVSGKRS  179
        ADYKRIT+KVNAPY KINQRI  VDP TSEHEL CQAEGYP+AEVIWT+SDHQ +SGK +
Human   ADYKRITVKVNAPYNKINQRILVVDPVTSEHELTCQAEGYPKAEVIWTSSDHQVLSGKTT  180

Mouse   VTTSRTEGMLLNVTSSLRVNATANDVFYCTFWRSQPGQNHTAELIIPELPATHPPQNR 237 (SEQ ID NO:73)
         T S+ E  L NVTS+LR+N T N++FYCTF R  P +NHTAEL+IP
Human   TTNSKREEKLFNVTSTLRINTTTNEIFYCTFRRLDPEENHTAELVIPGNILNVSIKI- 237 (SEQ ID NO:74)
```

FIG. 2D

```
  1 mrifavfifm tywhllnaft vtvpkalyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipgni lnvsikiclt
241 lspst(SEQ ID NO:46)
```

FIG. 2E

FT VTVPKALYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:47)

FIG. 2F

```
  1 mrifavfifm tywhllnaft vtvpkrlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipgni lnvsikiclt
241 lspst(SEQ ID NO:48)
```

FIG. 2G

FT VTVPKRLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:49)

FIG. 2H 1 mrifavfifm tywhllnaft vtvpkdlyvv eygsnmtiec kfpvekqldl aaldvyweme
61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipgni lnvsikiclt
241 lspst(SEQ ID NO:50)

FIG. 2I

FT VTVPKDLYVV EYGSNMTIEC KFPVEKQLDL AALDVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:51)

FIG. 2J 1 mrifavfifm tywhllnaft vtvpkdlyvv eygsnmtiec kfpvekqldl aalivyweme
61 dkniidfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipgni lnvsikiclt
241 lspst(SEQ ID NO:52)

FIG. 2K

FT VTVPKDLYVV EYGSNMTIEC KFPVEKQLDL AALIVYWEME DKNIIDFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:53)

FIG. 2L

```
  1 mrifavfifm tywhllnaft vtvpkdlyvv eygsnmtiec kfpvekqldl aalivyweme
 61 dkniiqfvhg erdlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreeklfnvtstlrin tttneifyct frrldpeenh taelvipgni lnvsikiclt
241 lspst(SEQ ID NO:54)
```

FIG. 2M

FT VTVPKDLYVV EYGSNMTIEC KFPVEKQLDL AALIVYWEME DKNIIQFVHG ERDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:55)

FIG. 3A

*Mus musculus* PD-1 (SEQ ID NO:56)

1 mwvrqvpwsf twavlqlswq sgwllevpng pwrsltfypa wltvsegana tftcslsnws
61 edlmlnwnrl spsnqtekqa afcnglsqpv qdarfqiiql pnrhdfhmni ldtrrndsgi
121 ylcgaislhp kakieespga elvvterile tstrypspsp kpegrfqgmv igimsalvgi
181 pvllllawal avfcstsmse argagskddt lkeepsaapv psvayeeldf qgrektpelp
241 tacvhteyat ivfteglgas amgrrgsadg lqgprpprhe dghcswpl

FIG. 3B

*Homo sapiens* PD-1 (SEQ ID NO:57)

1 mqipqapwpv vwavlqlgwr pgwfldspdr pwnpptfspa llvvtegdna tftcsfsnts
61 esfvlnwyrm spsnqtdkla afpedrsqpg qdcrfrvtql pngrdfhmsv vrarrndsgt
121 ylcgaislap kaqikeslra elrvterrae vptahpspsp rpagqfqtlv vgvvggllgs
181 lvllvwvlav icsraargti garrtgqplk edpsavpvfs vdygeldfqw rektpeppvp
241 cvpeqteyat ivfpsgmgts sparrgsadg prsaqplrpe dghcswpl

FIG. 3C

*Mus musculus* B7-1 (SEQ ID NO:58)

```
  1 macncqlmqd tpllkfpcpr lillfvllir lsqvssdvde qlsksvkdkv llpcrynsph
 61 edesedriyw qkhdkvvlsv iagklkvwpe yknrtlydnt tysliilglv lsdrgtyscv
121 vqkkergtye vkhlalvkls ikadfstpni tesgnpsadt kritcfasgg fpkprfswle
181 ngrelpgint tisqdpesel ytissqldfn ttrnhtikcl ikygdahvse dftwekpped
241 ppdskntlvl fgagfgavit vvvivviikc fckhrscfrr neasretnns ltfgpeeala
301 eqtvfl
```

FIG. 3D

*Homo sapiens* B7-1 (CD80) (SEQ ID NO:59)

```
  1 mghtrrqgts pskcpylnff qllvlaglsh fcsgvihvtk evkevatlsc ghnvsveela
 61 qtriywqkek kmvltmmsgd mniwpeyknr tifditnnls ivilalrpsd egtyecvvlk
121 yekdafkreh laevtlsvka dfptpsisdf eiptsnirri icstsggfpe phlswlenge
181 elnainttvs qdpetelyav sskldfnmtt nhsfmcliky ghlrvnqtfn wnttkqehfp
241 dnllpswait lisvngifvi ccltycfapr crerrrnerl rresvrpv
```

FIG. 4A

GenBank 3S7G_A
*Homo sapiens* IgG1 Fc (SEQ ID NO:60)
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325) (SEQ ID NO:61)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246) (SEQ ID NO:62)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 4B

GenBank AAA52770
*Homo sapiens* IgD Fc (amino acids 162-383) (SEQ ID NO:63)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank 0308221A
*Homo sapiens* IgM Fc (SEQ ID NO:64)
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 4C

GenBank P01876

*Homo sapiens* IgA Fc (amino acids 120-353) (SEQ ID NO:65)

234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B

*Homo sapiens* IgE Fc (amino acids 6-222) (SEQ ID NO:66)

212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861

*Homo sapiens* IgG4 Fc (amino acids 100-327) (SEQ ID NO:67)

228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 5A

*Homo sapiens*
GenBank NP_001229687
HLA-A
Amino acids 25-365 (SEQ ID NO:68)

```
  1 mavmaprtll lllsgalalt qtwagshsmr yfftsvsrpg rgeprfiavg yvddtqfvrf
 61 dsdaasqkme prapwieqeg peywdqetrn mkahsqtdra nlgtlrgyyn qsedgshtiq
121 imygcdvgpd grflrgyrqd aydgkdyial nedlrswtaa dmaaqitkrk weavhaaeqr
181 rvylegrcvd glrrylengk etlqrtdppk thmthhpisd heatlrcwal gfypaeitlt
241 wqrdgedqtq dtelvetrpa gdgtfqkwaa vvvpsgeeqr ytchvqhegl pkpltlrwel
301 ssqptipivg iiaglvllga vitgavvaav mwrrkssdrk ggsytqaass dsaqgsdvsl
361 tackv
```

FIG. 5B

*Homo sapiens*
GenBank NP_005505
HLA-B
Amino acids 25-362 (SEQ ID NO:69)

```
  1 mlvmaprtvl lllsaalalt etwagshsmr yfytsvsrpg rgeprfisvg yvddtqfvrf
 61 dsdaaspree prapwieqeg peywdrntqi ykaqaqtdre slrnlrgyyn qseagshtlq
121 smygcdvgpd grllrghdqy aydgkdyial nedlrswtaa dtaaqitqrk weaareaeqr
181 raylegecve wlrrylengk dkleradppk thvthhpisd heatlrcwal gfypaeitlt
241 wqrdgedqtq dtelvetrpa gdrtfqkwaa vvvpsgeeqr ytchvqhegl pkpltlrwep
301 ssqstvpivg ivaglavlav vvigavvaav mcrrkssggk ggsysqaacs dsaqgsdvsl
361 ta
```

FIG. 5C

*Homo sapiens*
GenBank NP_001229971
HLA-C
Amino acids 25-366 (SEQ ID NO:70)

1 mrvmaprall lllsgglalt etwacshsmr yfdtavsrpg rgeprfisvg yvddtqfvrf
61 dsdaasprge prapwveqeg peywdretqn ykrqaqadrv slrnlrgyyn qsedgshtlq
121 rmygcdlgpd grllrgydqs aydgkdyial nedlrswtaa dtaaqitqrk leaaraaeql
181 raylegtcve wlrrylengk etlqraeppk thvthhplsd heatlrcwal gfypaeitlt
241 wqrdgedqtq dtelvetrpa gdgtfqkwaa vvvpsgqeqr ytchmqhegl qepltlswep
301 ssqptipimg ivaglavlvv lavlgavvta mmcrrkssgg kggscsqaac snsaqgsdes
361 litcka

FIG. 6

```
NP_004039.1      MSRSVALAVLALLSLSGLEAIQRTPKIQVYSRHPAENGKSNFLNCYVSGFHPSDIEVDLL 60
NP_001009066.1   MSRSVALAVLALLSLSGLEAIQRTPKIQVYSRHPAENGKSNFLNCYVSGFHPSDIEVDLL 60
NP_001040602.1   MSRSVALAVLALLSLSGLEAIQRTPKIQVYSRHPPENGKPNFLNCYVSGFHPSDIEVDLL 60
NP_776318.1      MARFVALVLLGLLSLSGLDAIQRPPKIQVYSRHPPEDGKPNYLNCYVYGFHPPQIEIDLL 60
NP_033865.2      MARSVTLVFLVLVSLTGLYAIQKTPQIQVYSRHPPENGKPNILNCYVTQFHPPHIEIQML 60
                 *:* *:*..* *:**:** ***: *:******** *:** * *****  *** .**:.:*

NP_004039.1      KNGERIEKVEHSDLSFSKDWSFYLLYYTEFTPTEKDEYACRVNHVTLSQPKIVKWDRDM 119
NP_001009066.1   KNGERIEKVEHSDLSFSKDWSFYLLYYTEFTPTEKDEYACRVNHVTLSQPKIVKWDRDM 119
NP_001040602.1   KNGEKMGKVEHSDLSFSKDWSFYLLYYTEFTPNEKDEYACRVNHVTLSGPRTVKWDRDM 119
NP_776318.1      KNGEKI-KSEQSDLSFSKDWSFYLLSHAEFTPNSKDQYSCRVKHVTLEQPRIVKWDRDL 118
NP_033865.2      KNGKKIPKVEMSDMSFSKDWSFYILAHTEFTPTETDTYACRVKHASMAEPKTVYWDRDM 119
                 ***::: * * **:******** ***:* ..****...* *:***.*..:. *: * ****:
```

| | PD-1 | | B7-1 | |
|---|---|---|---|---|
| | EC50 (nM) | Bmax | EC50 (nM) | Bmax |
| Wildtype | 1.8 ± 0.5 | 96.7 ± 6.1 | 39.2 ± 14.6 | 68.2 ± 6.4 |
| D28R | 2.6 ± 0.7 | 93.4 ± 6.0 | 18.8 ± 5.4 | 73.1 ± 5.0 |
| D49R | 1.8 ± 0.4 | 93.6 ± 4.6 | * | * |
| Y56A | 1.9 ± 0.3 | 90.6 ± 3.4 | * | * |
| G119D | 2.0 ± 0.3 | 90.8 ± 3.3 | * | * |
| G120D | 2.5 ± 0.4 | 85.1 ± 3.5 | * | * |
| D122A | * | * | 68.2 ± 18.8 | 54.8 ± 4.5 |
| Y123R | * | * | 7.7 ± 1.6 | 54.8 ± 2.6 |
| K124A | 42.9 ± 13.6 | 64.5 ± 8.4 | 54.9 ± 14.5 | 71.2 ± 5.4 |
| R125A | 38.8 ± 15.0 | 65.1 ± 10.0 | 20.2 ± 5.4 | 60.0 ± 3.8 |

FIG. 10

| | PD-1 | B7-1 |
|---|---|---|
| WT | + | + |
| mCherry | - | - |
| D49A | + | + |
| D49R | + | R |
| **L53R** | - | - |
| V54D | R | R |
| V54A | + | + |
| ***Y56A*** | + | - |
| ***Y56D*** | + | - |
| Q66A | + | + |
| ***Q66D*** | + | R |
| E72A | + | + |
| ***E72R*** | + | - |
| ***G119D*** | + | - |
| **G119R** | - | - |
| ***G120D*** | + | - |
| **A121R** | - | - |
| *D122A* | - | + |
| *Y123A* | - | + |
| *Y123R* | - | + |
| *K124A* | - | + |
| *K124D* | - | + |
| *R125A* | R | + |
| *R125D* | - | + |

FIG. 11

| | PD-1 | B7-1 |
|---|---|---|
| WT | 1.00 | 1.00 |
| mCherry | 0.02 ± 0.02 | 0.10 ± 0.06 |
| *D26A* | 0.54 ± 0.26 | 0.93 ± 0.03 |
| *D26R* | 0.42 ± 0.07 | 0.96 ± 0.06 |
| T37A | 0.31 ± 0.03 | 0.26 ± 0.04 |
| T37R | 0.22 ± 0.11 | 0.17 ± 0.07 |
| ***D49R*** | 0.86 ± 0.06 | 0.31 ± 0.06 |
| L53D | 0.16 ± 0.10 | 0.09 ± 0.04 |
| L53R | 0.14 ± 0.10 | 0.10 ± 0.05 |
| ***V54D*** | 0.88 ± 0.12 | 0.30 ± 0.04 |
| ***V54R*** | 0.95 ± 0.04 | 0.49 ± 0.07 |
| ***Y56A*** | 1.07 ± 0.16 | 0.08 ± 0.04 |
| ***Y56D*** | 0.77 ± 0.10 | 0.07 ± 0.03 |
| ***Y56R*** | 0.64 ± 0.13 | 0.11 ± 0.06 |
| ***Q66D*** | 1.05 ± 0.07 | 0.54 ± 0.06 |
| E72D | 0.55 ± 0.07 | 0.56 ± 0.10 |
| ***E72R*** | 0.48 ± 0.15 | 0.11 ± 0.05 |
| 11150 | 0.02 ± 0.01 | 0.05 ± 0.03 |
| 1116R | 0.01 ± 0.01 | 0.01 ± 0.01 |
| ***G119D*** | 1.40 ± 0.20 | 0.08 ± 0.04 |
| G119R | 0.29 ± 0.10 | 0.02 ± 0.01 |
| G120A | 0.02 ± 0.01 | 0.01 ± 0.01 |
| ***G120D*** | 0.84 ± 0.20 | 0.05 ± 0.04 |
| G120R | 0.05 ± 0.03 | 0.04 ± 0.04 |
| A121D | 0.03 ± 0.03 | 0.03 ± 0.03 |
| A121R | 0.03 ± 0.03 | 0.03 ± 0.03 |
| *D122A* | 0.01 ± 0.01 | 0.74 ± 0.12 |
| D122R | 0.01 ± 0.01 | 0.01 ± 0.01 |
| *Y123A* | 0.01 ± 0.01 | 0.65 ± 0.08 |
| Y123D | 0.01 ± 0.01 | 0.33 ± 0.16 |
| *Y123R* | 0.01 ± 0.01 | 1.12 ± 0.04 |
| *K124A* | 0.02 ± 0.01 | 0.94 ± 0.06 |
| *K124D* | 0.03 ± 0.01 | 0.48 ± 0.05 |
| *K124R* | 0.02 ± 0.01 | 0.85 ± 0.08 |
| *R125A* | 0.03 ± 0.04 | 1.03 ± 0.02 |
| *R125D* | 0.02 ± 0.01 | 1.12±0.08 |

FIG. 12
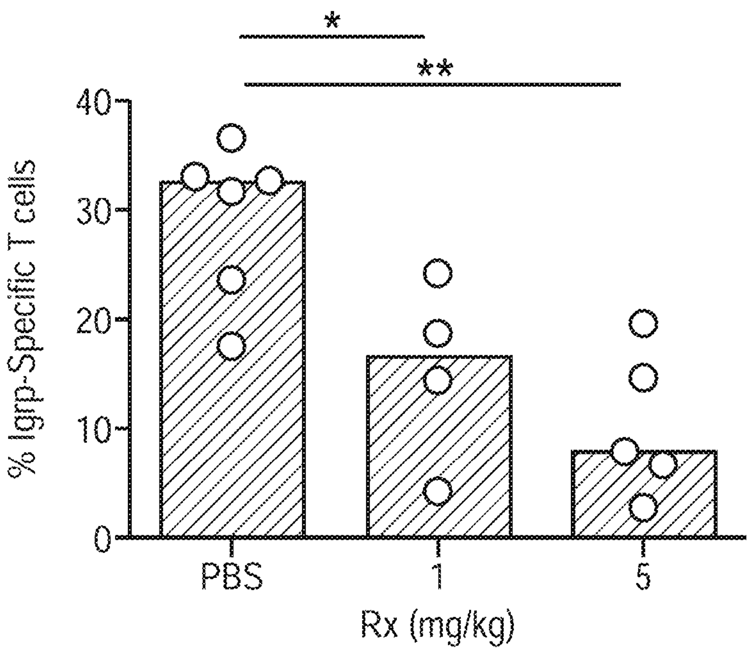
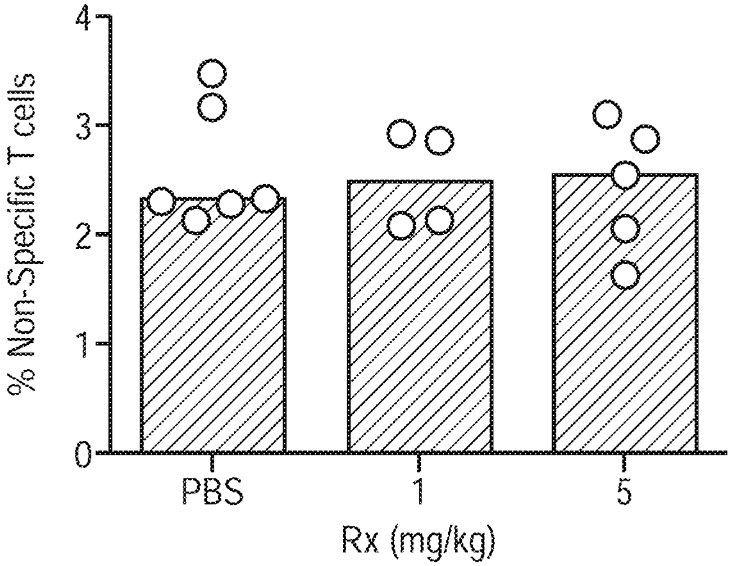

SEQUENCE LISTING

<160> NUMBER OF SEQ ID NOS: 74

<210> SEQ ID NO 1
<211> LENGTH: 219
<212> TYPE: PRT
<213> ORGANISM: Mus musculus

<400> SEQUENCE: 1

Phe Thr Ile Thr Ala Pro Lys Asp Leu Tyr Val Val Glu Tyr Gly Ser
1 5 10 15

Asn Val Thr Met Glu Cys Arg Phe Pro Val Glu Arg Glu Leu Asp Leu
20 25 30

Leu Ala Leu Val Val Tyr Trp Glu Lys Glu Asp Glu Gln Val Ile Gln
35 40 45

Phe Val Ala Gly Glu Glu Asp Leu Lys Pro Gln His Ser Asn Phe Arg
50 55 60

Gly Arg Ala Ser Leu Pro Lys Asp Gln Leu Leu Lys Gly Asn Ala Ala
65 70 75 80

Leu Gln Ile Thr Asp Val Lys Leu Gln Asp Ala Gly Val Tyr Cys Cys
85 90 95

Ile Ile Ser Tyr Gly Gly Ala Asp Tyr Lys Arg Ile Thr Leu Lys Val
100 105 110

Asn Ala Pro Tyr Arg Lys Ile Asn Gln Arg Ile Ser Val Asp Pro Ala
115 120 125

Thr Ser Glu His Glu Leu Ile Cys Gln Ala Glu Gly Tyr Pro Glu Ala
130 135 140

Glu Val Ile Trp Thr Asn Ser Asp His Gln Pro Val Ser Gly Lys Arg
145 150 155 160

Ser Val Thr Thr Ser Arg Thr Glu Gly Met Leu Leu Asn Val Thr Ser
165 170 175

Ser Leu Arg Val Asn Ala Thr Ala Asn Asp Val Phe Tyr Cys Thr Phe
180 185 190

Trp Arg Ser Gln Pro Gly Gln Asn His Thr Ala Glu Leu Ile Ile Pro
195 200 205

Glu Leu Pro Ala Thr His Pro Pro Gln Asn Arg
210 215

<210> SEQ ID NO 2
<211> LENGTH: 219
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

```
Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Gly Asn Ile Leu Asn Val Ser Ile Lys Ile
    210                 215


<210> SEQ ID NO 3
<211> LENGTH: 119
<212> TYPE: PRT
<213> ORGANISM: Homo sapiens

<400> SEQUENCE: 3

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115


<210> SEQ ID NO 4
<211> LENGTH: 119
<212> TYPE: PRT
<213> ORGANISM: Pan troglodytes

<400> SEQUENCE: 4

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30
```

His Pro Ala Glu Asn Gly Lys Ser Asn Phe Leu Asn Cys Tyr Val Ser
35 40 45

Gly Phe His Pro Ser Asp Ile Glu Val Asp Leu Leu Lys Asn Gly Glu
50 55 60

Arg Ile Glu Lys Val Glu His Ser Asp Leu Ser Phe Ser Lys Asp Trp
65 70 75 80

Ser Phe Tyr Leu Leu Tyr Tyr Thr Glu Phe Thr Pro Thr Glu Lys Asp
85 90 95

Glu Tyr Ala Cys Arg Val Asn His Val Thr Leu Ser Gln Pro Lys Ile
100 105 110

Val Lys Trp Asp Arg Asp Met
115

<210> SEQ ID NO 5
<211> LENGTH: 119
<212> TYPE: PRT
<213> ORGANISM: Macaca mulatta

<400> SEQUENCE: 5

Met Ser Arg Ser Val Ala Leu Ala Val Leu Ala Leu Leu Ser Leu Ser
1 5 10 15

Gly Leu Glu Ala Ile Gln Arg Thr Pro Lys Ile Gln Val Tyr Ser Arg
20 25 30

His Pro Pro Glu Asn Gly Lys Pro Asn Phe Leu Asn Cys Tyr Val Ser
35 40 45

Gly Phe His Pro Ser Asp Ile Glu Val Asp Leu Leu Lys Asn Gly Glu
50 55 60

Lys Met Gly Lys Val Glu His Ser Asp Leu Ser Phe Ser Lys Asp Trp
65 70 75 80

Ser Phe Tyr Leu Leu Tyr Tyr Thr Glu Phe Thr Pro Asn Glu Lys Asp
85 90 95

Glu Tyr Ala Cys Arg Val Asn His Val Thr Leu Ser Gly Pro Arg Thr
100 105 110

Val Lys Trp Asp Arg Asp Met
115

<210> SEQ ID NO 6
<211> LENGTH: 118
<212> TYPE: PRT
<213> ORGANISM: Bos taurus

<400> SEQUENCE: 6

Met Ala Arg Phe Val Ala Leu Val Leu Leu Gly Leu Leu Ser Leu Ser
1 5 10 15

Gly Leu Asp Ala Ile Gln Arg Pro Pro Lys Ile Gln Val Tyr Ser Arg
20 25 30

His Pro Pro Glu Asp Gly Lys Pro Asn Tyr Leu Asn Cys Tyr Val Tyr
35 40 45

Gly Phe His Pro Pro Gln Ile Glu Ile Asp Leu Leu Lys Asn Gly Glu
50 55 60

Lys Ile Lys Ser Glu Gln Ser Asp Leu Ser Phe Ser Lys Asp Trp Ser
65 70 75 80

Phe Tyr Leu Leu Ser His Ala Glu Phe Thr Pro Asn Ser Lys Asp Gln
85 90 95

```
Tyr Ser Cys Arg Val Lys His Val Thr Leu Glu Gln Pro Arg Ile Val
            100                 105                 110

Lys Trp Asp Arg Asp Leu
        115


<210> SEQ ID NO 7
<211> LENGTH: 119
<212> TYPE: PRT
<213> ORGANISM: Mus musculus

<400> SEQUENCE: 7

Met Ala Arg Ser Val Thr Leu Val Phe Leu Val Leu Val Ser Leu Thr
1               5                   10                  15

Gly Leu Tyr Ala Ile Gln Lys Thr Pro Gln Ile Gln Val Tyr Ser Arg
            20                  25                  30

His Pro Pro Glu Asn Gly Lys Pro Asn Ile Leu Asn Cys Tyr Val Thr
        35                  40                  45

Gln Phe His Pro Pro His Ile Glu Ile Gln Met Leu Lys Asn Gly Lys
    50                  55                  60

Lys Ile Pro Lys Val Glu Met Ser Asp Met Ser Phe Ser Lys Asp Trp
65                  70                  75                  80

Ser Phe Tyr Ile Leu Ala His Thr Glu Phe Thr Pro Thr Glu Thr Asp
                85                  90                  95

Thr Tyr Ala Cys Arg Val Lys His Ala Ser Met Ala Glu Pro Lys Thr
            100                 105                 110

Val Tyr Trp Asp Arg Asp Met
        115


<210> SEQ ID NO 8
<211> LENGTH: 5
<212> TYPE: PRT
<213> ORGANISM: Artificial sequence
<220> FEATURE:
<223> OTHER INFORMATION: Synthetic Sequence
<220> FEATURE:
<221> NAME/KEY: MISC_feature
<222> LOCATION: (1)..(5)
<223> OTHER INFORMATION: This stretch of residues may be repeated.

<400> SEQUENCE: 8

Gly Ser Gly Gly Ser
1               5


<210> SEQ ID NO 9
<211> LENGTH: 4
<212> TYPE: PRT
<213> ORGANISM: Artificial sequence
<220> FEATURE:
<223> OTHER INFORMATION: Synthetic Sequence
<220> FEATURE:
<221> NAME/KEY: Misc_feature
<222> LOCATION: (1)..(4)
<223> OTHER INFORMATION: This stretch of residues may be repeated.

<400> SEQUENCE: 9

Gly Gly Gly Ser
1


<210> SEQ ID NO 10
<211> LENGTH: 4
<212> TYPE: PRT
<213> ORGANISM: Artificial sequence
<220> FEATURE:
<223> OTHER INFORMATION: Synthetic Sequence
```

-continued

<400> SEQUENCE: 10

Gly Gly Ser Gly
1

<210> SEQ ID NO 11
<211> LENGTH: 5
<212> TYPE: PRT
<213> ORGANISM: Artificial sequence
<220> FEATURE:
<223> OTHER INFORMATION: Synthetic Sequence

<400> SEQUENCE: 11

Gly Gly Ser Gly Gly
1 5

<210> SEQ ID NO 12
<211> LENGTH: 5
<212> TYPE: PRT
<213> ORGANISM: Artificial sequence
<220> FEATURE:
<223> OTHER INFORMATION: Synthetic Sequence

<400> SEQUENCE: 12

Gly Ser Gly Ser Gly
1 5

<210> SEQ ID NO 13
<211> LENGTH: 5
<212> TYPE: PRT
<213> ORGANISM: Artificial sequence
<220> FEATURE:
<223> OTHER INFORMATION: Synthetic Sequence

<400> SEQUENCE: 13

Gly Ser Gly Gly Gly
1 5

<210> SEQ ID NO 14
<211> LENGTH: 5
<212> TYPE: PRT
<213> ORGANISM: Artificial sequence
<220> FEATURE:
<223> OTHER INFORMATION: Synthetic Sequence

<400> SEQUENCE: 14

Gly Gly Gly Ser Gly
1 5

<210> SEQ ID NO 15
<211> LENGTH: 5
<212> TYPE: PRT
<213> ORGANISM: Artificial sequence
<220> FEATURE:
<223> OTHER INFORMATION: Synthetic Sequence

<400> SEQUENCE: 15

Gly Ser Ser Ser Gly
1 5

<210> SEQ ID NO 16
<211> LENGTH: 15
<212> TYPE: PRT
<213> ORGANISM: Artificial sequence
<220> FEATURE:
<223> OTHER INFORMATION: Synthetic Sequence

<400> SEQUENCE: 16

Gly Cys Gly Ala Ser Gly Gly Gly Gly Ser Gly Gly Gly Gly Ser
1 5 10 15

<210> SEQ ID NO 17
<211> LENGTH: 276
<212> TYPE: PRT
<213> ORGANISM: Homo sapiens

<400> SEQUENCE: 17

Gly Ser His Ser Met Arg Tyr Phe Phe Thr Ser Val Ser Arg Pro Gly
1 5 10 15

Arg Gly Glu Pro Arg Phe Ile Ala Val Gly Tyr Val Asp Asp Thr Gln
20 25 30

Phe Val Arg Phe Asp Ser Asp Ala Ala Ser Gln Arg Met Glu Pro Arg
35 40 45

Ala Pro Trp Ile Glu Gln Glu Gly Pro Glu Tyr Trp Asp Gly Glu Thr
50 55 60

Arg Lys Val Lys Ala His Ser Gln Thr His Arg Val Asp Leu Gly Thr
65 70 75 80

Leu Arg Gly Tyr Tyr Asn Gln Ser Glu Ala Gly Ser His Thr Val Gln
85 90 95

Arg Met Tyr Gly Cys Asp Val Gly Ser Asp Trp Arg Phe Leu Arg Gly
100 105 110

Tyr His Gln Tyr Ala Tyr Asp Gly Lys Asp Tyr Ile Ala Leu Lys Glu
115 120 125

Asp Leu Arg Ser Trp Thr Ala Ala Asp Met Ala Ala Gln Thr Thr Lys
130 135 140

His Lys Trp Glu Ala Ala His Val Ala Glu Gln Leu Arg Ala Tyr Leu
145 150 155 160

Glu Gly Thr Cys Val Glu Trp Leu Arg Arg Tyr Leu Glu Asn Gly Lys
165 170 175

Glu Thr Leu Gln Arg Thr Asp Ala Pro Lys Thr His Met Thr His His
180 185 190

Ala Val Ser Asp His Glu Ala Thr Leu Arg Cys Trp Ala Leu Ser Phe
195 200 205

Tyr Pro Ala Glu Ile Thr Leu Thr Trp Gln Arg Asp Gly Glu Asp Gln
210 215 220

Thr Gln Asp Thr Glu Leu Val Glu Thr Arg Pro Ala Gly Asp Gly Thr
225 230 235 240

Phe Gln Lys Trp Ala Ala Val Val Val Pro Ser Gly Gln Glu Gln Arg
245 250 255

Tyr Thr Cys His Val Gln His Glu Gly Leu Pro Lys Pro Leu Thr Leu
260 265 270

Arg Trp Glu Pro
275

<210> SEQ ID NO 18
<211> LENGTH: 274
<212> TYPE: PRT
<213> ORGANISM: Artificial sequence
<220> FEATURE:
<223> OTHER INFORMATION: Synthetic Sequence

<400> SEQUENCE: 18

Gly Pro His Ser Leu Arg Tyr Phe Val Thr Ala Val Ser Arg Pro Gly
1 5 10 15

Leu Gly Glu Pro Arg Phe Ile Ala Val Gly Tyr Val Asp Asp Thr Gln
20 25 30

Phe Val Arg Phe Asp Ser Asp Ala Asp Asn Pro Arg Phe Glu Pro Arg
35 40 45

Ala Pro Trp Met Glu Gln Glu Gly Pro Glu Tyr Trp Glu Glu Gln Thr
50 55 60

Gln Arg Ala Lys Ser Asp Glu Gln Trp Phe Arg Val Ser Leu Arg Thr
65 70 75 80

Ala Gln Arg Tyr Tyr Asn Gln Ser Lys Gly Gly Ser His Thr Phe Gln
85 90 95

Arg Met Phe Gly Cys Asp Val Gly Ser Asp Trp Arg Leu Leu Arg Gly
100 105 110

Tyr Gln Gln Phe Ala Tyr Asp Gly Arg Asp Tyr Ile Ala Leu Asn Glu
115 120 125

Asp Leu Lys Thr Trp Thr Ala Ala Asp Thr Ala Ala Leu Ile Thr Arg
130 135 140

Arg Lys Trp Glu Gln Ala Gly Asp Ala Glu Tyr Tyr Arg Ala Tyr Leu
145 150 155 160

Glu Gly Glu Cys Val Glu Trp Leu Arg Arg Tyr Leu Glu Leu Gly Asn
165 170 175

Glu Thr Leu Leu Arg Thr Asp Ser Pro Lys Ala His Val Thr Tyr His
180 185 190

Pro Arg Ser Gln Val Asp Val Thr Leu Arg Cys Trp Ala Leu Gly Phe
195 200 205

Tyr Pro Ala Asp Ile Thr Leu Thr Trp Gln Leu Asn Gly Glu Asp Leu
210 215 220

Thr Gln Asp Met Glu Leu Val Glu Thr Arg Pro Ala Gly Asp Gly Thr
225 230 235 240

Phe Gln Lys Trp Ala Ala Val Val Val Pro Leu Gly Lys Glu Gln Asn
245 250 255

Tyr Thr Cys His Val His His Lys Gly Leu Pro Glu Pro Leu Thr Leu
260 265 270

Arg Trp

<210> SEQ ID NO 19
<211> LENGTH: 276
<212> TYPE: PRT
<213> ORGANISM: Artificial sequence
<220> FEATURE:
<223> OTHER INFORMATION: Synthetic Sequence

<400> SEQUENCE: 19

Gly Ser His Ser Met Arg Tyr Phe Phe Thr Ser Val Ser Arg Pro Gly
1 5 10 15

Arg Gly Glu Pro Arg Phe Ile Ala Val Gly Tyr Val Asp Asp Thr Gln
20 25 30

Phe Val Arg Phe Asp Ser Asp Ala Ala Ser Gln Arg Met Glu Pro Arg
35 40 45

Ala Pro Trp Ile Glu Gln Glu Gly Pro Glu Tyr Trp Asp Gly Glu Thr
50 55 60

Arg Lys Val Lys Ala His Ser Gln Thr His Arg Val Asp Leu Gly Thr
65 70 75 80

```
Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 20
<211> LENGTH: 276
<212> TYPE: PRT
<213> ORGANISM: Artificial sequence
<220> FEATURE:
<223> OTHER INFORMATION: Synthetic Sequence

<400> SEQUENCE: 20

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160
```

```
Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 21
<211> LENGTH: 276
<212> TYPE: PRT
<213> ORGANISM: Artificial sequence
<220> FEATURE:
<223> OTHER INFORMATION: Synthetic Sequence

<400> SEQUENCE: 21

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240
```

-continued

```
Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 22
<211> LENGTH: 9
<212> TYPE: PRT
<213> ORGANISM: Artificial sequence
<220> FEATURE:
<223> OTHER INFORMATION: Synthetic Sequence

<400> SEQUENCE: 22

Tyr Pro Tyr Asp Val Pro Asp Tyr Ala
1               5


<210> SEQ ID NO 23
<211> LENGTH: 8
<212> TYPE: PRT
<213> ORGANISM: Artificial sequence
<220> FEATURE:
<223> OTHER INFORMATION: Synthetic Sequence

<400> SEQUENCE: 23

Asp Tyr Lys Asp Asp Asp Asp Lys
1               5


<210> SEQ ID NO 24
<211> LENGTH: 10
<212> TYPE: PRT
<213> ORGANISM: Artificial sequence
<220> FEATURE:
<223> OTHER INFORMATION: Synthetic Sequence

<400> SEQUENCE: 24

Glu Gln Lys Leu Ile Ser Glu Glu Asp Leu
1               5                   10


<210> SEQ ID NO 25
<211> LENGTH: 5
<212> TYPE: PRT
<213> ORGANISM: Artificial sequence
<220> FEATURE:
<223> OTHER INFORMATION: Synthetic Sequence

<400> SEQUENCE: 25

His His His His His
1               5


<210> SEQ ID NO 26
<211> LENGTH: 6
<212> TYPE: PRT
<213> ORGANISM: Artificial sequence
<220> FEATURE:
<223> OTHER INFORMATION: Synthetic Sequence

<400> SEQUENCE: 26

His His His His His His
1               5


<210> SEQ ID NO 27
<211> LENGTH: 10
<212> TYPE: PRT
<213> ORGANISM: Artificial sequence
```

-continued

<220> FEATURE:
<223> OTHER INFORMATION: Synthetic Sequence

<400> SEQUENCE: 27

Glu Gln Lys Leu Ile Ser Glu Glu Asp Leu
1               5                   10

<210> SEQ ID NO 28
<211> LENGTH: 8
<212> TYPE: PRT
<213> ORGANISM: Artificial sequence
<220> FEATURE:
<223> OTHER INFORMATION: Synthetic Sequence

<400> SEQUENCE: 28

Asp Tyr Lys Asp Asp Asp Asp Lys
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic Sequence

<400> SEQUENCE: 29

Trp Ser His Pro Gln Phe Glu Lys
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic Sequence

<400> SEQUENCE: 30

Tyr Pro Tyr Asp Val Pro Asp Tyr Ala
1               5

<210> SEQ ID NO 31
<211> LENGTH: 5
<212> TYPE: PRT
<213> ORGANISM: Artificial sequence
<220> FEATURE:
<223> OTHER INFORMATION: Synthetic Sequence

<400> SEQUENCE: 31

Arg Tyr Ile Arg Ser
1               5

<210> SEQ ID NO 32
<211> LENGTH: 4
<212> TYPE: PRT
<213> ORGANISM: Artificial sequence
<220> FEATURE:
<223> OTHER INFORMATION: Synthetic Sequence

<400> SEQUENCE: 32

Phe His His Thr
1

<210> SEQ ID NO 33
<211> LENGTH: 17
<212> TYPE: PRT
<213> ORGANISM: Artificial sequence
<220> FEATURE:
<223> OTHER INFORMATION: Synthetic Sequence

<400> SEQUENCE: 33

Trp Glu Ala Ala Ala Arg Glu Ala Cys Cys Arg Glu Cys Cys Ala Arg
1 5 10 15

Ala

<210> SEQ ID NO 34
<211> LENGTH: 8
<212> TYPE: PRT
<213> ORGANISM: Artificial sequence
<220> FEATURE:
<223> OTHER INFORMATION: Synthetic Sequence

<400> SEQUENCE: 34

Leu Glu Val Leu Phe Gln Gly Pro
1 5

<210> SEQ ID NO 35
<211> LENGTH: 7
<212> TYPE: PRT
<213> ORGANISM: Artificial sequence
<220> FEATURE:
<223> OTHER INFORMATION: Synthetic Sequence

<400> SEQUENCE: 35

Glu Asn Leu Tyr Thr Gln Ser
1 5

<210> SEQ ID NO 36
<211> LENGTH: 5
<212> TYPE: PRT
<213> ORGANISM: Artificial sequence
<220> FEATURE:
<223> OTHER INFORMATION: Synthetic Sequence

<400> SEQUENCE: 36

Asp Asp Asp Asp Lys
1 5

<210> SEQ ID NO 37
<211> LENGTH: 4
<212> TYPE: PRT
<213> ORGANISM: Artificial sequence
<220> FEATURE:
<223> OTHER INFORMATION: Synthetic Sequence

<400> SEQUENCE: 37

Leu Val Pro Arg
1

<210> SEQ ID NO 38
<211> LENGTH: 22
<212> TYPE: PRT
<213> ORGANISM: Artificial sequence
<220> FEATURE:
<223> OTHER INFORMATION: Synthetic Sequence

<400> SEQUENCE: 38

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 39
<211> LENGTH: 21
<212> TYPE: PRT
<213> ORGANISM: Artificial sequence
<220> FEATURE:
<223> OTHER INFORMATION: Synthetic Sequence

<400> SEQUENCE: 39

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 40
<211> LENGTH: 23
<212> TYPE: PRT
<213> ORGANISM: Artificial sequence
<220> FEATURE:
<223> OTHER INFORMATION: Synthetic Sequence

<400> SEQUENCE: 40

```
Gly Ser Gly Gln Cys Thr Asn Tyr Ala Leu Leu Lys Leu Ala Gly Asp
1               5                   10                  15

Val Glu Ser Asn Pro Gly Pro
            20
```

<210> SEQ ID NO 41
<211> LENGTH: 25
<212> TYPE: PRT
<213> ORGANISM: Artificial sequence
<220> FEATURE:
<223> OTHER INFORMATION: Synthetic Sequence

<400> SEQUENCE: 41

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 42
<211> LENGTH: 99
<212> TYPE: PRT
<213> ORGANISM: Artificial sequence
<220> FEATURE:
<223> OTHER INFORMATION: Synthetic Sequence

<400> SEQUENCE: 42

```
Ile Gln Arg Thr Pro Lys Ile Gln Val Tyr Ser Cys His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```

<210> SEQ ID NO 43
<211> LENGTH: 9
<212> TYPE: PRT
<213> ORGANISM: Artificial sequence
<220> FEATURE:
<223> OTHER INFORMATION: Synthetic Sequence

<400> SEQUENCE: 43

```
Val Tyr Leu Lys Thr Asn Val Phe Leu
1               5
```

<210> SEQ ID NO 44
<211> LENGTH: 10
<212> TYPE: PRT
<213> ORGANISM: Artificial sequence
<220> FEATURE:
<223> OTHER INFORMATION: Synthetic Sequence

<400> SEQUENCE: 44

```
Ala Leu Trp Gly Pro Asp Pro Ala Ala Ala
1               5                   10
```

<210> SEQ ID NO 45
<211> LENGTH: 5
<212> TYPE: PRT
<213> ORGANISM: Artificial sequence
<220> FEATURE:
<223> OTHER INFORMATION: Synthetic Sequence
<220> FEATURE:
<221> NAME/KEY: Misc_feature
<222> LOCATION: (1)..(5)
<223> OTHER INFORMATION: This stretch of residues may be repeated.

<400> SEQUENCE: 45

```
Gly Gly Gly Gly Ser
1               5
```

<210> SEQ ID NO 46
<211> LENGTH: 245
<212> TYPE: PRT
<213> ORGANISM: Artificial sequence
<220> FEATURE:
<223> OTHER INFORMATION: Synthetic Sequence

<400> SEQUENCE: 46

```
Met Arg Ile Phe Ala Val Phe Ile Phe Met Thr Tyr Trp His Leu Leu
1               5                   10                  15

Asn Ala Phe Thr Val Thr Val Pro Lys Ala Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140
```

Asp Pro Val Thr Ser Glu His Glu Leu Thr Cys Gln Ala Glu Gly Tyr
145 150 155 160

Pro Lys Ala Glu Val Ile Trp Thr Ser Ser Asp His Gln Val Leu Ser
165 170 175

Gly Lys Thr Thr Thr Thr Asn Ser Lys Arg Glu Glu Lys Leu Phe Asn
180 185 190

Val Thr Ser Thr Leu Arg Ile Asn Thr Thr Thr Asn Glu Ile Phe Tyr
195 200 205

Cys Thr Phe Arg Arg Leu Asp Pro Glu Glu Asn His Thr Ala Glu Leu
210 215 220

Val Ile Pro Gly Asn Ile Leu Asn Val Ser Ile Lys Ile Cys Leu Thr
225 230 235 240

Leu Ser Pro Ser Thr
245

<210> SEQ ID NO 47
<211> LENGTH: 219
<212> TYPE: PRT
<213> ORGANISM: Artificial sequence
<220> FEATURE:
<223> OTHER INFORMATION: Synthetic Sequence

<400> SEQUENCE: 47

Phe Thr Val Thr Val Pro Lys Ala Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

Leu Gln Ile Thr Asp Val Lys Leu Gln Asp Ala Gly Val Tyr Arg Cys
85 90 95

Met Ile Ser Tyr Gly Gly Ala Asp Tyr Lys Arg Ile Thr Val Lys Val
100 105 110

Asn Ala Pro Tyr Asn Lys Ile Asn Gln Arg Ile Leu Val Val Asp Pro
115 120 125

Val Thr Ser Glu His Glu Leu Thr Cys Gln Ala Glu Gly Tyr Pro Lys
130 135 140

Ala Glu Val Ile Trp Thr Ser Ser Asp His Gln Val Leu Ser Gly Lys
145 150 155 160

Thr Thr Thr Thr Asn Ser Lys Arg Glu Glu Lys Leu Phe Asn Val Thr
165 170 175

Ser Thr Leu Arg Ile Asn Thr Thr Thr Asn Glu Ile Phe Tyr Cys Thr
180 185 190

Phe Arg Arg Leu Asp Pro Glu Glu Asn His Thr Ala Glu Leu Val Ile
195 200 205

Pro Gly Asn Ile Leu Asn Val Ser Ile Lys Ile
210 215

<210> SEQ ID NO 48
<211> LENGTH: 245
<212> TYPE: PRT
<213> ORGANISM: Artificial sequence
<220> FEATURE:
<223> OTHER INFORMATION: Synthetic Sequence

<400> SEQUENCE: 48

Met Arg Ile Phe Ala Val Phe Ile Phe Met Thr Tyr Trp His Leu Leu
1 5 10 15

Asn Ala Phe Thr Val Thr Val Pro Lys Arg Leu Tyr Val Val Glu Tyr
20 25 30

Gly Ser Asn Met Thr Ile Glu Cys Lys Phe Pro Val Glu Lys Gln Leu
35 40 45

Asp Leu Ala Ala Leu Ile Val Tyr Trp Glu Met Glu Asp Lys Asn Ile
50 55 60

Ile Gln Phe Val His Gly Glu Glu Asp Leu Lys Val Gln His Ser Ser
65 70 75 80

Tyr Arg Gln Arg Ala Arg Leu Leu Lys Asp Gln Leu Ser Leu Gly Asn
85 90 95

Ala Ala Leu Gln Ile Thr Asp Val Lys Leu Gln Asp Ala Gly Val Tyr
100 105 110

Arg Cys Met Ile Ser Tyr Gly Gly Ala Asp Tyr Lys Arg Ile Thr Val
115 120 125

Lys Val Asn Ala Pro Tyr Asn Lys Ile Asn Gln Arg Ile Leu Val Val
130 135 140

Asp Pro Val Thr Ser Glu His Glu Leu Thr Cys Gln Ala Glu Gly Tyr
145 150 155 160

Pro Lys Ala Glu Val Ile Trp Thr Ser Ser Asp His Gln Val Leu Ser
165 170 175

Gly Lys Thr Thr Thr Thr Asn Ser Lys Arg Glu Glu Lys Leu Phe Asn
180 185 190

Val Thr Ser Thr Leu Arg Ile Asn Thr Thr Thr Asn Glu Ile Phe Tyr
195 200 205

Cys Thr Phe Arg Arg Leu Asp Pro Glu Glu Asn His Thr Ala Glu Leu
210 215 220

Val Ile Pro Gly Asn Ile Leu Asn Val Ser Ile Lys Ile Cys Leu Thr
225 230 235 240

Leu Ser Pro Ser Thr
245

<210> SEQ ID NO 49
<211> LENGTH: 219
<212> TYPE: PRT
<213> ORGANISM: Artificial sequence
<220> FEATURE:
<223> OTHER INFORMATION: Synthetic Sequence

<400> SEQUENCE: 49

Phe Thr Val Thr Val Pro Lys Arg Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

-continued

```
Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Gly Asn Ile Leu Asn Val Ser Ile Lys Ile
    210                 215


<210> SEQ ID NO 50
<211> LENGTH: 245
<212> TYPE: PRT
<213> ORGANISM: Artificial sequence
<220> FEATURE:
<223> OTHER INFORMATION: Synthetic Sequence

<400> SEQUENCE: 50

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Asp Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220
```

Val Ile Pro Gly Asn Ile Leu Asn Val Ser Ile Lys Ile Cys Leu Thr
225 230 235 240

Leu Ser Pro Ser Thr
245

<210> SEQ ID NO 51
<211> LENGTH: 219
<212> TYPE: PRT
<213> ORGANISM: Artificial sequence
<220> FEATURE:
<223> OTHER INFORMATION: Synthetic Sequence

<400> SEQUENCE: 51

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Asp Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

Leu Gln Ile Thr Asp Val Lys Leu Gln Asp Ala Gly Val Tyr Arg Cys
85 90 95

Met Ile Ser Tyr Gly Gly Ala Asp Tyr Lys Arg Ile Thr Val Lys Val
100 105 110

Asn Ala Pro Tyr Asn Lys Ile Asn Gln Arg Ile Leu Val Val Asp Pro
115 120 125

Val Thr Ser Glu His Glu Leu Thr Cys Gln Ala Glu Gly Tyr Pro Lys
130 135 140

Ala Glu Val Ile Trp Thr Ser Ser Asp His Gln Val Leu Ser Gly Lys
145 150 155 160

Thr Thr Thr Thr Asn Ser Lys Arg Glu Glu Lys Leu Phe Asn Val Thr
165 170 175

Ser Thr Leu Arg Ile Asn Thr Thr Thr Asn Glu Ile Phe Tyr Cys Thr
180 185 190

Phe Arg Arg Leu Asp Pro Glu Glu Asn His Thr Ala Glu Leu Val Ile
195 200 205

Pro Gly Asn Ile Leu Asn Val Ser Ile Lys Ile
210 215

<210> SEQ ID NO 52
<211> LENGTH: 245
<212> TYPE: PRT
<213> ORGANISM: Artificial sequence
<220> FEATURE:
<223> OTHER INFORMATION: Synthetic Sequence

<400> SEQUENCE: 52

Met Arg Ile Phe Ala Val Phe Ile Phe Met Thr Tyr Trp His Leu Leu
1 5 10 15

Asn Ala Phe Thr Val Thr Val Pro Lys Asp Leu Tyr Val Val Glu Tyr
20 25 30

Gly Ser Asn Met Thr Ile Glu Cys Lys Phe Pro Val Glu Lys Gln Leu
35 40 45

Asp Leu Ala Ala Leu Ile Val Tyr Trp Glu Met Glu Asp Lys Asn Ile
50 55 60

```
Ile Asp Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245


<210> SEQ ID NO 53
<211> LENGTH: 219
<212> TYPE: PRT
<213> ORGANISM: Artificial sequence
<220> FEATURE:
<223> OTHER INFORMATION: Synthetic Sequence

<400> SEQUENCE: 53

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Asp
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175
```

-continued

```
Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Gly Asn Ile Leu Asn Val Ser Ile Lys Ile
    210                 215


<210> SEQ ID NO 54
<211> LENGTH: 245
<212> TYPE: PRT
<213> ORGANISM: Artificial sequence
<220> FEATURE:
<223> OTHER INFORMATION: Synthetic Sequence

<400> SEQUENCE: 54

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Arg Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245


<210> SEQ ID NO 55
<211> LENGTH: 219
<212> TYPE: PRT
<213> ORGANISM: Artificial sequence
<220> FEATURE:
<223> OTHER INFORMATION: Synthetic Sequence
```

<400> SEQUENCE: 55

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Arg Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

Leu Gln Ile Thr Asp Val Lys Leu Gln Asp Ala Gly Val Tyr Arg Cys
85 90 95

Met Ile Ser Tyr Gly Gly Ala Asp Tyr Lys Arg Ile Thr Val Lys Val
100 105 110

Asn Ala Pro Tyr Asn Lys Ile Asn Gln Arg Ile Leu Val Val Asp Pro
115 120 125

Val Thr Ser Glu His Glu Leu Thr Cys Gln Ala Glu Gly Tyr Pro Lys
130 135 140

Ala Glu Val Ile Trp Thr Ser Ser Asp His Gln Val Leu Ser Gly Lys
145 150 155 160

Thr Thr Thr Thr Asn Ser Lys Arg Glu Glu Lys Leu Phe Asn Val Thr
165 170 175

Ser Thr Leu Arg Ile Asn Thr Thr Thr Asn Glu Ile Phe Tyr Cys Thr
180 185 190

Phe Arg Arg Leu Asp Pro Glu Glu Asn His Thr Ala Glu Leu Val Ile
195 200 205

Pro Gly Asn Ile Leu Asn Val Ser Ile Lys Ile
210 215

<210> SEQ ID NO 56
<211> LENGTH: 288
<212> TYPE: PRT
<213> ORGANISM: Mus musculus

<400> SEQUENCE: 56

Met Trp Val Arg Gln Val Pro Trp Ser Phe Thr Trp Ala Val Leu Gln
1 5 10 15

Leu Ser Trp Gln Ser Gly Trp Leu Leu Glu Val Pro Asn Gly Pro Trp
20 25 30

Arg Ser Leu Thr Phe Tyr Pro Ala Trp Leu Thr Val Ser Glu Gly Ala
35 40 45

Asn Ala Thr Phe Thr Cys Ser Leu Ser Asn Trp Ser Glu Asp Leu Met
50 55 60

Leu Asn Trp Asn Arg Leu Ser Pro Ser Asn Gln Thr Glu Lys Gln Ala
65 70 75 80

Ala Phe Cys Asn Gly Leu Ser Gln Pro Val Gln Asp Ala Arg Phe Gln
85 90 95

Ile Ile Gln Leu Pro Asn Arg His Asp Phe His Met Asn Ile Leu Asp
100 105 110

Thr Arg Arg Asn Asp Ser Gly Ile Tyr Leu Cys Gly Ala Ile Ser Leu
115 120 125

His Pro Lys Ala Lys Ile Glu Glu Ser Pro Gly Ala Glu Leu Val Val
130 135 140

-continued

```
Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285


<210> SEQ ID NO 57
<211> LENGTH: 288
<212> TYPE: PRT
<213> ORGANISM: Homo sapiens

<400> SEQUENCE: 57

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240
```

-continued

```
Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 58
<211> LENGTH: 306
<212> TYPE: PRT
<213> ORGANISM: Mus musculus

<400> SEQUENCE: 58

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305
```

-continued

<210> SEQ ID NO 59
<211> LENGTH: 288
<212> TYPE: PRT
<213> ORGANISM: Homo sapiens

<400> SEQUENCE: 59

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 60
<211> LENGTH: 227
<212> TYPE: PRT
<213> ORGANISM: Homo sapiens

<400> SEQUENCE: 60

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Asp Glu Leu Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 61
<211> LENGTH: 325
<212> TYPE: PRT
<213> ORGANISM: Homo sapiens

<400> SEQUENCE: 61

Ser Thr Lys Gly Pro Ser Val Phe Pro Leu Ala Pro Cys Ser Arg Ser
1 5 10 15

Thr Ser Glu Ser Thr Ala Ala Leu Gly Cys Leu Val Lys Asp Tyr Phe
20 25 30

Pro Glu Pro Val Thr Val Ser Trp Asn Ser Gly Ala Leu Thr Ser Gly
35 40 45

Val His Thr Phe Pro Ala Val Leu Gln Ser Ser Gly Leu Tyr Ser Leu
50 55 60

Ser Ser Val Val Thr Val Pro Ser Ser Asn Phe Gly Thr Gln Thr Tyr
65 70 75 80

Thr Cys Asn Val Asp His Lys Pro Ser Asn Thr Lys Val Asp Lys Thr
85 90 95

Val Glu Arg Lys Cys Cys Val Glu Cys Pro Pro Cys Pro Ala Pro Pro
100 105 110

Val Ala Gly Pro Ser Val Phe Leu Phe Pro Pro Lys Pro Lys Asp Thr
115 120 125

Leu Met Ile Ser Arg Thr Pro Glu Val Thr Cys Val Val Val Asp Val
130 135 140

Ser His Glu Asp Pro Glu Val Gln Phe Asn Trp Tyr Val Asp Gly Val
145 150 155 160

Glu Val His Asn Ala Lys Thr Lys Pro Arg Glu Glu Gln Phe Asn Ser
165 170 175

Thr Phe Arg Val Val Ser Val Leu Thr Val Val His Gln Asp Trp Leu
180 185 190

-continued

Asn Gly Lys Glu Tyr Lys Cys Lys Val Ser Asn Lys Gly Leu Pro Ala
195 200 205

Pro Ile Glu Lys Thr Ile Ser Lys Thr Lys Gly Gln Pro Arg Glu Pro
210 215 220

Gln Val Tyr Thr Leu Pro Pro Ser Arg Glu Glu Met Thr Lys Asn Gln
225 230 235 240

Val Ser Leu Thr Cys Leu Val Lys Gly Phe Tyr Pro Ser Asp Ile Ala
245 250 255

Val Glu Trp Glu Ser Asn Gly Gln Pro Glu Asn Asn Tyr Lys Thr Thr
260 265 270

Pro Pro Met Leu Asp Ser Asp Gly Ser Phe Phe Leu Tyr Ser Lys Leu
275 280 285

Thr Val Asp Lys Ser Arg Trp Gln Gln Gly Asn Val Phe Ser Cys Ser
290 295 300

Val Met His Glu Ala Leu His Asn His Tyr Thr Gln Lys Ser Leu Ser
305 310 315 320

Leu Ser Pro Gly Lys
325

<210> SEQ ID NO 62
<211> LENGTH: 246
<212> TYPE: PRT
<213> ORGANISM: Homo sapiens

<400> SEQUENCE: 62

His Lys Pro Ser Asn Thr Lys Val Asp Lys Arg Val Glu Leu Lys Thr
1 5 10 15

Pro Leu Gly Asp Thr Thr His Thr Cys Pro Pro Cys Pro Ala Pro Glu
20 25 30

Leu Leu Gly Gly Pro Ser Val Phe Leu Phe Pro Pro Lys Pro Lys Asp
35 40 45

Thr Leu Met Ile Ser Arg Thr Pro Glu Val Thr Cys Val Val Val Asp
50 55 60

Val Ser His Glu Asp Pro Glu Val Lys Phe Asn Trp Tyr Val Asp Gly
65 70 75 80

Val Glu Val His Asn Ala Lys Thr Lys Pro Arg Glu Glu Gln Tyr Asn
85 90 95

Ser Thr Tyr Arg Val Val Ser Val Leu Thr Val Leu His Gln Asp Trp
100 105 110

Leu Asn Gly Lys Glu Tyr Lys Cys Lys Val Ser Asn Lys Ala Leu Pro
115 120 125

Ala Pro Ile Glu Lys Thr Ile Ser Lys Ala Lys Gly Gln Pro Arg Glu
130 135 140

Pro Gln Val Tyr Thr Leu Pro Pro Ser Arg Asp Glu Leu Thr Lys Asn
145 150 155 160

Gln Val Ser Leu Thr Cys Leu Val Lys Gly Phe Tyr Pro Ser Asp Ile
165 170 175

Ala Val Glu Trp Glu Ser Asn Gly Gln Pro Glu Asn Asn Tyr Lys Thr
180 185 190

Thr Pro Pro Val Leu Asp Ser Asp Gly Ser Phe Phe Leu Tyr Ser Lys
195 200 205

Leu Thr Val Asp Lys Ser Arg Trp Gln Gln Gly Asn Val Phe Ser Cys
210 215 220

Ser Val Met His Glu Ala Leu His Asn His Tyr Thr Gln Lys Ser Leu
225 230 235 240

Ser Leu Ser Pro Gly Lys
245

<210> SEQ ID NO 63
<211> LENGTH: 383
<212> TYPE: PRT
<213> ORGANISM: Homo sapiens

<400> SEQUENCE: 63

Pro Thr Lys Ala Pro Asp Val Phe Pro Ile Ile Ser Gly Cys Arg His
1 5 10 15

Pro Lys Asp Asn Ser Pro Val Val Leu Ala Cys Leu Ile Thr Gly Tyr
20 25 30

His Pro Thr Ser Val Thr Val Thr Trp Tyr Met Gly Thr Gln Ser Gln
35 40 45

Pro Gln Arg Thr Phe Pro Glu Ile Gln Arg Arg Asp Ser Tyr Tyr Met
50 55 60

Thr Ser Ser Gln Leu Ser Thr Pro Leu Gln Gln Trp Arg Gln Gly Glu
65 70 75 80

Tyr Lys Cys Val Val Gln His Thr Ala Ser Lys Ser Lys Lys Glu Ile
85 90 95

Phe Arg Trp Pro Glu Ser Pro Lys Ala Gln Ala Ser Ser Val Pro Thr
100 105 110

Ala Gln Pro Gln Ala Glu Gly Ser Leu Ala Lys Ala Thr Thr Ala Pro
115 120 125

Ala Thr Thr Arg Asn Thr Gly Arg Gly Gly Glu Glu Lys Lys Lys Glu
130 135 140

Lys Glu Lys Glu Glu Gln Glu Glu Arg Glu Thr Lys Thr Pro Glu Cys
145 150 155 160

Pro Ser His Thr Gln Pro Leu Gly Val Tyr Leu Leu Thr Pro Ala Val
165 170 175

Gln Asp Leu Trp Leu Arg Asp Lys Ala Thr Phe Thr Cys Phe Val Val
180 185 190

Gly Ser Asp Leu Lys Asp Ala His Leu Thr Trp Glu Val Ala Gly Lys
195 200 205

Val Pro Thr Gly Gly Val Glu Glu Gly Leu Leu Glu Arg His Ser Asn
210 215 220

Gly Ser Gln Ser Gln His Ser Arg Leu Thr Leu Pro Arg Ser Leu Trp
225 230 235 240

Asn Ala Gly Thr Ser Val Thr Cys Thr Leu Asn His Pro Ser Leu Pro
245 250 255

Pro Gln Arg Leu Met Ala Leu Arg Glu Pro Ala Ala Gln Ala Pro Val
260 265 270

Lys Leu Ser Leu Asn Leu Leu Ala Ser Ser Asp Pro Pro Glu Ala Ala
275 280 285

Ser Trp Leu Leu Cys Glu Val Ser Gly Phe Ser Pro Pro Asn Ile Leu
290 295 300

Leu Met Trp Leu Glu Asp Gln Arg Glu Val Asn Thr Ser Gly Phe Ala
305 310 315 320

Pro Ala Arg Pro Pro Pro Gln Pro Arg Ser Thr Thr Phe Trp Ala Trp
325 330 335

Ser Val Leu Arg Val Pro Ala Pro Pro Ser Pro Gln Pro Ala Thr Tyr
340 345 350

```
Thr Cys Val Val Ser His Glu Asp Ser Arg Thr Leu Leu Asn Ala Ser
        355                 360                 365

Arg Ser Leu Glu Val Ser Tyr Val Thr Asp His Gly Pro Met Lys
    370                 375                 380


<210> SEQ ID NO 64
<211> LENGTH: 276
<212> TYPE: PRT
<213> ORGANISM: Homo sapiens

<400> SEQUENCE: 64

Val Thr Ser Thr Leu Thr Ile Lys Glx Ser Asp Trp Leu Gly Glu Ser
1               5                   10                  15

Met Phe Thr Cys Arg Val Asp His Arg Gly Leu Thr Phe Gln Gln Asn
            20                  25                  30

Ala Ser Ser Met Cys Val Pro Asp Gln Asp Thr Ala Ile Arg Val Phe
        35                  40                  45

Ala Ile Pro Pro Ser Phe Ala Ser Ile Phe Leu Thr Lys Ser Thr Lys
    50                  55                  60

Leu Thr Cys Leu Val Thr Asp Leu Thr Thr Tyr Asx Ser Val Thr Ile
65                  70                  75                  80

Ser Trp Thr Arg Glu Glu Asn Gly Ala Val Lys Thr His Thr Asn Ile
                85                  90                  95

Ser Glu Ser His Pro Asn Ala Thr Phe Ser Ala Val Gly Glu Ala Ser
            100                 105                 110

Ile Cys Glu Asp Asx Asp Trp Ser Gly Glu Arg Phe Thr Cys Thr Val
        115                 120                 125

Thr His Thr Asp Leu Pro Ser Pro Leu Lys Gln Thr Ile Ser Arg Pro
    130                 135                 140

Lys Gly Val Ala Leu His Arg Pro Asx Val Tyr Leu Leu Pro Pro Ala
145                 150                 155                 160

Arg Glx Glx Leu Asn Leu Arg Glu Ser Ala Thr Ile Thr Cys Leu Val
                165                 170                 175

Thr Gly Phe Ser Pro Ala Asp Val Phe Val Glu Trp Met Gln Arg Gly
            180                 185                 190

Glu Pro Leu Ser Pro Gln Lys Tyr Val Thr Ser Ala Pro Met Pro Glu
        195                 200                 205

Pro Gln Ala Pro Gly Arg Tyr Phe Ala His Ser Ile Leu Thr Val Ser
    210                 215                 220

Glu Glu Glu Trp Asn Thr Gly Gly Thr Tyr Thr Cys Val Val Ala His
225                 230                 235                 240

Glu Ala Leu Pro Asn Arg Val Thr Glu Arg Thr Val Asp Lys Ser Thr
                245                 250                 255

Gly Lys Pro Thr Leu Tyr Asn Val Ser Leu Val Met Ser Asp Thr Ala
            260                 265                 270

Gly Thr Cys Tyr
        275


<210> SEQ ID NO 65
<211> LENGTH: 353
<212> TYPE: PRT
<213> ORGANISM: Homo sapiens
```

<400> SEQUENCE: 65

Ala Ser Pro Thr Ser Pro Lys Val Phe Pro Leu Ser Leu Cys Ser Thr
1 5 10 15

Gln Pro Asp Gly Asn Val Val Ile Ala Cys Leu Val Gln Gly Phe Phe
20 25 30

Pro Gln Glu Pro Leu Ser Val Thr Trp Ser Glu Ser Gly Gln Gly Val
35 40 45

Thr Ala Arg Asn Phe Pro Pro Ser Gln Asp Ala Ser Gly Asp Leu Tyr
50 55 60

Thr Thr Ser Ser Gln Leu Thr Leu Pro Ala Thr Gln Cys Leu Ala Gly
65 70 75 80

Lys Ser Val Thr Cys His Val Lys His Tyr Thr Asn Pro Ser Gln Asp
85 90 95

Val Thr Val Pro Cys Pro Val Pro Ser Thr Pro Pro Thr Pro Ser Pro
100 105 110

Ser Thr Pro Pro Thr Pro Ser Pro Ser Cys Cys His Pro Arg Leu Ser
115 120 125

Leu His Arg Pro Ala Leu Glu Asp Leu Leu Leu Gly Ser Glu Ala Asn
130 135 140

Leu Thr Cys Thr Leu Thr Gly Leu Arg Asp Ala Ser Gly Val Thr Phe
145 150 155 160

Thr Trp Thr Pro Ser Ser Gly Lys Ser Ala Val Gln Gly Pro Pro Glu
165 170 175

Arg Asp Leu Cys Gly Cys Tyr Ser Val Ser Ser Val Leu Pro Gly Cys
180 185 190

Ala Glu Pro Trp Asn His Gly Lys Thr Phe Thr Cys Thr Ala Ala Tyr
195 200 205

Pro Glu Ser Lys Thr Pro Leu Thr Ala Thr Leu Ser Lys Ser Gly Asn
210 215 220

Thr Phe Arg Pro Glu Val His Leu Leu Pro Pro Pro Ser Glu Glu Leu
225 230 235 240

Ala Leu Asn Glu Leu Val Thr Leu Thr Cys Leu Ala Arg Gly Phe Ser
245 250 255

Pro Lys Asp Val Leu Val Arg Trp Leu Gln Gly Ser Gln Glu Leu Pro
260 265 270

Arg Glu Lys Tyr Leu Thr Trp Ala Ser Arg Gln Glu Pro Ser Gln Gly
275 280 285

Thr Thr Thr Phe Ala Val Thr Ser Ile Leu Arg Val Ala Ala Glu Asp
290 295 300

Trp Lys Lys Gly Asp Thr Phe Ser Cys Met Val Gly His Glu Ala Leu
305 310 315 320

Pro Leu Ala Phe Thr Gln Lys Thr Ile Asp Arg Leu Ala Gly Lys Pro
325 330 335

Thr His Val Asn Val Ser Val Val Met Ala Glu Val Asp Gly Thr Cys
340 345 350

Tyr

<210> SEQ ID NO 66
<211> LENGTH: 222
<212> TYPE: PRT
<213> ORGANISM: Homo sapiens -continued

<400> SEQUENCE: 66

Ala Asp Pro Cys Asp Ser Asn Pro Arg Gly Val Ser Ala Tyr Leu Ser
1 5 10 15

Arg Pro Ser Pro Phe Asp Leu Phe Ile Arg Lys Ser Pro Thr Ile Thr
20 25 30

Cys Leu Val Val Asp Leu Ala Pro Ser Lys Gly Thr Val Asn Leu Thr
35 40 45

Trp Ser Arg Ala Ser Gly Lys Pro Val Asn His Ser Thr Arg Lys Glu
50 55 60

Glu Lys Gln Arg Asn Gly Thr Leu Thr Val Thr Ser Thr Leu Pro Val
65 70 75 80

Gly Thr Arg Asp Trp Ile Glu Gly Glu Thr Tyr Gln Cys Arg Val Thr
85 90 95

His Pro His Leu Pro Arg Ala Leu Met Arg Ser Thr Thr Lys Thr Ser
100 105 110

Gly Pro Arg Ala Ala Pro Glu Val Tyr Ala Phe Ala Thr Pro Glu Trp
115 120 125

Pro Gly Ser Arg Asp Lys Arg Thr Leu Ala Cys Leu Ile Gln Asn Phe
130 135 140

Met Pro Glu Asp Ile Ser Val Gln Trp Leu His Asn Glu Val Gln Leu
145 150 155 160

Pro Asp Ala Arg His Ser Thr Thr Gln Pro Arg Lys Thr Lys Gly Ser
165 170 175

Gly Phe Phe Val Phe Ser Arg Leu Glu Val Thr Arg Ala Glu Trp Glu
180 185 190

Gln Lys Asp Glu Phe Ile Cys Arg Ala Val His Glu Ala Ala Ser Pro
195 200 205

Ser Gln Thr Val Gln Arg Ala Val Ser Val Asn Pro Gly Lys
210 215 220

<210> SEQ ID NO 67
<211> LENGTH: 327
<212> TYPE: PRT
<213> ORGANISM: Homo sapiens

<400> SEQUENCE: 67

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 68
<211> LENGTH: 365
<212> TYPE: PRT
<213> ORGANISM: Homo sapiens

<400> SEQUENCE: 68

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

Ala Glu Gln Arg Arg Val Tyr Leu Glu Gly Arg Cys Val Asp Gly Leu
            180                 185                 190
```

-continued

```
Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Leu Ser Ser Gln Pro
    290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
        355                 360                 365


<210> SEQ ID NO 69
<211> LENGTH: 362
<212> TYPE: PRT
<213> ORGANISM: Homo sapiens

<400> SEQUENCE: 69

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205
```

```
Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360


<210> SEQ ID NO 70
<211> LENGTH: 366
<212> TYPE: PRT
<213> ORGANISM: Homo sapiens

<400> SEQUENCE: 70

Met Arg Val Met Ala Pro Arg Ala Leu Leu Leu Leu Leu Ser Gly Gly
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Asn Tyr Lys Arg Gln Ala Gln
                85                  90                  95

Ala Asp Arg Val Ser Leu Arg Asn Leu Arg Gly Tyr Tyr Asn Gln Ser
            100                 105                 110

Glu Asp Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
        195                 200                 205

Pro Lys Thr His Val Thr His His Pro Leu Ser Asp His Glu Ala Thr
    210                 215                 220
```

```
Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Met Gln His Glu
        275                 280                 285

Gly Leu Gln Glu Pro Leu Thr Leu Ser Trp Glu Pro Ser Ser Gln Pro
    290                 295                 300

Thr Ile Pro Ile Met Gly Ile Val Ala Gly Leu Ala Val Leu Val Val
305                 310                 315                 320

Leu Ala Val Leu Gly Ala Val Val Thr Ala Met Met Cys Arg Arg Lys
                325                 330                 335

Ser Ser Gly Gly Lys Gly Gly Ser Cys Ser Gln Ala Ala Cys Ser Asn
            340                 345                 350

Ser Ala Gln Gly Ser Asp Glu Ser Leu Ile Thr Cys Lys Ala
        355                 360                 365


<210> SEQ ID NO 71
<211> LENGTH: 290
<212> TYPE: PRT
<213> ORGANISM: Mus musculus

<400> SEQUENCE: 71

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240
```

```
Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290


<210> SEQ ID NO 72
<211> LENGTH: 245
<212> TYPE: PRT
<213> ORGANISM: Homo sapiens

<400> SEQUENCE: 72

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245


<210> SEQ ID NO 73
<211> LENGTH: 237
<212> TYPE: PRT
<213> ORGANISM: Mus musculus
```

<400> SEQUENCE: 73

Met Arg Ile Phe Ala Gly Ile Ile Phe Thr Ala Cys Cys His Leu Leu
1 5 10 15

Arg Ala Phe Thr Ile Thr Ala Pro Lys Asp Leu Tyr Val Val Glu Tyr
20 25 30

Gly Ser Asn Val Thr Met Glu Cys Arg Phe Pro Val Glu Arg Glu Leu
35 40 45

Asp Leu Leu Ala Leu Val Val Tyr Trp Glu Lys Glu Asp Glu Gln Val
50 55 60

Ile Gln Phe Val Ala Gly Glu Glu Asp Leu Lys Pro Gln His Ser Asn
65 70 75 80

Phe Arg Gly Arg Ala Ser Leu Pro Lys Asp Gln Leu Leu Lys Gly Asn
85 90 95

Ala Ala Leu Gln Ile Thr Asp Val Lys Leu Gln Asp Ala Gly Val Tyr
100 105 110

Cys Cys Ile Ile Ser Tyr Gly Gly Ala Asp Tyr Lys Arg Ile Thr Leu
115 120 125

Lys Val Asn Ala Pro Tyr Arg Lys Ile Asn Gln Arg Ile Ser Val Asp
130 135 140

Pro Ala Thr Ser Glu His Glu Leu Ile Cys Gln Ala Glu Gly Tyr Pro
145 150 155 160

Glu Ala Glu Val Ile Trp Thr Asn Ser Asp His Gln Pro Val Ser Gly
165 170 175

Lys Arg Ser Val Thr Thr Ser Arg Thr Glu Gly Met Leu Leu Asn Val
180 185 190

Thr Ser Ser Leu Arg Val Asn Ala Thr Ala Asn Asp Val Phe Tyr Cys
195 200 205

Thr Phe Trp Arg Ser Gln Pro Gly Gln Asn His Thr Ala Glu Leu Ile
210 215 220

Ile Pro Glu Leu Pro Ala Thr His Pro Pro Gln Asn Arg
225 230 235

<210> SEQ ID NO 74
<211> LENGTH: 237
<212> TYPE: PRT
<213> ORGANISM: Homo sapiens

<400> SEQUENCE: 74

Met Arg Ile Phe Ala Val Phe Ile Phe Met Thr Tyr Trp His Leu Leu
1 5 10 15

Asn Ala Phe Thr Val Thr Val Pro Lys Asp Leu Tyr Val Val Glu Tyr
20 25 30

Gly Ser Asn Met Thr Ile Glu Cys Lys Phe Pro Val Glu Lys Gln Leu
35 40 45

Asp Leu Ala Ala Leu Ile Val Tyr Trp Glu Met Glu Asp Lys Asn Ile
50 55 60

Ile Gln Phe Val His Gly Glu Glu Asp Leu Lys Val Gln His Ser Ser
65 70 75 80

Tyr Arg Gln Arg Ala Arg Leu Leu Lys Asp Gln Leu Ser Leu Gly Asn
85 90 95

Ala Ala Leu Gln Ile Thr Asp Val Lys Leu Gln Asp Ala Gly Val Tyr
100 105 110

Arg Cys Met Ile Ser Tyr Gly Gly Ala Asp Tyr Lys Arg Ile Thr Val
115 120 125

-continued

```
Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile
225                 230                 235
```

VARIANT PD-L1 POLYPEPTIDES, T-CELL MODULATORY MULTIMERIC POLYPEPTIDES, AND METHODS OF USE THEREOF

CROSS-REFERENCE TO RELATED APPLICATIONS

This application is a U.S. national stage entry under 35 U.S.C. § 371 of PCT International Patent Application No. PCT/US2017/033042, filed May 17, 2017, which claims benefit of U.S. Provisional Application No. 62/338,128, filed May 18, 2016, the contents of each of which are incorporated herein by reference into the subject application.

INTRODUCTION

An adaptive immune response involves the engagement of the T cell receptor (TCR), present on the surface of a T cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T cell modulation (activation or inhibition) and effector function. Following epitope-specific cell targeting, the targeted T cells are activated through engagement of costimulatory proteins found on the APC with counterpart costimulatory proteins the T cells. Both signals—epitope/TCR binding and engagement of APC costimulatory proteins with T cell costimulatory proteins—are required to drive T cell specificity and activation or inhibition. The TCR is specific for a given epitope; however, the costimulatory protein is not epitope specific and instead is generally expressed on all T cells or on large T cell subsets.

SUMMARY

The present disclosure provides variant PD-L1 immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

BRIEF DESCRIPTION OF THE DRAWINGS

FIG. 2A-2M provide an amino acid sequence of a wild-type mouse PD-L1 polypeptide (FIG. 2A); an amino acid sequence of a wild-type human PD-L1 polypeptide (FIG. 2B); a sequence alignment of a mouse and a human PD-L1 amino acid sequence (FIG. 2C); and examples of variant PD-L1 polypeptides (FIG. 2D-2M).

FIG. 3A-3D provides amino acid sequences of mouse PD-1 (FIG. 3A), human PD-1 (FIG. 3B), mouse B7-1 (FIG. 3C), and human B7-1 (FIG. 3D).

FIG. 4A-4C provide amino acid sequences of immunoglobulin Fc polypeptides.

FIG. 5A-5C provide amino acid sequences of human leukocyte antigen (HLA) Class I heavy chain polypeptides. Signal sequences are underlined.

FIG. 6 provides a multiple amino acid sequence alignment of beta-2 microglobulin (β2M) precursors (i.e., including the leader sequence) from *Homo sapiens* (NP_004039.1; SEQ ID NO:3), Pan troglodytes (NP_001009066.1; SEQ ID NO:4), *Macaca mulatta* (NP_001040602.1; SEQ ID NO:5), *Bos taurus* (NP_776318.1; SEQ ID NO:6) and *Mus musculus* (NP_033865.2; SEQ ID NO:7). Amino acids 1-20 are a signal peptide.

FIG. 10 provides Table 1.

FIG. 11 provides Table 2.

FIG. 12 depicts the effect of a PD-L1/synTac on pathogenic epitope-specific $CD8^+$ T cells in vivo.

DEFINITIONS

Figure 1A:
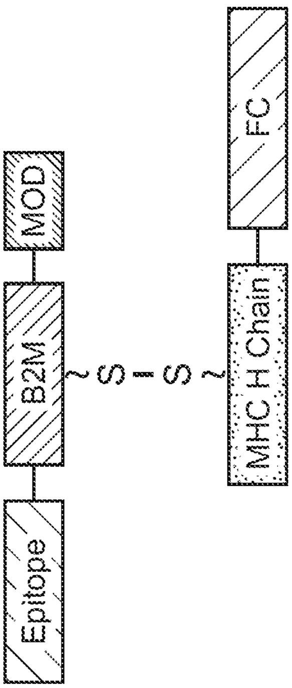
FIG. 1A-1D schematically depict various embodiments of a T-cell modulatory multimeric polypeptide of the present disclosure. In these embodiments, disulfide bonds are formed between MHC (e.g., HLA) polypeptides present in separate polypeptides.
Figure 1B:
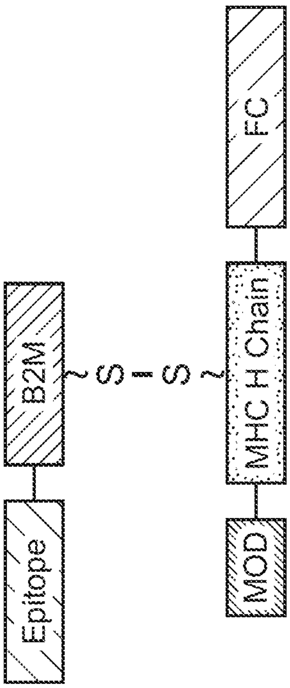
Figure 1C:
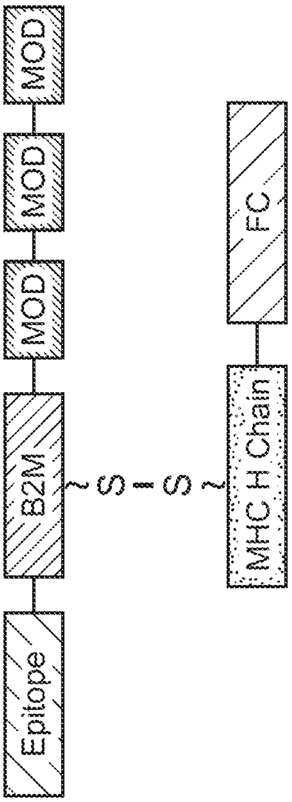
Figure 1D:
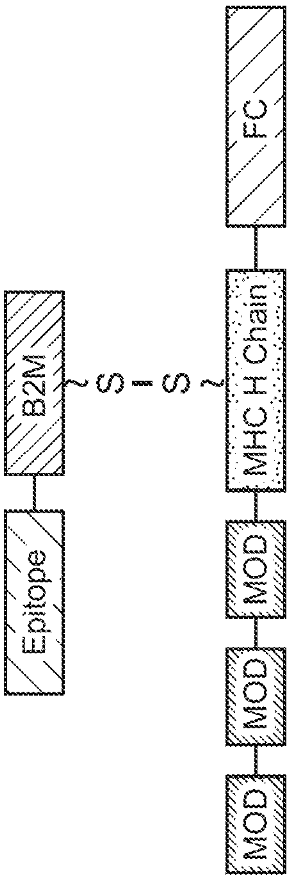

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

"Binding" as used herein (e.g. with reference to binding of a T-cell modulatory multimeric polypeptide of the present disclosure to a polypeptide (e.g., a T-cell receptor) on a T cell) refers to a non-covalent interaction between. Binding interactions are generally characterized by a dissociation constant ($K_D$) of less than $10^{-3}$. Preferred $K_D$ values are $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T cell, a natural killer cell, and the like. An immunological synapse between an APC and a T cell is generally initiated by the interaction of a T cell antigen receptor and major histocompatibility complex molecules, e.g., as described in Bromley et al., Annu Rev Immunol. 2001; 19:375-96; the disclosure of which is incorporated herein by reference in its entirety.

"T cell" includes all types of immune cells expressing CD3, including T-helper cells ($CD4^+$ cells), cytotoxic T-cells ($CD8^+$ cells), T-regulatory cells (Treg), and NK-T cells.

"Co-stimulatory polypeptide," as the term is used herein, includes a polypeptide on an antigen presenting cell (APC) (e.g., a dendritic cell, a B cell, and the like) that specifically binds a cognate co-stimulatory polypeptide on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like.

A "modulatory domain" of a T-cell modulatory multimeric polypeptide of the present disclosure comprises a co-stimulatory polypeptide.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

A "host cell," as used herein, denotes an in vivo or in vitro eukaryotic cell or a cell from a multicellular organism (e.g., a cell line) cultured as a unicellular entity, which eukaryotic cells can be, or have been, used as recipients for a nucleic acid (e.g., an expression vector that comprises a nucleotide sequence encoding a multimeric polypeptide of the present disclosure), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified eukaryotic host cell is genetically modified by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a PD-L1 variant" includes a plurality of such variants and reference to "the HLA polypeptide" includes reference to one or more HLA polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

A T-cell modulatory multimeric polypeptide of the present disclosure is also referred to as a "synTac polypeptide." A synTac polypeptide of the present disclosure comprises a variant modulatory domain, where the variant modulatory domain exhibits reduced binding affinity to an immunomodulatory polypeptide (e.g., an immunomodulatory polypeptide present on a T-cell), compared to the affinity of a wild-type PD-L1 modulatory domain for the immunomodulatory polypeptide (e.g., PD-1 or B7-1). A synTac polypeptide of the present disclosure can modulate (e.g., inhibit) the activity of a target T-cell. A synTac polypeptide of the present disclosure provides for enhanced target cell specificity.

Variant Immunomodulatory Polypeptides

The present disclosure provides variant PD-L1 modulatory polypeptides. A wild-type amino acid sequence of human PD-L1 is provided in FIG. 2A.

Wild-type PD-L1 binds to PD1 and to B7-1. An amino acid sequence of a mouse PD-1 is provided in FIG. 3A; and an amino acid sequence of a human PD-1 is provided in FIG. 3B. An amino acid sequence of a mouse B7-1 is provided in FIG. 3C; and an amino acid sequence of a human B7-1 is provided in FIG. 3D. In some cases, variant PD-L1 polypeptide of the present disclosure binds to PD-1 with reduced affinity compared to binding of wild-type PD-L1 to PD1. In some cases, variant PD-L1 polypeptide of the present disclosure binds to B7-1 with reduced affinity compared to binding of wild-type PD-L1 to B7-1. In some cases, variant PD-L1 polypeptide of the present disclosure binds to PD-1 with substantially the same affinity as the binding affinity of wild-type PD-L1 to PD-1; and binds to B7-1 with reduced affinity compared to binding of wild-type PD-L1 to B7-1. In some cases, variant PD-L1 polypeptide of the present disclosure binds to PD-1 with reduced affinity compared to binding of wild-type PD-L1 to PD1; and binds to B7-1 with reduced affinity compared to binding of wild-type PD-L1 to B7-1. In some cases, variant PD-L1 polypeptide of the present disclosure binds to PD-1 with reduced affinity compared to binding of wild-type PD-L1 to PD-1; and binds to B7-1 with substantially the same affinity as the binding affinity of wild-type PD-L1 to B7-1.

In some cases, a variant PD-L1 polypeptide of the present disclosure exhibits reduced binding affinity to PD-1, compared to the binding affinity of a PD-L1 polypeptide comprising the amino acid sequence depicted in FIG. 2A for PD-1 (e.g., a PD-1 polypeptide comprising the amino acid sequence depicted in FIG. 3A). For example, in some cases, a variant PD-L1 polypeptide of the present disclosure binds PD-1 with a binding affinity that is less than the binding affinity of a PD-L1 polypeptide comprising the amino acid sequence depicted in FIG. 2A for a PD-1 polypeptide comprising the amino acid sequence depicted in FIG. 3A. For example, in some cases, a variant PD-L1 polypeptide of the present disclosure binds PD-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a PD-L1 polypeptide comprising the amino acid sequence depicted in FIG. 2A for PD-1 (e.g., a PD-1 polypeptide comprising the amino acid sequence depicted in FIG. 3A).

In some cases, a variant PD-L1 polypeptide of the present disclosure exhibits reduced binding affinity to PD-1, compared to the binding affinity of a PD-L1 polypeptide comprising the amino acid sequence depicted in FIG. 2B for PD-1 (e.g., a PD-1 polypeptide comprising the amino acid sequence depicted in FIG. 3B). For example, in some cases, a variant PD-L1 polypeptide of the present disclosure binds PD-1 with a binding affinity that is less than the binding affinity of a PD-L1 polypeptide comprising the amino acid sequence depicted in FIG. 2B for a PD-1 polypeptide comprising the amino acid sequence depicted in FIG. 3B. For example, in some cases, a variant PD-L1 polypeptide of the present disclosure binds PD-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a PD-L1 polypeptide comprising the amino acid sequence depicted in FIG. 2B for PD-1 (e.g., a PD-1 polypeptide comprising the amino acid sequence depicted in FIG. 3B).

In some cases, a wild-type mouse PD-L1 ectodomain comprises the following amino acid sequence: FT ITAPKDLYVV EYGSNVTMEC RFPVERELDL LALVVYWEKE DEQVIQFVAG EEDLKPQHSN FRGRASLPKD QLLKGNAALQ ITDVKLQDAG VYCCIISYGG ADYKRITLKV NAPYRKINQR ISVDPATSEH ELICQAEGYP EAEVIWTNSD HQPVSGKRSV TTSRTEGMLL NVTSSLRVNA TANDVFYCTF WRSQPGQNHT AELIIPELPA THPPQNR (SEQ ID NO:1).

In some cases, a wild-type human PD-L1 ectodomain comprises the following amino acid sequence: FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:2).

In some cases, a variant PD-L1 polypeptide of the present disclosure exhibits reduced binding affinity to PD-1, compared to the binding affinity of a PD-L1 polypeptide comprising the amino acid sequence set forth in SEQ ID NO:1 for PD-1 (e.g., a PD-1 polypeptide comprising the amino acid sequence depicted in FIG. 3A). For example, in some cases, a variant PD-L1 polypeptide of the present disclosure binds PD-1 with a binding affinity that is less than the binding affinity of a PD-L1 polypeptide comprising the amino acid sequence set forth in SEQ ID NO:1 for a PD-1 polypeptide comprising the amino acid sequence depicted in FIG. 3A. For example, in some cases, a variant PD-L1 polypeptide of the present disclosure binds PD-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a PD-L1 polypeptide comprising the amino acid sequence set forth in SEQ ID NO:1 for PD-1 (e.g., a PD-1 polypeptide comprising the amino acid sequence depicted in FIG. 3A).

In some cases, a variant PD-L1 polypeptide of the present disclosure exhibits reduced binding affinity to PD-1, compared to the binding affinity of a PD-L1 polypeptide comprising the amino acid sequence set forth in SEQ ID NO:2 for PD-1 (e.g., a PD-1 polypeptide comprising the amino acid sequence depicted in FIG. 3B). For example, in some cases, a variant PD-L1 polypeptide of the present disclosure binds PD-1 with a binding affinity that is less than the binding affinity of a PD-L1 polypeptide comprising the amino acid sequence set forth in SEQ ID NO:2 for a PD-1 polypeptide comprising the amino acid sequence depicted in FIG. 3B. For example, in some cases, a variant PD-L1 polypeptide of the present disclosure binds PD-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a PD-L1 polypeptide comprising the amino acid sequence set forth in SEQ ID NO:2 for PD-1 (e.g., a PD-1 polypeptide comprising the amino acid sequence depicted in FIG. 3B).

In some cases, a variant PD-L1 polypeptide of the present disclosure exhibits reduced binding affinity to PD-1, as described above; and retains at least 80%, at least 85%, at least 90%, at least 95%, at least 98%, or at least 99%, of the binding affinity of a wild-type PD-L1 polypeptide for a wild-type B7-1 polypeptide. For example, in some cases, a variant PD-L1 polypeptide of the present disclosure exhibits reduced binding affinity to PD-1, compared to the binding affinity of a PD-L1 polypeptide comprising the amino acid sequence set forth in SEQ ID NO:2 for PD-1 (e.g., a PD-1 polypeptide comprising the amino acid sequence depicted in FIG. 3B); and retains at least 80%, at least 85%, at least 90%, at least 95%, at least 98%, or at least 99%, of the binding affinity of a wild-type PD-L1 polypeptide (e.g., a PD-L1 polypeptide comprising the amino acid sequence set forth in SEQ ID NO:2) for a wild-type B7-1 polypeptide (e.g., a B7-1 polypeptide comprising the amino acid sequence depicted in FIG. 3D).

In some cases, a variant PD-L1 polypeptide of the present disclosure exhibits from about 40% to about 60% reduced binding affinity to PD-1 (e.g., to a PD-1 polypeptide comprising the amino acid sequence depicted in FIG. 3B), compared to the binding affinity of a PD-L1 polypeptide comprising the amino acid sequence set forth in SEQ ID NO:2 for the PD-1 polypeptide; and retains at least 80%, at least 85%, at least 90%, at least 95%, at least 98%, or at least 99%, of the binding affinity of a wild-type PD-L1 polypeptide (e.g., a PD-L1 polypeptide comprising the amino acid sequence set forth in SEQ ID NO:2) for a wild-type B7-1 polypeptide (e.g., a B7-1 polypeptide comprising the amino acid sequence depicted in FIG. 3D).

In some cases, a variant PD-L1 polypeptide of the present disclosure exhibits from about 40% to about 60% reduced binding affinity to PD-1 (e.g., to a PD-1 polypeptide comprising the amino acid sequence depicted in FIG. 3A), compared to the binding affinity of a PD-L1 polypeptide comprising the amino acid sequence set forth in SEQ ID NO:1 for the PD-1 polypeptide; and retains at least 80%, at least 85%, at least 90%, at least 95%, at least 98%, or at least 99%, of the binding affinity of a wild-type PD-L1 polypeptide (e.g., a PD-L1 polypeptide comprising the amino acid sequence set forth in SEQ ID NO:1) for a wild-type B7-1 polypeptide (e.g., a B7-1 polypeptide comprising the amino acid sequence depicted in FIG. 3C).

In some cases, a variant PD-L1 polypeptide of the present disclosure has a binding affinity to PD-1 that is from 1 nM to 1 mM. In some cases, a variant PD-L1 polypeptide of the present disclosure has a binding affinity to PD-1 that is from 100 nM to 100 μM. As another example, in some cases, a variant PD-L1 polypeptide of the present disclosure has a binding affinity for PD1 (e.g., a PD1 polypeptide comprising the amino acid sequence depicted in FIG. 3) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

A variant PD-L1 polypeptide of the present disclosure can have a single amino acid substitution relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has from 2 to 10 amino acid substitutions relative to a wild-type PD-L1 polypeptide (e e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 2 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 3 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 4 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 5 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 6 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 7 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 8 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 9 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2). In some cases, a variant PD-L1 polypeptide of the present disclosure has 10 amino acid substitutions relative to a wild-type PD-L1 polypeptide (e.g., a PD-L1 polypeptide comprising the amino acid sequence depicted in FIG. 2A or 2B, or as set forth in SEQ ID NO:1 or SEQ ID NO:2).

A variant PD-L1 polypeptide of the present disclosure can have a length of from 200 amino acids to 240 amino acids. For example, in some cases, a variant PD-L1 polypeptide of the present disclosure has a length of from 200 amino acids to 220 amino acids, or from 220 amino acids to 240 amino acids. In some cases, a variant PD-L1 polypeptide of the present disclosure has a length of from 200 amino acids to 219 amino acids. In some cases, a variant PD-L1 polypeptide of the present disclosure has a length of 219 amino acids.

D26 Substitution

In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is an amino acid other than an aspartic acid, e.g., where amino acid 26 is Gly, Ala, Val, Leu, Ile, Pro, Phe, Tyr, Trp, Ser, Thr, Cys, Met, Asn, Gln, Lys, Arg, His, or Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Ala, Gly, Val, Leu, or Ile. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Ala, Gly, Val, Leu, Ile, or Arg. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Ala. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Gly. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Val. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Leu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Ile. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 26 is Arg. In some cases, the variant PD-L1 polypeptide exhibits from about 40% to about 60% reduced binding affinity to PD-1 (e.g., to a PD-1 polypeptide comprising the amino acid sequence depicted in FIG. 3B), compared to the binding affinity of a PD-L1 polypeptide comprising the amino acid sequence set forth in FIG. 2B (or set forth in SEQ ID NO:2) for the PD-1 polypeptide; and retains at least 80%, at least 85%, at least 90%, at least 95%, at least 98%, or at least 99%, of the binding affinity of a wild-type PD-L1 polypeptide (e.g., a PD-L1 polypeptide comprising the amino acid sequence set forth in FIG. 2B or SEQ ID NO:2) for a wild-type B7-1 polypeptide (e.g., a B7-1 polypeptide comprising the amino acid sequence depicted in FIG. 3D).

In some cases, a variant PD-L1 polypeptide of the present disclosure comprises the amino acid sequence set forth in FIG. 2B, with an amino acid substitution at D26. In some cases, a variant PD-L1 polypeptide of the present disclosure comprises the amino acid sequence set forth in SEQ ID NO:2, with an amino acid substitution at D8. For example, in some cases, a variant PD-L1 polypeptide of the present disclosure comprises the amino acid sequence set forth in FIG. 2B, where amino acid 26 is any amino acid other than aspartic acid; for example, amino acid 26 can be Gly, Ala, Val, Leu, Ile, Pro, Phe, Tyr, Trp, Ser, Thr, Cys, Met, Asn, Gln, Lys, Arg, His, or Glu. In some cases, a variant PD-L1 polypeptide of the present disclosure comprises the amino acid sequence set forth in FIG. 2B, where amino acid 26 is Ala, Gly, Val, Leu, or Ile. In some cases, a variant PD-L1 polypeptide of the present disclosure comprises the amino acid sequence set forth in FIG. 2B, where amino acid 26 is Ala, Gly, Val, Leu, Ile, or Arg. In some cases, a variant PD-L1 polypeptide of the present disclosure comprises the amino acid sequence set forth in FIG. 2B, where amino acid 26 is Ala instead of Asp. In some cases, a variant PD-L1 polypeptide of the present disclosure comprises the amino acid sequence set forth in FIG. 2B, where amino acid 26 is Val instead of Asp. In some cases, a variant PD-L1 polypeptide of the present disclosure comprises the amino acid sequence set forth in FIG. 2B, where amino acid 26 is Leu instead of Asp. In some cases, a variant PD-L1 polypeptide of the present disclosure comprises the amino acid sequence set forth in FIG. 2B, where amino acid 26 is Gly instead of Asp. In some cases, a variant PD-L1 polypeptide of the present disclosure comprises the amino acid sequence set forth in FIG. 2B, where amino acid 26 is Ile instead of Asp. In some cases, a variant PD-L1 polypeptide of the present disclosure comprises the amino acid sequence set forth in FIG. 2B, where amino acid 26 is Arg instead of Asp.

In some cases, a variant PD-L1 polypeptide of the present disclosure comprises the amino acid sequence set forth in SEQ ID NO:2, with an amino acid substitution at D8. For example, in some cases, a variant PD-L1 polypeptide of the present disclosure comprises the amino acid sequence set forth in SEQ ID NO:2, where amino acid 8 is any amino acid other than aspartic acid; for example, amino acid 8 can be Gly, Ala, Val, Leu, Ile, Pro, Phe, Tyr, Trp, Ser, Thr, Cys, Met, Asn, Gln, Lys, Arg, His, or Glu. In some cases, a variant PD-L1 polypeptide of the present disclosure comprises the amino acid sequence set forth in SEQ ID NO:2, where amino acid 8 is Ala, Gly, Val, Leu, or Ile instead of Asp. In some cases, a variant PD-L1 polypeptide of the present disclosure comprises the amino acid sequence set forth in SEQ ID NO:2, where amino acid 8 is Ala, Gly, Val, Leu, Ile, or Arg instead of Asp. In some cases, a variant PD-L1 polypeptide of the present disclosure comprises the amino acid sequence set forth in SEQ ID NO:2, where amino acid 8 is Ala instead of Asp. In some cases, a variant PD-L1 polypeptide of the present disclosure comprises the amino acid sequence set forth in SEQ ID NO:2, where amino acid 8 is Val instead of Asp. In some cases, a variant PD-L1 polypeptide of the present disclosure comprises the amino acid sequence set forth in SEQ ID NO:2, where amino acid 8 is Leu instead of Asp. In some cases, a variant PD-L1 polypeptide of the present disclosure comprises the amino acid sequence set forth in SEQ ID NO:2, where amino acid 8 is Gly instead of Asp. In some cases, a variant PD-L1 polypeptide of the present disclosure comprises the amino acid sequence set forth in SEQ ID NO:2, where amino acid 8 is Ile. In some cases, a variant PD-L1 polypeptide of the present disclosure comprises the amino acid sequence set forth in SEQ ID NO:2, where amino acid 8 is Arg instead of Asp.

In some cases, a variant PD-L1 polypeptide of the present disclosure comprises the amino acid sequence depicted in FIG. 2D. In some cases, variant PD-L1 polypeptide of the present disclosure comprises the amino acid sequence depicted in FIG. 2E. In some cases, variant PD-L1 polypeptide of the present disclosure comprises the amino acid sequence depicted in FIG. 2F. In some cases, variant PD-L1 polypeptide of the present disclosure comprises the amino acid sequence depicted in FIG. 2G.

T37 Substitution

In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is an amino acid other than threonine, e.g., where amino acid 37 is Gly, Ala, Val, Leu, Ile, Pro, Phe, Tyr, Trp, Ser, Cys, Met, Asn, Gln, Lys, Arg, His, Asp, or Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Gly, Ala, Val, Leu, Ile, Arg, Lys, or His. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Arg, Lys, or His. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Gly, Ala, Val, Leu, or Ile. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Arg. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Lys. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is His. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Gly. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Ala. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Val. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Leu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 37 is Ile. In some cases, the variant PD-L1 polypeptide exhibits from about 15% to about 35% of the binding affinity to PD-1 (e.g., to a PD-1 polypeptide comprising the amino acid sequence depicted in FIG. 3B) exhibited by a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 70% to about 90% reduced binding affinity to B7-1) compared to the binding affinity of a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, a variant PD-L1 polypeptide of the present disclosure comprises the amino acid sequence set forth in FIG. 2B, with an amino acid substitution at T37. In some cases, a variant PD-L1 polypeptide of the present disclosure comprises the amino acid sequence set forth in SEQ ID NO:2, with an amino acid substitution at T19. For example, in some cases, a variant PD-L1 polypeptide of the present disclosure comprises the amino acid sequence set forth in FIG. 2B, where amino acid 37 is any amino acid other than threonine; for example, amino acid 37 can be Gly, Ala, Val, Leu, Ile, Pro, Phe, Tyr, Trp, Ser, Cys, Met, Asn, Gln, Lys, Arg, His, Asp, or Glu. In some cases, a variant PD-L1 polypeptide of the present disclosure comprises the amino acid sequence set forth in FIG. 2B, where amino acid 37 is Gly, Ala, Val, Leu, Ile, Arg, His, or Lys, instead of Thr. In some cases, a variant PD-L1 polypeptide of the present disclosure comprises the amino acid sequence set forth in FIG. 2B, where amino acid 37 is Gly, Ala, Val, Leu, or Ile, instead of Thr. In some cases, a variant PD-L1 polypeptide of the present disclosure comprises the amino acid sequence set forth in FIG. 2B, where amino acid 37 is Arg, His, or Lys, instead of Thr. In some cases, a variant PD-L1 polypeptide of the present disclosure comprises the amino acid sequence set forth in FIG. 2B, where amino acid 37 is Arg instead of Thr. In some cases, a variant PD-L1 polypeptide of the present disclosure comprises the amino acid sequence set forth in FIG. 2B, where amino acid 37 is Lys instead of Thr. In some cases, a variant PD-L1 polypeptide of the present disclosure comprises the amino acid sequence set forth in FIG. 2B, where amino acid 37 is His instead of Thr. In some cases, a variant PD-L1 polypeptide of the present disclosure comprises the amino acid sequence set forth in FIG. 2B, where amino acid 37 is Gly instead of Thr. In some cases, a variant PD-L1 polypeptide of the present disclosure comprises the amino acid sequence set forth in FIG. 2B, where amino acid 37 is Ala instead of Thr. In some cases, a variant PD-L1 polypeptide of the present disclosure comprises the amino acid sequence set forth in FIG. 2B, where amino acid 37 is Val instead of Thr. In some cases, a variant PD-L1 polypeptide of the present disclosure comprises the amino acid sequence set forth in FIG. 2B, where amino acid 37 is Leu instead of Thr. In some cases, a variant PD-L1 polypeptide of the present disclosure comprises the amino acid sequence set forth in FIG. 2B, where amino acid 37 is Ile instead of Thr.

In some cases, a variant PD-L1 polypeptide of the present disclosure comprises the amino acid sequence set forth in SEQ ID NO:2, with an amino acid substitution at T19. For example, in some cases, a variant PD-L1 polypeptide of the present disclosure comprises the amino acid sequence set forth in SEQ ID NO:2, where amino acid 19 is any amino acid other than threonine; for example, amino acid 19 can be Gly, Ala, Val, Leu, Ile, Pro, Phe, Tyr, Trp, Ser, Cys, Met, Asn, Gln, Lys, Arg, His, Asp, or Glu. In some cases, a variant PD-L1 polypeptide of the present disclosure comprises the amino acid sequence set forth in SEQ ID NO:2, where amino acid 19 is Gly, Ala, Val, Leu, Ile, Arg, His, or Lys instead of Thr. In some cases, a variant PD-L1 polypeptide of the present disclosure comprises the amino acid sequence set forth in SEQ ID NO:2, where amino acid 19 is Gly, Ala, Val, Leu, or Ile, instead of Thr. In some cases, a variant PD-L1 polypeptide of the present disclosure comprises the amino acid sequence set forth in SEQ ID NO:2, where amino acid 19 is Arg, His, or Lys instead of Thr. In some cases, a variant PD-L1 polypeptide of the present disclosure comprises the amino acid sequence set forth in SEQ ID NO:2, where amino acid 19 is Arg instead of Thr. In some cases, a variant PD-L1 polypeptide of the present disclosure comprises the amino acid sequence set forth in SEQ ID NO:2, where amino acid 19 is Lys instead of Thr. In some cases, a variant PD-L1 polypeptide of the present disclosure comprises the amino acid sequence set forth in SEQ ID NO:2, where amino acid 54 is His instead of 19. In some cases, a variant PD-L1 polypeptide of the present disclosure comprises the amino acid sequence set forth in SEQ ID NO:2, where amino acid 19 is Gly instead of Thr. In some cases, a variant PD-L1 polypeptide of the present disclosure comprises the amino acid sequence set forth in SEQ ID NO:2, where amino acid 19 is Ala instead of Thr. In some cases, a variant PD-L1 polypeptide of the present disclosure comprises the amino acid sequence set forth in SEQ ID NO:2, where amino acid 19 is Val instead of Thr. In some cases, a variant PD-L1 polypeptide of the present disclosure comprises the amino acid sequence set forth in SEQ ID NO:2, where amino acid 19 is Leu instead of Thr. In some cases, a variant PD-L1 polypeptide of the present disclosure comprises the amino acid sequence set forth in SEQ ID NO:2, where amino acid 19 is Ile instead of Thr.

I54 Substitution

In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is an amino acid other than isoleucine, e.g., where amino acid 54 is Gly, Ala, Val, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is an amino acid other than isoleucine or valine, e.g., where amino acid 54 is Gly, Ala, Leu, Pro, Phe, Tyr, Trp, Ser, Thr, Cys, Met, Asn, Gin, Lys, Arg, His, Asp, or Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is Ala, Gly, Leu, Glu, or Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is Glu or Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is Ala. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is Gly. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is Leu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 54 is Glu. In some cases, the variant PD-L1 polypeptide exhibits from about 70% to about 100% of the binding affinity to PD-1 (e.g., to a PD-1 polypeptide comprising the amino acid sequence depicted in FIG. 2B) exhibited by a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 40% to about 90% reduced binding affinity to B7-1) compared to the binding affinity of a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is an amino acid other than valine, e.g., where amino acid 54 is Gly, Ala, Leu, Ile, Pro, Phe, Tyr, Trp, Ser, Thr, Cys, Met, Asn, Gln, Lys, Arg, His, Asp, or Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is an amino acid other than isoleucine or valine, e.g., where amino acid 54 is Gly, Ala, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is Ala, Gly, Leu, Glu, or Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is Glu or Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is Ala. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is Gly. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is Leu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2A, where amino acid 54 is Glu. In some cases, the variant PD-L1 polypeptide exhibits from about 70% to about 100% of the binding affinity to PD-1 (e.g., to a PD-1 polypeptide comprising the amino acid sequence depicted in FIG. 3A) exhibited by a PD-L1 polypeptide comprising the amino acid sequence set forth in FIG. 2A (or set forth in SEQ ID NO:1) for the PD-1 polypeptide; and exhibits reduced binding affinity to B7-1 (e.g., exhibits from about 40% to about 90% reduced binding affinity to B7-1) compared to the binding affinity of a wild-type PD-L1 polypeptide (e.g., a PD-L1 polypeptide comprising the amino acid sequence set forth in FIG. 2A or in SEQ ID NO:1) for a wild-type B7-1 polypeptide (e.g., a B7-1 polypeptide comprising the amino acid sequence depicted in FIG. 3C).

In some cases, a variant PD-L1 polypeptide of the present disclosure comprises the amino acid sequence set forth in FIG. 2B, with an amino acid substitution at I54. In some cases, a variant PD-L1 polypeptide of the present disclosure comprises the amino acid sequence set forth in SEQ ID NO:2, with an amino acid substitution at I36. For example, in some cases, a variant PD-L1 polypeptide of the present disclosure comprises the amino acid sequence set forth in FIG. 2B, where amino acid 54 is any amino acid other than isoleucine; for example, amino acid 54 can be Gly, Ala, Val, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in FIG. 2B, where amino acid 54 is any amino acid other than isoleucine or valine; for example, amino acid 54 can be Gly, Ala, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in FIG. 2B, where amino acid 54 is Ala, Gly, Leu, or Asp, instead of Ile. In some cases, a variant PD-L1 polypeptide of the present disclosure comprises the amino acid sequence set forth in FIG. 2B, where amino acid 54 is Ala instead of Ile. In some cases, a variant PD-L1 polypeptide of the present disclosure comprises the amino acid sequence set forth in FIG. 2B, where amino acid 54 is Leu instead of Ile. In some cases, a variant PD-L1 polypeptide of the present disclosure comprises the amino acid sequence set forth in FIG. 2B, where amino acid 54 is Gly instead of Ile. In some cases, a variant PD-L1 polypeptide of the present disclosure comprises the amino acid sequence set forth in FIG. 2B, where amino acid 54 is Asp instead of Ile.

In some cases, a variant PD-L1 polypeptide of the present disclosure comprises the amino acid sequence set forth in FIG. 2A, with an amino acid substitution at V54. In some cases, a variant PD-L1 polypeptide of the present disclosure comprises the amino acid sequence set forth in SEQ ID NO:1, with an amino acid substitution at V36. For example, in some cases, a variant PD-L1 polypeptide of the present disclosure comprises the amino acid sequence set forth in FIG. 2A, where amino acid 54 is any amino acid other than valine; for example, amino acid 54 can be Gly, Ala, Leu, Ile, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in FIG. 2A, where amino acid 54 is any amino acid other than isoleucine or valine; for example, amino acid 54 can be Gly, Ala, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in FIG. 2A, where amino acid 54 is Ala, Gly, Leu, Glu, or Asp, instead of Val. In some cases, a variant PD-L1 polypeptide of the present disclosure comprises the amino acid sequence set forth in FIG. 2A, where amino acid 54 is Glu or Asp, instead of Val. In some cases, a variant PD-L1 polypeptide of the present disclosure comprises the amino acid sequence set forth in FIG. 2A, where amino acid 54 is Ala instead of Val. In some cases, a variant PD-L1 polypeptide of the present disclosure comprises the amino acid sequence set forth in FIG. 2A, where amino acid 54 is Leu instead of Val. In some cases, a variant PD-L1 polypeptide of the present disclosure comprises the amino acid sequence set forth in FIG. 2A, where amino acid 54 is Gly instead of Val. In some cases, a variant PD-L1 polypeptide of the present disclosure comprises the amino acid sequence set forth in FIG. 2A, where amino acid 54 is Asp instead of Val. In some cases, a variant PD-L1 polypeptide of the present disclosure comprises the amino acid sequence set forth in FIG. 2A, where amino acid 54 is Glu instead of Val.

In some cases, a variant PD-L1 polypeptide of the present disclosure comprises the amino acid sequence set forth in SEQ ID NO:2, with an amino acid substitution at Ile-36. For example, in some cases, a variant PD-L1 polypeptide of the present disclosure comprises the amino acid sequence set forth in SEQ ID NO:2, where amino acid 36 is any amino acid other than isoleucine; for example, amino acid 36 can be Gly, Ala, Val, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in SEQ ID NO:2, where amino acid 36 is any amino acid other than isoleucine or valine; for example, amino acid 36 can be Gly, Ala, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in SEQ ID NO:2, where amino acid 36 is Ala, Gly, Leu, or Asp instead of Ile. In some cases, a variant PD-L1 polypeptide of the present disclosure comprises the amino acid sequence set forth in SEQ ID NO:2, where amino acid 36 is Ala instead of Ile. In some cases, a variant PD-L1 polypeptide of the present disclosure comprises the amino acid sequence set forth in SEQ ID NO:2, where amino acid 36 is Leu instead of Ile. In some cases, a variant PD-L1 polypeptide of the present disclosure comprises the amino acid sequence set forth in SEQ ID NO:2, where amino acid 36 is Gly instead of Ile. In some cases, a variant PD-L1 polypeptide of the present disclosure comprises the amino acid sequence set forth in SEQ ID NO:2, where amino acid 36 is Asp instead of Ile.

In some cases, a variant PD-L1 polypeptide of the present disclosure comprises the amino acid sequence set forth in SEQ ID NO:1, with an amino acid substitution at V36. For example, in some cases, a variant PD-L1 polypeptide of the present disclosure comprises the amino acid sequence set forth in SEQ ID NO:1, where amino acid 36 is any amino acid other than valine; for example, amino acid 36 can be Gly, Ala, Leu, Ile, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in SEQ ID NO:1, where amino acid 36 is any amino acid other than isoleucine or valine; for example, amino acid 36 can be Gly, Ala, Leu, Pro, Phe, Tyr, Trp, Ser, Thr, Cys, Met, Asn, Gln, Lys, Arg, His, Asp, or Glu. In some cases, a variant PD-L1 polypeptide of the present disclosure comprises the amino acid sequence set forth in SEQ ID NO:1, where amino acid 36 is Ala, Gly, Leu, Glu, or Asp instead of Val. In some cases, a variant PD-L1 polypeptide of the present disclosure comprises the amino acid sequence set forth in SEQ ID NO:1, where amino acid 36 is Glu or Asp instead of Val. In some cases, a variant PD-L1 polypeptide of the present disclosure comprises the amino acid sequence set forth in SEQ ID NO:1, where amino acid 36 is Ala instead of Val. In some cases, a variant PD-L1 polypeptide of the present disclosure comprises the amino acid sequence set forth in SEQ ID NO:1, where amino acid 36 is Leu instead of Val. In some cases, a variant PD-L1 polypeptide of the present disclosure comprises the amino acid sequence set forth in SEQ ID NO:1, where amino acid 36 is Gly instead of Val. In some cases, a variant PD-L1 polypeptide of the present disclosure comprises the amino acid sequence set forth in SEQ ID NO:1, where amino acid 36 is Asp instead of Val. In some cases, a variant PD-L1 polypeptide of the present disclosure comprises the amino acid sequence set forth in SEQ ID NO:1, where amino acid 36 is Glu instead of Val.

In some cases, a variant PD-L1 polypeptide of the present disclosure comprises the amino acid sequence depicted in FIG. 2H. In some cases, variant PD-L1 polypeptide of the present disclosure comprises the amino acid sequence depicted in FIG. 2I.

Q66 Substitution

In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 66 is an amino acid other than glutamine, e.g., where amino acid 66 is Gly, Ala, Val, Leu, Ile, Pro, Phe, Tyr, Trp, Ser, Thr, Cys, Met, Asn, Lys, Arg, His, Asp, or Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 66 is Glu or Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 66 is Glu. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 66 is Asp. In some cases, the variant PD-L1 polypeptide exhibits from about 80% to about 100% of the binding affinity to PD-1 (e.g., to a PD-1 polypeptide comprising the amino acid sequence depicted in FIG. 3B) exhibited by a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 40% to about 90% reduced binding affinity to B7-1) compared to the binding affinity of a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, a variant PD-L1 polypeptide of the present disclosure comprises the amino acid sequence set forth in FIG. 2B, with an amino acid substitution at Q66. In some cases, a variant PD-L1 polypeptide of the present disclosure comprises the amino acid sequence set forth in SEQ ID NO:2, with an amino acid substitution at Q48. For example, in some cases, a variant PD-L1 polypeptide of the present disclosure comprises the amino acid sequence set forth in FIG. 2B, where amino acid 66 is any amino acid other than glutamine; for example, amino acid 66 can be Gly, Ala, Val, Leu, Ile, Pro, Phe, Tyr, Trp, Ser, Thr, Cys, Met, Asn, Lys, Arg, His, Asp, or Glu. In some cases, a variant PD-L1 polypeptide of the present disclosure comprises the amino acid sequence set forth in FIG. 2B, where amino acid 66 is Ala, Gly, Leu, Glu, or Asp, instead of Gln. In some cases, a variant PD-L1 polypeptide of the present disclosure comprises the amino acid sequence set forth in FIG. 2B, where amino acid 66 is Glu or Asp, instead of Gln. In some cases, a variant PD-L1 polypeptide of the present disclosure comprises the amino acid sequence set forth in FIG. 2B, where amino acid 66 is Ala instead of Gln. In some cases, a variant PD-L1 polypeptide of the present disclosure comprises the amino acid sequence set forth in FIG. 2B, where amino acid 66 is Leu instead of Gln. In some cases, a variant PD-L1 polypeptide of the present disclosure comprises the amino acid sequence set forth in FIG. 2B, where amino acid 66 is Gly instead of Gln. In some cases, a variant PD-L1 polypeptide of the present disclosure comprises the amino acid sequence set forth in FIG. 2B, where amino acid 66 is Asp instead of Gln. In some cases, a variant PD-L1 polypeptide of the present disclosure comprises the amino acid sequence set forth in FIG. 2B, where amino acid 66 is Glu instead of Gln.

In some cases, a variant PD-L1 polypeptide of the present disclosure comprises the amino acid sequence set forth in SEQ ID NO:2, with an amino acid substitution at Q48. For example, in some cases, a variant PD-L1 polypeptide of the present disclosure comprises the amino acid sequence set forth in SEQ ID NO:2, where amino acid 48 is any amino acid other than glutamine; for example, amino acid 48 can be Gly, Ala, Val, Leu, Ile, Pro, Phe, Tyr, Trp, Ser, Thr, Cys, Met, Asn, Lys, Arg, His, Asp, or Glu. In some cases, a variant PD-L1 polypeptide of the present disclosure comprises the amino acid sequence set forth in SEQ ID NO:2, where amino acid 48 is Ala, Gly, Leu, Glu, or Asp instead of Gln. In some cases, a variant PD-L1 polypeptide of the present disclosure comprises the amino acid sequence set forth in SEQ ID NO:2, where amino acid 48 is Glu or Asp instead of Gln. In some cases, a variant PD-L1 polypeptide of the present disclosure comprises the amino acid sequence set forth in SEQ ID NO:2, where amino acid 48 is Ala instead of Gln. In some cases, a variant PD-L1 polypeptide of the present disclosure comprises the amino acid sequence set forth in SEQ ID NO:2, where amino acid 48 is Leu instead of Gln. In some cases, a variant PD-L1 polypeptide of the present disclosure comprises the amino acid sequence set forth in SEQ ID NO:2, where amino acid 48 is Gly instead of Gln. In some cases, a variant PD-L1 polypeptide of the present disclosure comprises the amino acid sequence set forth in SEQ ID NO:2, where amino acid 48 is Asp instead of Gln. In some cases, a variant PD-L1 polypeptide of the present disclosure comprises the amino acid sequence set forth in SEQ ID NO:2, where amino acid 48 is Glu instead of Gln.

In some cases, a variant PD-L1 polypeptide of the present disclosure comprises the amino acid sequence depicted in FIG. 2J. In some cases, variant PD-L1 polypeptide of the present disclosure comprises the amino acid sequence depicted in FIG. 2K.

E72 Substitution

In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 72 is an amino acid other than glutamic acid, e.g., where amino acid 72 is Gly, Ala, Val, Leu, Ile, Pro, Phe, Tyr, Trp, Ser, Thr, Cys, Met, Asn, Gln, Lys, Arg, His, or Asp. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 72 is Arg, Lys, or His. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 72 is Asp, Arg, Lys, or His. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 72 is Arg. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 72 is Lys. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 72 is His. In some cases, a variant PD-L1 polypeptide of the present disclosure comprises an amino acid sequence having at least 90%, at least 95%, at least 98%, or at least 99%, amino acid sequence identity to the amino acid sequence depicted in FIG. 2B, where amino acid 72 is Asp. In some cases, the variant PD-L1 polypeptide exhibits from about 30% to about 60% of the binding affinity to PD-1 (e.g., to a PD-1 polypeptide comprising the amino acid sequence depicted in FIG. 3B) exhibited by a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 40% to about 90% reduced binding affinity to B7-1) compared to the binding affinity of a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, a variant PD-L1 polypeptide of the present disclosure comprises the amino acid sequence set forth in FIG. 2B, with an amino acid substitution at E72. In some cases, a variant PD-L1 polypeptide of the present disclosure comprises the amino acid sequence set forth in SEQ ID NO:2, with an amino acid substitution at E54. For example, in some cases, a variant PD-L1 polypeptide of the present disclosure comprises the amino acid sequence set forth in FIG. 2B, where amino acid 72 is any amino acid other than glutamic acid; for example, amino acid 72 can be Gly, Ala, Val, Leu, Ile, Pro, Phe, Tyr, Trp, Ser, Thr, Cys, Met, Asn, Gln, Lys, Arg, His, or Asp. In some cases, a variant PD-L1 polypeptide of the present disclosure comprises the amino acid sequence set forth in FIG. 2B, where amino acid 72 is Asp, Arg, His, or Lys, instead of Glu. In some cases, a variant PD-L1 polypeptide of the present disclosure comprises the amino acid sequence set forth in FIG. 2B, where amino acid 72 is Arg, His, or Lys, instead of Glu. In some cases, a variant PD-L1 polypeptide of the present disclosure comprises the amino acid sequence set forth in FIG. 2B, where amino acid 72 is Arg instead of Glu. In some cases, a variant PD-L1 polypeptide of the present disclosure comprises the amino acid sequence set forth in FIG. 2B, where amino acid 72 is Lys instead of Glu. In some cases, a variant PD-L1 polypeptide of the present disclosure comprises the amino acid sequence set forth in FIG. 2B, where amino acid 72 is His instead of Glu. In some cases, a variant PD-L1 polypeptide of the present disclosure comprises the amino acid sequence set forth in FIG. 2B, where amino acid 72 is Asp instead of Glu.

In some cases, a variant PD-L1 polypeptide of the present disclosure comprises the amino acid sequence set forth in SEQ ID NO:2, with an amino acid substitution at E54. For example, in some cases, a variant PD-L1 polypeptide of the present disclosure comprises the amino acid sequence set forth in SEQ ID NO:2, where amino acid 54 is any amino acid other than glutamic acid; for example, amino acid 54 can be Gly, Ala, Val, Leu, Ile, Pro, Phe, Tyr, Trp, Ser, Thr, Cys, Met, Asn, Gln, Lys, Arg, His, or Asp. In some cases, a variant PD-L1 polypeptide of the present disclosure comprises the amino acid sequence set forth in SEQ ID NO:2, where amino acid 54 is Asp, Arg, His, or Lys instead of Glu. In some cases, a variant PD-L1 polypeptide of the present disclosure comprises the amino acid sequence set forth in SEQ ID NO:2, where amino acid 54 is Arg, His, or Lys instead of Glu. In some cases, a variant PD-L1 polypeptide of the present disclosure comprises the amino acid sequence set forth in SEQ ID NO:2, where amino acid 54 is Arg instead of Glu. In some cases, a variant PD-L1 polypeptide of the present disclosure comprises the amino acid sequence set forth in SEQ ID NO:2, where amino acid 54 is Lys instead of Glu. In some cases, a variant PD-L1 polypeptide of the present disclosure comprises the amino acid sequence set forth in SEQ ID NO:2, where amino acid 54 is His instead of Glu. In some cases, a variant PD-L1 polypeptide of the present disclosure comprises the amino acid sequence set forth in SEQ ID NO:2, where amino acid 54 is Asp instead of Glu.

In some cases, a variant PD-L1 polypeptide of the present disclosure comprises the amino acid sequence depicted in FIG. 2L. In some cases, variant PD-L1 polypeptide of the present disclosure comprises the amino acid sequence depicted in FIG. 2M.

Fusion Polypeptides

The present disclosure provides PD-L1 fusion polypeptides. A fusion polypeptide of the present disclosure comprises: a) a variant PD-L1 polypeptide of the present disclosure; and b) a heterologous fusion partner. In some cases, the heterologous fusion partner is fused to the N-terminus of the variant PD-L1 polypeptide. In some cases, the heterologous fusion partner is fused to the C-terminus of the variant PD-L1 polypeptide. In some cases, a PD-L1 fusion polypeptide of the present disclosure comprises a first heterologous fusion partner fused to the N-terminus of the variant PD-L1 polypeptide, and a second heterologous fusion partner fused to the C-terminus of the variant PD-L1 polypeptide.

The total length of a PD-L1 fusion polypeptide of the present disclosure can range from 245 amino acids to 2000 amino acids. For example, a PD-L1 fusion polypeptide of the present disclosure can range from 245 amino acids to 250 amino acids, from 250 amino acids to 275 amino acids, from 275 amino acids to 300 amino acids, from 300 amino acids to 350 amino acids, from 350 amino acids, from 350 amino acids to 400 amino acids, from 400 amino acids, from 400 amino acids to 450 amino acids, from 450 amino acids to 500 amino acids, from 500 amino acids to 600 amino acids, from 600 amino acids to 700 amino acids, from 700 amino acids to 800 amino acids, from 800 amino acids to 900 amino acids, from 900 amino acids to 1000 amino acids, from 1000 amino acids to 1250 amino acids, from 1250 amino acids to 1500 amino acids, from 1500 amino acids to 1750 amino acids, or from 1750 amino acids to 2000 amino acids.

Suitable fusion partners include, but are not limited to, a transmembrane domain; an immunoglobulin Fc region (e.g., an IgG Fc region); an antigen-binding region of an antibody; a cytokine; an immunomodulatory domain; an intracellular signaling domain; and the like.

T-Cell Modulatory Multimeric Polypeptides

The present disclosure provides multimeric (e.g., heterodimeric, heterotrimeric) polypeptides. The multimeric polypeptides are T cell modulatory polypeptides, and are also referred to herein as "T-cell modulatory multimeric polypeptides," or "synTac" (for "immunological synapse for T cell activation"). FIG. 1A-1D provide schematic depictions of various T-cell modulatory multimeric polypeptides of the present disclosure. A T-cell modulatory multimeric polypeptide of the present disclosure is also referred to as a "synTac polypeptide" or a "multimeric polypeptide." Where a T-cell modulatory multimeric polypeptide of the present disclosure comprises a PD-L1 immunomodulatory polypeptide (e.g., a variant PD-L1 immunomodulatory polypeptide of the present disclosure), such a T-cell modulatory multimeric polypeptide is also referred to herein as a "PD-L1/synTac."

In some cases, a synTac polypeptide of the present disclosure comprises a variant PD-L1 immunomodulatory polypeptide of the present disclosure. In some cases, a synTac polypeptide of the present disclosure comprises a variant PD-L1 immunomodulatory polypeptide comprising an amino acid substitution as depicted in FIG. 10 or FIG. 11.

Thus, in some cases, a variant PD-L1 polypeptide present in a multimeric polypeptide of the present disclosure comprises a substitution of D26 of the amino acid sequence depicted in FIG. 2B; or D8 of the amino acid sequence set forth in SEQ ID NO:2. In some cases, a variant PD-L1 polypeptide present in a multimeric polypeptide of the present disclosure comprises a substitution of T37 of the amino acid sequence depicted in FIG. 2B; or T19 of the amino acid sequence set forth in SEQ ID NO:2. In some cases, a variant PD-L1 polypeptide present in a multimeric polypeptide of the present disclosure comprises a substitution of D49 of the amino acid sequence depicted in FIG. 2B; or D31 of the amino acid sequence set forth in SEQ ID NO:2. In some cases, a variant PD-L1 polypeptide present in a multimeric polypeptide of the present disclosure comprises a substitution of L53 of the amino acid sequence depicted in FIG. 2B; or L35 of the amino acid sequence set forth in SEQ ID NO:2. In some cases, a variant PD-L1 polypeptide present in a multimeric polypeptide of the present disclosure comprises a substitution of I54 (V54 in mouse PD-L1) of the amino acid sequence depicted in FIG. 2B; or I36 of the amino acid sequence set forth in SEQ ID NO:2. In some cases, a variant PD-L1 polypeptide present in a multimeric polypeptide of the present disclosure comprises a substitution of Y56 of the amino acid sequence depicted in FIG. 2B; or Y38 of the amino acid sequence set forth in SEQ ID NO:2. In some cases, a variant PD-L1 polypeptide present in a multimeric polypeptide of the present disclosure comprises a substitution of Y56 of the amino acid sequence depicted in FIG. 2B; or Y38 of the amino acid sequence set forth in SEQ ID NO:2. In some cases, a variant PD-L1 polypeptide present in a multimeric polypeptide of the present disclosure comprises a substitution of Q66 of the amino acid sequence depicted in FIG. 2B; or Q48 of the amino acid sequence set forth in SEQ ID NO:2. In some cases, a variant PD-L1 polypeptide present in a multimeric polypeptide of the present disclosure comprises a substitution of Q66 of the amino acid sequence depicted in FIG. 2B; or Q48 of the amino acid sequence set forth in SEQ ID NO:2. In some cases, a variant PD-L1 polypeptide present in a multimeric polypeptide of the present disclosure comprises a substitution of E72 of the amino acid sequence depicted in FIG. 2B; or E54 of the amino acid sequence set forth in SEQ ID NO:2. In some cases, a variant PD-L1 polypeptide present in a multimeric polypeptide of the present disclosure comprises a substitution of M115 (I115 of mouse PD-L1) of the amino acid sequence depicted in FIG. 2B; or M97 of the amino acid sequence set forth in SEQ ID NO:2. In some cases, a variant PD-L1 polypeptide present in a multimeric polypeptide of the present disclosure comprises a substitution of I116 of the amino acid sequence depicted in FIG. 2B; or I98 of the amino acid sequence set forth in SEQ ID NO:2. In some cases, a variant PD-L1 polypeptide present in a multimeric polypeptide of the present disclosure comprises a substitution of G119 of the amino acid sequence depicted in FIG. 2B; or G101 of the amino acid sequence set forth in SEQ ID NO:2. In some cases, a variant PD-L1 polypeptide present in a multimeric polypeptide of the present disclosure comprises a substitution of G120 of the amino acid sequence depicted in FIG. 2B; or G102 of the amino acid sequence set forth in SEQ ID NO:2. In some cases, a variant PD-L1 polypeptide present in a multimeric polypeptide of the present disclosure comprises a substitution of G120 of the amino acid sequence depicted in FIG. 2B; or G102 of the amino acid sequence set forth in SEQ ID NO:2. In some cases, a variant PD-L1 polypeptide present in a multimeric polypeptide of the present disclosure comprises a substitution of A121 of the amino acid sequence depicted in FIG. 2B; or A103 of the amino acid sequence set forth in SEQ ID NO:2. In some cases, a variant PD-L1 polypeptide present in a multimeric polypeptide of the present disclosure comprises a substitution of D122 of the amino acid sequence depicted in FIG. 2B; or D104 of the amino acid sequence set forth in SEQ ID NO:2. In some cases, a variant PD-L1 polypeptide present in a multimeric polypeptide of the present disclosure comprises a substitution of Y123 of the amino acid sequence depicted in FIG. 2B; or Y105 of the amino acid sequence set forth in SEQ ID NO:2. In some cases, a variant PD-L1 polypeptide present in a multimeric polypeptide of the present disclosure comprises a substitution of K124 of the amino acid sequence depicted in FIG. 2B; or K106 of the amino acid sequence set forth in SEQ ID NO:2. In some cases, a variant PD-L1 polypeptide present in a multimeric polypeptide of the present disclosure comprises a substitution of R125 of the amino acid sequence depicted in FIG. 2B; or K107 of the amino acid sequence set forth in SEQ ID NO:2.

As noted above, in some cases, a variant PD-L1 polypeptide present in a multimeric polypeptide of the present disclosure exhibits reduced binding affinity for PD1, compared to the binding affinity of wild-type PD-L1 to PD1. In some cases, a multimeric polypeptide of the present disclosure that comprises a variant PD-L1 polypeptide of the present disclosure also exhibits reduced binding affinity to PD1, compared to a control multimeric polypeptide comprising a wild-type PD-L1 (e.g., a PD-L1 polypeptide comprising the amino acid sequence depicted in FIG. 2A or 2B, or comprising the amino acid sequence depicted in SEQ ID NO:1 or SEQ ID NO:2).

In some cases, a variant PD-L1 polypeptide present in a multimeric polypeptide of the present disclosure binds to B7-1 with reduced affinity compared to binding affinity of wild-type PD-L1 for B7-1. In some cases, a multimeric polypeptide of the present disclosure that comprises a variant PD-L1 polypeptide of the present disclosure also exhibits reduced binding affinity to B7-1, compared to a control multimeric polypeptide comprising a wild-type PD-L1 (e.g., a PD-L1 polypeptide comprising the amino acid sequence depicted in FIG. 2A or 2B, or comprising the amino acid sequence depicted in SEQ ID NO:1 or SEQ ID NO:2).

In some cases, a variant PD-L1 polypeptide present in a multimeric polypeptide of the present disclosure binds to PD-1 with substantially the same affinity as the binding affinity of wild-type PD-L1 to PD-1; and binds to B7-1 with reduced affinity compared to binding of wild-type PD-L1 to B7-1. In some cases, a multimeric polypeptide of the present disclosure that comprises a variant PD-L1 polypeptide of the present disclosure also exhibits substantially the same affinity for PD-1 as a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2); and also binds B7-1 with reduced binding affinity for B7-1, compared to a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2).

In some cases, a variant PD-L1 polypeptide present in a multimeric polypeptide of the present disclosure binds to PD-1 with reduced affinity compared to binding of wild-type PD-L1 to PD1; and binds to B7-1 with reduced affinity compared to binding of wild-type PD-L1 to B7-1. In some cases, a multimeric polypeptide of the present disclosure that comprises a variant PD-L1 polypeptide of the present disclosure also exhibits reduced binding affinity to B7-1, compared to a control multimeric polypeptide comprising a wild-type PD-L1 (e.g., a PD-L1 polypeptide comprising the amino acid sequence depicted in FIG. 2A or 2B, or comprising the amino acid sequence depicted in SEQ ID NO:1 or SEQ ID NO:2); and also binds B7-1 with reduced binding affinity for B7-1, compared to a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2).

In some cases, a variant PD-L1 polypeptide present in a multimeric polypeptide of the present disclosure binds to PD-1 with reduced affinity compared to binding of wild-type PD-L1 to PD-1; and binds to B7-1 with substantially the same affinity as the binding affinity of wild-type PD-L1 to B7-1. In some cases, a multimeric polypeptide of the present disclosure that comprises a variant PD-L1 polypeptide of the present disclosure also exhibits reduced binding affinity to B7-1, compared to a control multimeric polypeptide comprising a wild-type PD-L1 (e.g., a PD-L1 polypeptide comprising the amino acid sequence depicted in FIG. 2A or 2B, or comprising the amino acid sequence depicted in SEQ ID NO:1 or SEQ ID NO:2); and also exhibits substantially the same affinity for B7-1 as a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2).

In some cases, a synTac polypeptide of the present disclosure exhibits reduced binding affinity to PD1, compared to the binding affinity of a control synTac polypeptide comprising a PD-L1 polypeptide comprising the amino acid sequence depicted in FIG. 2A or FIG. 2B, or SEQ ID NO:1 or SEQ ID NO:2, for PD1. For example, in some cases, a synTac polypeptide of the present disclosure binds PD1 with a binding affinity that is less than the binding affinity of a control synTac polypeptide comprising a PD-L1 polypeptide comprising the amino acid sequence depicted in FIG. 2A for a PD1 polypeptide comprising the amino acid sequence depicted in FIG. 3A. For example, in some cases, a synTac polypeptide of the present disclosure binds PD1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in FIG. 2A for PD1 (e.g., a PD1 polypeptide comprising the amino acid sequence depicted in FIG. 3A). As another example, in some cases, a synTac polypeptide of the present disclosure binds PD1 with a binding affinity that is less than the binding affinity of a control synTac polypeptide comprising a PD-L1 polypeptide comprising the amino acid sequence depicted in FIG. 2B for a PD1 polypeptide comprising the amino acid sequence depicted in FIG. 3B. For example, in some cases, a synTac polypeptide of the present disclosure binds PD1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in FIG. 2B for PD1 (e.g., a PD1 polypeptide comprising the amino acid sequence depicted in FIG. 3B).

In some cases, a synTac polypeptide of the present disclosure exhibits reduced binding affinity to PD1, compared to the binding affinity of a control synTac polypeptide comprising a PD-L1 polypeptide comprising the amino acid sequence depicted in SEQ ID NO:1 for PD1. For example, in some cases, a synTac polypeptide of the present disclosure binds PD1 with a binding affinity that is less than the binding affinity of a control synTac polypeptide comprises a PD-L1 polypeptide comprising the amino acid sequence depicted in SEQ ID NO:1 for a PD1 polypeptide comprising the amino acid sequence depicted in FIG. 3A. For example, in some cases, a synTac polypeptide of the present disclosure binds PD1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in SEQ ID NO:1 for PD1 (e.g., a PD1 polypeptide comprising the amino acid sequence depicted in FIG. 3A).

In some cases, a synTac polypeptide of the present disclosure exhibits reduced binding affinity to PD1, compared to the binding affinity of a control synTac polypeptide comprising a PD-L1 polypeptide comprising the amino acid sequence depicted in SEQ ID NO:2 for PD1. For example, in some cases, a synTac polypeptide of the present disclosure binds PD1 with a binding affinity that is less than the binding affinity of a control synTac polypeptide comprises a PD-L1 polypeptide comprising the amino acid sequence depicted in SEQ ID NO:2 for a PD1 polypeptide comprising the amino acid sequence depicted in FIG. 3B. For example, in some cases, a synTac polypeptide of the present disclosure binds PD1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in SEQ ID NO:2 for PD1 (e.g., a PD1 polypeptide comprising the amino acid sequence depicted in FIG. 3B).

In some cases, a synTac polypeptide of the present disclosure exhibits reduced binding affinity to B7-1, compared to the binding affinity of a control synTac polypeptide comprising a PD-L1 polypeptide comprising the amino acid sequence depicted in FIG. 2A or FIG. 2B, or SEQ ID NO:1 or SEQ ID NO:2, for B7-1. For example, in some cases, a synTac polypeptide of the present disclosure binds B7-1 with a binding affinity that is less than the binding affinity of a control synTac polypeptide comprising a PD-L1 polypeptide comprising the amino acid sequence depicted in FIG. 2A for a B7-1 polypeptide comprising the amino acid sequence depicted in FIG. 3C. For example, in some cases, a synTac polypeptide of the present disclosure binds B7-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in FIG. 2A for B7-1 (e.g., a B7-1 polypeptide comprising the amino acid sequence depicted in FIG. 3C). As another example, in some cases, a synTac polypeptide of the present disclosure binds B7-1 with a binding affinity that is less than the binding affinity of a control synTac polypeptide comprising a PD-L1 polypeptide comprising the amino acid sequence depicted in FIG. 2B for a PD1 polypeptide comprising the amino acid sequence depicted in FIG. 3D. For example, in some cases, a synTac polypeptide of the present disclosure binds B7-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in FIG. 2B for B7-1 (e.g., a B7-1 polypeptide comprising the amino acid sequence depicted in FIG. 3D).

In some cases, a synTac polypeptide of the present disclosure exhibits reduced binding affinity to B7-1, compared to the binding affinity of a control synTac polypeptide comprising a PD-L1 polypeptide comprising the amino acid sequence depicted in SEQ ID NO:1 for B7-1. For example, in some cases, a synTac polypeptide of the present disclosure binds B7-1 with a binding affinity that is less than the binding affinity of a control synTac polypeptide comprises a PD-L1 polypeptide comprising the amino acid sequence depicted in SEQ ID NO:1 for a B7-1 polypeptide comprising the amino acid sequence depicted in FIG. 3C. For example, in some cases, a synTac polypeptide of the present disclosure binds B7-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in SEQ ID NO:1 for B7-1 (e.g., a B7-1 polypeptide comprising the amino acid sequence depicted in FIG. 3C).

In some cases, a synTac polypeptide of the present disclosure exhibits reduced binding affinity to B7-1, compared to the binding affinity of a control synTac polypeptide comprising a PD-L1 polypeptide comprising the amino acid sequence depicted in SEQ ID NO:2 for B7-1. For example, in some cases, a synTac polypeptide of the present disclosure binds B7-1 with a binding affinity that is less than the binding affinity of a control synTac polypeptide comprises a PD-L1 polypeptide comprising the amino acid sequence depicted in SEQ ID NO:2 for a B7-1 polypeptide comprising the amino acid sequence depicted in FIG. 3D. For example, in some cases, a synTac polypeptide of the present disclosure binds B7-1 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a PD-L1 polypeptide comprising the amino acid sequence depicted in SEQ ID NO:2 for B7-1 (e.g., a B7-1 polypeptide comprising the amino acid sequence depicted in FIG. 3D).

As noted above, in some cases, a multimeric polypeptide of the present disclosure that comprises a variant PD-L1 polypeptide of the present disclosure exhibits substantially the same affinity for B7-1 (e.g., a B7-1 polypeptide comprising the amino acid sequence depicted in FIG. 3C or FIG. 3D) as a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2). For example, in some cases, a multimeric polypeptide of the present disclosure that comprises a variant PD-L1 polypeptide of the present disclosure exhibits at least 75%, at least 80%, at least 85%, at least 90%, at least 95%, at least 98%, or at least 99%, of the affinity for B7-1 (e.g., a B7-1 polypeptide comprising the amino acid sequence depicted in FIG. 3C or FIG. 3D) as a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2).

As noted above, in some cases, a multimeric polypeptide of the present disclosure that comprises a variant PD-L1 polypeptide of the present disclosure exhibits substantially the same affinity for PD1 (e.g., a PD1 polypeptide comprising the amino acid sequence depicted in FIG. 3A or FIG. 3B) as a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2). For example, in some cases, a multimeric polypeptide of the present disclosure that comprises a variant PD-L1 polypeptide of the present disclosure exhibits at least 75%, at least 80%, at least 85%, at least 90%, at least 95%, at least 98%, or at least 99%, of the affinity for PD1 (e.g., a PD1 polypeptide comprising the amino acid sequence depicted in FIG. 3A or FIG. 3B) as a control multimeric polypeptide comprising a wild-type PD-L1 polypeptide (e.g., a PD-L1 polypeptide comprising the amino acid sequence depicted in FIG. 2A or 2B, or comprising the amino acid sequence depicted in SEQ ID NO:1 or SEQ ID NO:2).

In some cases, a synTac polypeptide of the present disclosure has a binding affinity for PD1 that is from 1 nM to about 1 mM. In some cases, a synTac polypeptide of the present disclosure has a binding affinity for PD1 that is from 100 nM to about 100 μM. In some cases, a synTac polypeptide of the present disclosure has a binding affinity for PD1 that is from about 100 nM to 500 nM. For example, in some cases, a synTac polypeptide of the present disclosure has a binding affinity for PD1 (e.g., a PD1 polypeptide comprising the amino acid sequence depicted in FIG. 3A or FIG. 3B) that is from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, or from about 450 nM to about 500 nM. In some cases, a synTac polypeptide of the present disclosure has a binding affinity for PD1 (e.g., a PD1 polypeptide comprising the amino acid sequence depicted in FIG. 3A or FIG. 3B) that is from about 500 nM to 1 μM. For example, in some cases, a synTac polypeptide of the present disclosure has a binding affinity for PD1 (e.g., a PD1 polypeptide comprising the amino acid sequence depicted in FIG. 3A or FIG. 3B) that is from about 500 nM to about 600 nM, from about 600 nM to about 700 nM, from about 700 nM to about 800 nM, from about 800 nM to about 900 nM, or from about 900 nM to about 1 μM. In some cases, a synTac polypeptide of the present disclosure has a binding affinity for PD1 (e.g., a PD1 polypeptide comprising the amino acid sequence depicted in FIG. 3A or FIG. 3B) that is from about 1 μM to 10 μM. For example, in some cases, a synTac polypeptide of the present disclosure has a binding affinity for PD1 (e.g., a PD1 polypeptide comprising the amino acid sequence depicted in FIG. 3A or FIG. 3B) that is from about 1 μM to 2 μM, from about 2 μM to about 3 μM, from about 3 μM to about 4 μM, from about 4 μM to about 5 μM, from about 5 μM to about 6 μM, from about 6 μM to about 7 μM, from about 7 μM to about 8 μM, from about 8 μM to about 9 μM, or from about 9 μM to about 10 μM. In some cases, a synTac polypeptide of the present disclosure has a binding affinity for PD1 (e.g., a PD1 polypeptide comprising the amino acid sequence depicted in FIG. 3A or FIG. 3B) that is from about 10 μM to 100 μM. For example, in some cases, a synTac polypeptide of the present disclosure has a binding affinity for PD1 (e.g., a PD1 polypeptide comprising the amino acid sequence depicted in FIG. 3A or FIG. 3B) that is from about 10 μM to about 20 μM, from about 20 μM to about 30 μM, from about 30 μM to about 40 μM, from about 40 μM to about 50 μM, from about 50 μM to about 60 μM, from about 60 μM to about 70 μM, from about 70 μM to about 80 μM, from about 80 μM to about 90 μM, or from about 90 μM to about 100 μM.

A variant PD-L1 polypeptide present in a synTac polypeptide of the present disclosure can have a single amino acid substitution relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has from 2 to 10 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 2 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 3 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 4 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 5 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 6 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 7 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 8 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 9 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2). In some cases, a variant PD-L1 polypeptide present in a synTac polypeptide of the present disclosure has 10 amino acid substitutions relative to a wild-type PD-L1 polypeptide (e.g., a PD-L1 polypeptide comprising the amino acid sequence depicted in FIG. 2A or FIG. 2B or as set forth in SEQ ID NO:1 or SEQ ID NO:2).

In some cases, a multimeric polypeptide of the present disclosure comprises a first polypeptide and a second polypeptide, where the first polypeptide comprises, in order from amino terminus (N-terminus) to carboxyl terminus (C-terminus): a) an epitope (e.g., a T-cell epitope); b) a first major histocompatibility complex (MHC) polypeptide and c) an immunomodulatory polypeptide (e.g., a variant PD-L1 polypeptide of the present disclosure); and where the second polypeptide comprises, in order from N-terminus to C-terminus: a) a second MHC polypeptide; and b) an immunoglobulin (Ig) Fc polypeptide. In other cases, a multimeric polypeptide of the present disclosure comprises a first polypeptide and a second polypeptide, where the first polypeptide comprises, in order from N-terminus to C-terminus: a) an epitope (e.g., a T-cell epitope); and b) a first MHC polypeptide; and where the second polypeptide comprises, in order from N-terminus to C-terminus: a) an immunomodulatory polypeptide (e.g., a variant PD-L1 polypeptide of the present disclosure); b) a second MHC polypeptide; and c) an Ig Fc polypeptide. In some instances, the first and the second MHC polypeptides are Class I MHC polypeptides; e.g., in some cases, the first MHC polypeptide is an MHC Class I β2-microglobulin (B2M or β2M) polypeptide, and the second MHC polypeptide is an MHC Class I heavy chain (H chain); or the first MHC polypeptide is an MHC Class I H chain, and the second MHC polypeptide is an MHC Class I β2M polypeptide). In other cases, the first and the second MHC polypeptides are Class II MHC polypeptides; e.g., in some cases, the first MHC polypeptide is an MHC Class II α-chain polypeptide, and the second MHC polypeptide is an MHC Class II β-chain polypeptide. In other cases, the first polypeptide is an MHC Class II β-chain polypeptide, and the second MHC polypeptide is an MHC Class II α-chain polypeptide. In some cases, a multimeric polypeptide of the present disclosure includes two or more variant PD-L1 immunomodulatory polypeptides of the present disclosure. Where a multimeric polypeptide of the present disclosure includes two or more immunomodulatory polypeptides, in some cases, the two or more immunomodulatory polypeptides are present in the same polypeptide chain, and may be in tandem. Where a multimeric polypeptide of the present disclosure includes two or more immunomodulatory polypeptides, in some cases, the two or more variant PD-L1 immunomodulatory polypeptides comprise the same amino acid sequence as one another. Where a multimeric polypeptide of the present disclosure includes two or more variant PD-L1 immunomodulatory polypeptides, in some cases, the two or more variant PD-L1 immunomodulatory polypeptides are present in separate polypeptides. In some cases, a multimeric polypeptide of the present disclosure is a heterodimer. In some cases, a multimeric polypeptide of the present disclosure is a trimeric polypeptide.

In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an Ig Fc polypeptide; and iii) an immunomodulatory domain (e.g., a variant PD-L1 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an immunomodulatory domain (e.g., a variant PD-L1 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain (e.g., a variant PD-L1 polypeptide of the present disclosure); and ii) a second MHC polypeptide. In some cases, a multimeric polypeptide of the present disclosure comprises: a) a first polypeptide comprising, in order from N-terminus to C-terminus: i) an epitope; ii) a first MHC polypeptide; and iii) an immunomodulatory domain (e.g., a variant PD-L1 polypeptide of the present disclosure); and b) a second polypeptide comprising, in order from N-terminus to C-terminus: i) a second MHC polypeptide. In some cases, where a multimeric polypeptide of the present disclosure comprises a non-Ig scaffold, the non-Ig scaffold is an XTEN peptide, a transferrin polypeptide, an Fc receptor polypeptide, an elastin-like polypeptide, a silk-like polypeptide, or a silk-elastin-like polypeptide.

In some cases, a multimeric polypeptide of the present disclosure is monovalent. In some cases, a multimeric polypeptide of the present disclosure is multivalent. In some cases, a multivalent multimeric polypeptide of the present disclosure comprises an immunoglobulin Fc polypeptide on one of the first or the second polypeptide. For example, depending on the Fc polypeptide present in a multimeric polypeptide of the present disclosure, the multimeric polypeptide can be a homodimer, where two molecules of the multimeric polypeptide are present in the homodimer, where the two molecules of the multimeric polypeptide can be disulfide linked to one another, e.g., via the Fc polypeptide present in the two molecules. As another example, a multimeric polypeptide of the present disclosure can comprise three, four, or five molecules of the multimeric polypeptide, where the molecules of the multimeric polypeptide can be disulfide linked to one another, e.g., via the Fc polypeptide present in the molecules.

In some cases, a multimeric polypeptide of the present disclosure comprises: a) a first polypeptide comprising, in order from N-terminus to C-terminus: i) an epitope; ii) a β2M polypeptide; and iii) a variant PD-L1 polypeptide of the present disclosure; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant PD-L1 polypeptide of the present disclosure; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant PD-L1 polypeptide of the present disclosure; iv) a second variant PD-L1 polypeptide of the present disclosure; and v) a third variant PD-L1 polypeptide of the present disclosure; and b) a second polypeptide comprising, in order from N-terminus to C-terminus: i) a Class I MHC heavy chain; and ii) an Fc polypeptide. In some cases, the first, second, and third variant PD-L1 polypeptides have the same amino acid sequence. In some cases, the first, second, and third variant PD-L1 polypeptides differ from one another in amino acid sequence. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a second variant PD-L1 polypeptide of the present disclosure; and iii) a third variant PD-L1 polypeptide of the present disclosure; iv) a Class I MHC heavy chain; and v) an Fc polypeptide. In some cases, the first, second, and third variant PD-L1 polypeptides have the same amino acid sequence. In some cases, the first, second, and third variant PD-L1 polypeptides differ from one another in amino acid sequence.

Linkers

A multimeric polypeptide of the present disclosure can include linker peptides interposed between, e.g., an epitope and an MHC polypeptide; between an MHC polypeptide and an immunomodulatory polypeptide; between an MHC polypeptide and an Ig Fc polypeptide; between a first variant PD-L1 polypeptide and a second variant PD-L1 polypeptide; or a between a second variant PD-L1 polypeptide and a third variant PD-L1 polypeptide.

Suitable linkers (also referred to as "spacers") can be readily selected and can be of any of a number of suitable lengths, such as from 1 amino acid to 25 amino acids, from 3 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids. A suitable linker can be 1, 2, 3, 4, 5, 6, 7, 8, 9, 10, 11, 12, 13, 14, 15, 16, 17, 18, 19, 20, 21, 22, 23, 24, or 25 amino acids in length.

Exemplary linkers include glycine polymers $(G)_n$, glycine-serine polymers (including, for example, $(GS)_n$, $(GSGGS)_n$, (SEQ ID NO:8) and $(GGGS)_n$ (SEQ ID NO:9), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)). Exemplary linkers can comprise amino acid sequences including, but not limited to, GGSG (SEQ ID NO:10), GGSGG (SEQ ID NO:11), GSGSG (SEQ ID NO:12), GSGGG (SEQ ID NO:13), GGGSG (SEQ ID NO:14), GSSSG (SEQ ID NO:15), and the like. Exemplary linkers can include, e.g., Gly($Ser_4$)n, where n is 1, 2, 3, 4, 5, 6, 7, 8, 9, or 10. In some cases, a linker comprises the amino acid sequence (GSSSS)n, where n is 4. In some cases, a linker comprises the amino acid sequence (GSSSS)n, where n is 5. Exemplary linkers can include, e.g., (($Gly_4$)Ser)n (SEQ ID NO:45), where n is 1, 2, 3, 4, 5, 6, 7, 8, 9, or 10. For example, in some cases, a linker comprises the amino acid sequence (GGGGS)n, where n is 4. In some cases, a linker comprises the amino acid sequence (GGGGS)n, where n is 5.

In some cases, a linker polypeptide, present in a first polypeptide of a multimeric polypeptide of the present disclosure, includes a cysteine residue that can form a disulfide bond with a cysteine residue present in a second polypeptide of a multimeric polypeptide of the present disclosure. In some cases, for example, a suitable linker comprises the amino acid sequence GCGA SGGGGSGGGGS (SEQ ID NO:16).

Epitopes

An epitope present in a multimeric polypeptide of the present disclosure can have a length of from about 4 amino acids to about 25 amino acids, e.g., the epitope can have a length of from 4 amino acids (aa) to 10 aa, from 10 aa to 15 aa, from 15 aa to 20 aa, or from 20 aa to 25 aa. For example, an epitope present in a multimeric polypeptide of the present disclosure can have a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, an epitope present in a multimeric polypeptide of the present disclosure has a length of from 5 amino acids to 10 amino acids, e.g., 5 aa, 6 aa, 7 aa, 8 aa, 9 aa, or 10 aa.

An epitope present in a multimeric polypeptide of the present disclosure is specifically bound by a T-cell, i.e., the epitope is specifically bound by an epitope-specific T cell. An epitope-specific T cell binds an epitope having a reference amino acid sequence, but does not substantially bind an epitope that differs from the reference amino acid sequence. For example, an epitope-specific T cell binds an epitope having a reference amino acid sequence, and binds an epitope that differs from the reference amino acid sequence, if at all, with an affinity that is less than $10^{-6}$ M, less than $10^{-5}$ M, or less than $10^{-4}$ M. An epitope-specific T cell can bind an epitope for which it is specific with an affinity of at least $10^{-7}$ M, at least $10^{-8}$ M, at least $10^{-9}$ M, or at least $10^{-10}$ M.

Suitable epitopes include, but are not limited to, epitopes present in an autoimmune-associated antigen. Autoimmune antigens include, but are not limited to, myelin basic protein (MBP); proteolipid protein (PLP); myelin oligodendrocyte glycoprotein (MOG), myelin-associated oligodendrocytic basic protein cardiac myosin; outer surface protein (OSP); myelin associated glycoprotein (MAG); neurofilaments; interferon omega; transglutaminase; aromatic acid carboxylase; 17-hydroxylase; 21-hydroxylase, cardiolipin; pyruvate dehydrogenase; β2 glycoprotein I; phosphatidylserine; apoH; Annexin A5; LKM-1; soluble liver antigen; carbonic anhydrase; gpIIb-IIIa or Ib-IX; type XVII collagen; tissue transglutaminase; gliadin; GD1a; GQ1b; BP-1; BP-2; epidermal transglutaminase; histidine-tRNA; signal recognition peptide; Mi-2; Jol; Glutamic acid decarboxylase, HSP60; HSP70; HSP90; IGRP; insulin; carboxypeptidase H; insulinoma antigen-2; IA-2beta; ICA69; ZnT8; chromogranin A; IAPP; sc170; topoisomerase; histones; Basement Membrane Collagen Type IV; enolase; thyroid peroxidase; thyroglobulin; complement component 3; voltage-gated calcium channels; Q-type calcium channel, synaptogagmin, muscarinic acetylcholine receptor Ml; SMA; LKM-1; LKM-2; LKM-3; soluble liver antigen; SLA; LP; major peripheral myelin protein P0; myeloperoxidase; GQ1b; U1-RNP; Kir4.1; nicotinic acetylcholine receptor; MuSK protein; hypocretin; orexin; keratin; AQP4; Yo; Hu; glutamate receptor; Desmoglein 3; p62; sp100, Ro; LA; glycoproteins IIb-IIIa or Ib-IX; ADAMTS13; cardiolipin; β2 glycoprotein I; HPA-1a; HPA-5b; IFN-gamma, IL-1, TNF-alpha; and GMCSF. Autoimmune antigens also include autoantigens relevant in type 1 diabetes, multiple sclerosis, or systemic lupus erythematosus. Pancreatic beta cell antigen islet-specific glucose-6-phosphatase catalytic subunit-related protein (IGRP) peptide known as $IGRP_{206-214}$ can be used as an autoimmune epitope, e.g., in the context of type 1 diabetes; the amino acid sequence of $IGRP_{206-214}$ is VYLKTNVFL (SEQ ID NO:43) (see, e.g., Krishnamurthy et al. (2008) *J. Immunol.* 180:4458; and Han et al. (2005) *J. Clin. Invest.* 115:1879). Other suitable IGRP peptides are disclosed in, e.g., Jarchum et al. (2008) *Clin. Immunol.* 127:359. Suitable autoantigen epitopes in the context of type 1 diabetes include peptide epitopes of preproinsulin; for example ALWGPDPAAA (SEQ ID NO:44) (see, e.g., Skowera et al. (2008) *J Clin. Invest.* 118:3390).

Autoimmune antigens and associated autoimmune disorders include, for example, myelin basic protein (MBP), proteolipid protein (PLP), and myelin oligodendrocyte glycoprotein (MOG), in each case associated with multiple sclerosis (MS); CD44, preproinsulin, proinsulin, insulin, glutamic acid decaroxylase (GAD65), tyrosine phosphatase-like insulinoma antigen 2 (IA2), zinc transporter ((ZnT8), and heat shock protein 60 (HSP60), in each case associated with diabetes Type I; interphotoreceptor retinoid-binding protein (IRBP) associated with autoimmune uveitis; acetylcholine receptor AchR, and insulin-like growth factor-1 receptor (IGF-1R), in each case associated with Myasthenia gravis; M-protein from beta-hemolytic streptocci (pseudo-autoantigen) associated with Rheumatic Fever; Macrophage migration inhibitory factor associated with Arthritis; Ro/La RNP complex, alpha- and beta-fodrin, islet cell autoantigen, poly(ADP)ribose polymerase (PARP), NuMA, NOR-90, Ro60 autoantigen, and p27 antigen, in each case associated with Sjogren's syndrome; Ro60 autoantigen, low-density lipoproteins, Sm antigens of the U-1 small nuclear ribonucleoprotein complex (B/B', D1, D2, D3, E, F, G), and RNP ribonucleoproteins, in each case associated with lupus erythematosus; oxLDL, beta(2)GPI, HSP60/65, and oxLDL/beta(2)GPI, in each case associated with Atherosclerosis; cardiac beta(1)-adrenergic receptor associated with idiopathic dilated cardiomyopathy (DCM); histidyl-tRNA synthetase (HisRS) associated with myositis; topoisomerase I associated with scleroderma; IL-17; or heat shock proteins.

MHC Polypeptides

As noted above, a multimeric polypeptide of the present disclosure includes MHC polypeptides. For the purposes of the instant disclosure, the term "major histocompatibility complex (MHC) polypeptides" is meant to include MHC polypeptides of various species, including human MHC (also referred to as human leukocyte antigen (HLA)) polypeptides, rodent (e.g., mouse, rat, etc.) MHC polypeptides, and MHC polypeptides of other mammalian species (e.g., lagomorphs (e.g., rabbits), non-human primates, canines (e.g., dogs), felines (e.g., cats), ungulates (e.g., equines, bovines, ovines, caprines, camels, etc.), and the like. The term "MHC polypeptide" is meant to include Class I MHC polypeptides (e.g., β-2 microglobulin and MHC class I heavy chain) and MHC Class II polypeptides (e.g., MHC Class II a polypeptide and MHC Class II β polypeptide).

As noted above, in some embodiments of a multimeric polypeptide of the present disclosure, the first and the second MHC polypeptides are Class I MHC polypeptides; e.g., in some cases, the first MHC polypeptide is an MHC Class I β2-microglobulin (β2M) polypeptide, and the second MHC polypeptide is an MHC Class I heavy chain (H chain). In other cases, the first and the second MHC polypeptides are Class II MHC polypeptides; e.g., in some cases, the first MHC polypeptide is an MHC Class II α-chain polypeptide, and the second MHC polypeptide is an MHC Class II β-chain polypeptide. In other cases, the first polypeptide is an MHC Class II β-chain polypeptide, and the second MHC polypeptide is an MHC Class II α-chain polypeptide.

In some cases, an MHC polypeptide of a multimeric polypeptide of the present disclosure is a human MHC polypeptide, where human MHC polypeptides are also referred to as "human leukocyte antigen" ("HLA") polypeptides. In some cases, an MHC polypeptide of a multimeric polypeptide of the present disclosure is a Class I HLA polypeptide, e.g., a β2-microglobulin polypeptide, or a Class I HLA heavy chain polypeptide. Class I HLA heavy chain polypeptides include HLA-A heavy chain polypeptides, HLA-B heavy chain polypeptides, HLA-C heavy chain polypeptides, HLA-E heavy chain polypeptides, HLA-F heavy chain polypeptides, and HLA-G heavy chain polypeptides. In some cases, an MHC polypeptide of a multimeric polypeptide of the present disclosure is a Class II HLA polypeptide, e.g., a Class II HLA α chain or a Class II HLA β chain. MHC Class II polypeptides include MCH Class II DP α and β polypeptides, DM α and β polypeptides, DOA α and β polypeptides, DOB α and β polypeptides, DQ α and β polypeptides, and DR α and β polypeptides.

As an example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the human HLA-A heavy chain polypeptide depicted in FIG. 5A.

As an example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the following human HLA-A heavy chain amino acid sequence:

```
                                        (SEQ ID NO: 17)
GSHSMRYFFTSVSRPGRGEPRFIAVGYVDDTQFVRFDSDAASQRMEP

RAPWIEQEGPEYWDGETRKVKAHSQTHRVDLGTLRGYYNQSEAGSHT

VQRMYGCDVGSDWRFLRGYHQYAYDGKDYIALKEDLRSWTAADMAAQ

TTKHKWEAAHVAEQLRAYLEGTCVEWLRRYLENGKETLQRTDAPKTH

MTHHAVSDHEATLRCWALSFYPAEITLTWQRDGEDQTQDTELVETRP

AGDGTFQKWAAVVVPSGQEQRYTCHVQHEGLPKPLTLRWEP.
```

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-B heavy chain polypeptide depicted in FIG. 5B.

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-C heavy chain polypeptide depicted in FIG. 5C.

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to the following amino acid sequence:

```
                                        (SEQ ID NO: 18)
GPHSLRYFVTAVSRPGLGEPRFIAVGYVDDTQFVRFDSDADNPRFEP

RAPWMEQEGPEYWEEQTQRAKSDEQWFRVSLRTAQRYYNQSKGGSHT

FQRMFGCDVGSDWRLLRGYQQFAYDGRDYIALNEDLKTWTAADTAAL

ITRRKWEQAGDAEYYRAYLEGECVEWLRRYLELGNETLLRTDSPKAH

VTYHPRSQVDVTLRCWALGFYPADITLTWQLNGEDLTQDMELVETRP

AGDGTFQKWAAVVVPLGKEQNYTCHVHHKGLPEPLTLRW.
```

A β2-microglobulin (β2M) polypeptide of a multimeric polypeptide of the present disclosure can be a human β2M polypeptide, a non-human primate β2M polypeptide, a murine β2M polypeptide, and the like. In some instances, a β2M polypeptide comprises an amino acid sequence having at least 75%, at least 80%, at least 85%, at least 90%, at least 95%, at least 98%, at least 99%, or 100%, amino acid sequence identity to a β2M amino acid sequence depicted in FIG. 6. In some instances, a β2M polypeptide comprises an amino acid sequence having at least 75%, at least 80%, at least 85%, at least 90%, at least 95%, at least 98%, at least 99%, or 100%, amino acid sequence identity to amino acids 21 to 119 of a β2M amino acid sequence depicted in FIG. 6.

In some cases, an MHC polypeptide comprises a single amino acid substitution relative to a reference MHC polypeptide (where a reference MHC polypeptide can be a wild-type MHC polypeptide), where the single amino acid substitution substitutes an amino acid with a cysteine (Cys) residue. Such cysteine residues, when present in an MHC polypeptide of a first polypeptide of a multimeric polypeptide of the present disclosure, can form a disulfide bond with a cysteine residue present in a second polypeptide chain of a multimeric polypeptide of the present disclosure.

In some cases, a first MHC polypeptide in a first polypeptide of a multimeric polypeptide of the present disclosure, and/or the second MHC polypeptide in the second polypeptide of a multimeric polypeptide of the present disclosure, includes an amino acid substitution to substitute an amino acid with a cysteine, where the substituted cysteine in the first MHC polypeptide forms a disulfide bond with a cysteine in the second MHC polypeptide, where a cysteine in the first MHC polypeptide forms a disulfide bond with the substituted cysteine in the second MHC polypeptide, or where the substituted cysteine in the first MHC polypeptide forms a disulfide bond with the substituted cysteine in the second MHC polypeptide.

For example, in some cases, one of following pairs of residues in an HLA β2-microglobulin and an HLA Class I heavy chain is substituted with cysteines (where residue numbers are those of the mature polypeptide): 1) β2M residue 12, HLA Class I heavy chain residue 236; 2) β2M residue 12, HLA Class I heavy chain residue 237; 3) β2M residue 8, HLA Class I heavy chain residue 234; 4) β2M residue 10, HLA Class I heavy chain residue 235; 5) β2M residue 24, HLA Class I heavy chain residue 236; 6) β2M residue 28, HLA Class I heavy chain residue 232; 7) β2M residue 98, HLA Class I heavy chain residue 192; 8) β2M residue 99, HLA Class I heavy chain residue 234; 9) β2M residue 3, HLA Class I heavy chain residue 120; 10) β2M residue 31, HLA Class I heavy chain residue 96; 11) β2M residue 53, HLA Class I heavy chain residue 35; 12) β2M residue 60, HLA Class I heavy chain residue 96; 13) β2M residue 60, HLA Class I heavy chain residue 122; 14) β2M residue 63, HLA Class I heavy chain residue 27; 15) β2M residue Arg3, HLA Class I heavy chain residue Gly 120; 16) β2M residue His31, HLA Class I heavy chain residue Gln96; 17) β2M residue Asp53, HLA Class I heavy chain residue Arg35; 18) β2M residue Trp60, HLA Class I heavy chain residue Gln96; 19) β2M residue Trp60, HLA Class I heavy chain residue Asp122; 20) β2M residue Tyr63, HLA Class I heavy chain residue Tyr27; 21) β2M residue Lys6, HLA Class I heavy chain residue Glu232; 22) β2M residue Gln8, HLA Class I heavy chain residue Arg234; 23) β2M residue Tyr10, HLA Class I heavy chain residue Pro235; 24) β2M residue Ser11, HLA Class I heavy chain residue Gln242; 25) β2M residue Asn24, HLA Class I heavy chain residue Ala236; 26) β2M residue Ser28, HLA Class I heavy chain residue Glu232; 27) β2M residue Asp98, HLA Class I heavy chain residue His192; and 28) β2M residue Met99, HLA Class I heavy chain residue Arg234. The amino acid numbering of the MHC/HLA Class I heavy chain is in reference to the mature MHC/HLA Class I heavy chain, without a signal peptide. For example, in the amino acid sequence depicted in FIG. 5A, which includes a signal peptide, Gly 120 is Gly 144; Gln96 is Gln120; etc. In some cases, the β2M polypeptide comprises an R12C substitution, and the HLA Class I heavy chain comprises an A236C substitution; in such cases, a disulfide bond forms between Cys-12 of the β2M polypeptide and Cys-236 of the HLA Class I heavy chain. For example, in some cases, residue 236 of the mature HLA-A amino acid sequence (i.e., residue 260 of the amino acid sequence depicted in FIG. 5A) is substituted with a Cys. In some cases, residue 236 of the mature HLA-B amino acid sequence (i.e., residue 260 of the amino acid sequence depicted in FIG. 5B) is substituted with a Cys. In some cases, residue 236 of the mature HLA-C amino acid sequence (i.e., residue 260 of the amino acid sequence depicted in FIG. 5C) is substituted with a Cys. In some cases, residue 32 (corresponding to Arg-12 of mature β2M) of an amino acid sequence depicted in FIG. 6 is substituted with a Cys.

In some cases, a β2M polypeptide comprises the amino acid sequence: IQRTPKIQVY SRHPAENGKS NFLNCYVSGF HPSDIEVDLLKNGERIEKVE HSDLSFSKDW SFYLLYYTEF TPTEKDEYAC RVNHVTLSQP KIVKWDRDM. In some cases, a β2M polypeptide comprises the amino acid sequence: IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM.

In some cases, an HLA Class I heavy chain polypeptide comprises the amino acid sequence:

```
                                            (SEQ ID NO: 19)
GSHSMRYFFTSVSRPGRGEPRFIAVGYVDDTQFVRFDSDAASQRMEP
RAPWIEQEGPEYWDGETRKVKAHSQTHRVDLGTLRGYYNQSEAGSHT
VQRMYGCDVGSDWRFLRGYHQYAYDGKDYIALKEDLRSWTAADMAAQ
TTKHKWEAAHVAEQLRAYLEGTCVEWLRRYLENGKETLQRTDAPKTH
MTHHAVSDHEATLRCWALSFYPAEITLTWQRDGEDQTQDTELVETRP
AGDGTFQKWAAVVVPSGQEQRYTCHVQHEGLPKPLTLRWEP.
```

In some cases, an HLA Class I heavy chain polypeptide comprises the amino acid sequence:

```
                                            (SEQ ID NO: 20)
GSHSMRYFFTSVSRPGRGEPRFIAVGYVDDTQFVRFDSDAASQRMEP
RAPWIEQEGPEYWDGETRKVKAHSQTHRVDLGTLRGYYNQSEAGSHT
VQRMYGCDVGSDWRFLRGYHQYAYDGKDYIALKEDLRSWTAADMAAQ
TTKHKWEAAHVAEQLRAYLEGTCVEWLRRYLENGKETLQRTDAPKTH
MTHHAVSDHEATLRCWALSFYPAEITLTWQRDGEDQTQDTELVETRP
CGDGTFQKWAAVVVPSGQEQRYTCHVQHEGLPKPLTLRWEP.
```

In some cases, the β2M polypeptide comprises the following amino acid sequence:

IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:42); and the HLA Class I heavy chain polypeptide of a multimeric polypeptide of the present disclosure comprises the following amino acid sequence:

GSHSMRYFFTSVSRPGRGEPRFIA-VGYVDDTQFVRFDSDAASQRMEPRAPWIE QEG-PEYWDGETRKVKAHSQTHRVDLGTLRGYYNQSEA-GSHTVQRMYGCDVGSDWR FLRGYHQYAYDGKDYIALKEDLRSWTAAD-MAAQTTKHKWEAAHVAEQLRAYLEGT CVEWLRRY-LENGKETLQRTDAPKTHMTHHAVSDHEATLRCW-ALSFYPAEITLTWQRD GEDQTQDTELVETRP CGDGTFQKWAAVVVPSGQEQRYTCHVQHEGLPKPL-TLRWEP (SEQ ID NO:21), where the Cys residues that are underlined and in bold form a disulfide bond with one another in the multimeric polypeptide.

Immunomodulatory Polypeptides

A multimeric polypeptide of the present disclosure comprises a variant PD-L1 polypeptide, as described above. Thus, a multimeric polypeptide of the present disclosure comprises the variant PD-L1 polypeptide present in the first polypeptide or the second polypeptide of a multimeric polypeptide of the present disclosure.

D26 Substitution

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is an amino acid other than an aspartic acid, e.g., where amino acid 26 is Gly, Ala, Val, Leu, Ile, Pro, Phe, Tyr, Trp, Ser, Thr, Cys, Met, Asn, Gln, Lys, Arg, His, or Glu. In some cases, the variant PD-L1 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 26 is Ala, Gly, Val, Leu, or Ile. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is Ala, Gly, Val, Leu, Ile, or Arg. In some cases, a variant PD-L1 polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is Ala. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is Gly. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is Val. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is Leu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is Ile. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is Arg. In some cases, a multimeric polypeptide of the present disclosure exhibits from about 40% to about 60% reduced binding affinity to PD-1 (e.g., to a PD-1 polypeptide comprising the amino acid sequence depicted in FIG. 3B), compared to the binding affinity of control multimeric polypeptide comprising a PD-L1 polypeptide comprising the amino acid sequence set forth in FIG. 2B (or set forth in SEQ ID NO:2) for the PD-1 polypeptide; and retains at least 80%, at least 85%, at least 90%, at least 95%, at least 98%, or at least 99%, of the binding affinity of a control multimeric polypeptide comprising a wild-type PD-L1 polypeptide (e.g., a PD-L1 polypeptide comprising the amino acid sequence set forth in FIG. 2B or SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises the amino acid sequence set forth in FIG. 2B, with an amino acid substitution at D26. In some cases, the variant PD-L1 polypeptide present in a multimeric polypeptide of the present disclosure comprises the amino acid sequence set forth in SEQ ID NO:2, with an amino acid substitution at D8. For example, in some cases, the variant PD-L1 polypeptide present in a multimeric polypeptide of the present disclosure comprises the amino acid sequence set forth in FIG. 2B, where amino acid 26 is any amino acid other than aspartic acid; for example, amino acid 26 can be Gly, Ala, Val, Leu, Ile, Pro, Phe, Tyr, Trp, Ser, Thr, Cys, Met, Asn, Gln, Lys, Arg, His, or Glu. In some cases, the variant PD-L1 polypeptide present in a multimeric polypeptide of the present disclosure comprises the amino acid sequence set forth in FIG. 2B, where amino acid 26 is Ala, Gly, Val, Leu, or Ile instead of Asp. In some cases, the variant PD-L1 polypeptide present in a multimeric polypeptide of the present disclosure comprises the amino acid sequence set forth in FIG. 2B, where amino acid 26 is Ala, Gly, Val, Leu, Ile, or Arg, instead of Asp. In some cases, the variant PD-L1 polypeptide present in a multimeric polypeptide of the present disclosure comprises the amino acid sequence set forth in FIG. 2B, where amino acid 26 is Ala instead of Asp. In some cases, the variant PD-L1 polypeptide present in a multimeric polypeptide of the present disclosure comprises the amino acid sequence set forth in FIG. 2B, where amino acid 26 is Val instead of Asp. In some cases, the variant PD-L1 polypeptide present in a multimeric polypeptide of the present disclosure comprises the amino acid sequence set forth in FIG. 2B, where amino acid 26 is Leu instead of Asp. In some cases, the variant PD-L1 polypeptide present in a multimeric polypeptide of the present disclosure comprises the amino acid sequence set forth in FIG. 2B, where amino acid 26 is Gly instead of Asp. In some cases, the variant PD-L1 polypeptide present in a multimeric polypeptide of the present disclosure comprises the amino acid sequence set forth in FIG. 2B, where amino acid 26 is Ile instead of Asp. In some cases, the variant PD-L1 polypeptide present in a multimeric polypeptide of the present disclosure comprises the amino acid sequence set forth in FIG. 2B, where amino acid 26 is Arg instead of Asp.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at D8; i.e., where amino acid 8 is other than an aspartic acid. For example, in some cases, the variant PD-L1 polypeptide present in a multimeric polypeptide of the present disclosure comprises the amino acid sequence set forth in SEQ ID NO:2, where amino acid 8 is any amino acid other than aspartic acid; for example, amino acid 8 can be Gly, Ala, Val, Leu, Ile, Pro, Phe, Tyr, Trp, Ser, Thr, Cys, Met, Asn, Gln, Lys, Arg, His, or Glu. In some cases, the variant PD-L1 polypeptide present in a multimeric polypeptide of the present disclosure comprises the amino acid sequence set forth in SEQ ID NO:2, where amino acid 8 is Ala, Gly, Val, Leu, or Ile instead of Asp. In some cases, the variant PD-L1 polypeptide present in a multimeric polypeptide of the present disclosure comprises the amino acid sequence set forth in SEQ ID NO:2, where amino acid 8 is Ala, Gly, Val, Leu, Ile, or Arg instead of Asp. In some cases, the variant PD-L1 polypeptide present in a multimeric polypeptide of the present disclosure comprises the amino acid sequence set forth in SEQ ID NO:2, where amino acid 8 is Ala instead of Asp. In some cases, the variant PD-L1 polypeptide present in a multimeric polypeptide of the present disclosure comprises the amino acid sequence set forth in SEQ ID NO:2, where amino acid 8 is Val instead of Asp. In some cases, the variant PD-L1 polypeptide present in a multimeric polypeptide of the present disclosure comprises the amino acid sequence set forth in SEQ ID NO:2, where amino acid 8 is Leu instead of Asp. In some cases, the variant PD-L1 polypeptide present in a multimeric polypeptide of the present disclosure comprises the amino acid sequence set forth in SEQ ID NO:2, where amino acid 8 is Gly instead of Asp. In some cases, the variant PD-L1 polypeptide present in a multimeric polypeptide of the present disclosure comprises the amino acid sequence set forth in SEQ ID NO:2, where amino acid 8 is Ile. In some cases, a variant PD-L1 polypeptide of the present disclosure comprises the amino acid sequence set forth in SEQ ID NO:2, where amino acid 8 is Arg instead of Asp.

In some cases, the variant PD-L1 polypeptide present in a multimeric polypeptide of the present disclosure comprises the amino acid sequence depicted in FIG. 2D. In some cases, the variant PD-L1 polypeptide present in a multimeric polypeptide of the present disclosure comprises the amino acid sequence depicted in FIG. 2E. In some cases, the variant PD-L1 polypeptide present in a multimeric polypeptide of the present disclosure comprises the amino acid sequence depicted in FIG. 2F. In some cases, the variant PD-L1 polypeptide present in a multimeric polypeptide of the present disclosure comprises the amino acid sequence depicted in FIG. 2G.

T37 Substitution

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is an amino acid other than threonine, e.g., where amino acid 37 is Gly, Ala, Val, Leu, Ile, Pro, Phe, Tyr, Trp, Ser, Cys, Met, Asn, Gln, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Gly, Ala, Val, Leu, Ile, Arg, Lys, or His. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Arg, Lys, or His. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Gly, Ala, Val, Leu, or Ile. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Arg. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Lys. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is His. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Gly. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Ala. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Val. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Leu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is Ile. In some cases, a multimeric polypeptide of the present disclosure exhibits from about 15% to about 35% of the binding affinity to PD-1 (e.g., to a PD-1 polypeptide comprising the amino acid sequence depicted in FIG. 3B) exhibited by a control multimeric polypeptide comprising a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 70% to about 90% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises the amino acid sequence set forth in FIG. 2B, with an amino acid substitution at T37. In some cases, the variant PD-L1 polypeptide present in a multimeric polypeptide of the present disclosure comprises the amino acid sequence set forth in SEQ ID NO:2, with an amino acid substitution at T19. For example, in some cases, the variant PD-L1 polypeptide present in a multimeric polypeptide of the present disclosure comprises the amino acid sequence set forth in FIG. 2B, where amino acid 37 is any amino acid other than threonine; for example, amino acid 37 can be Gly, Ala, Val, Leu, Ile, Pro, Phe, Tyr, Trp, Ser, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2B, where amino acid 37 is Gly, Ala, Val, Leu, Ile, Arg, His, or Lys, instead of Thr. In some cases, the variant PD-L1 polypeptide present in a multimeric polypeptide of the present disclosure comprises the amino acid sequence set forth in FIG. 2B, where amino acid 37 is Gly, Ala, Val, Leu, or Ile, instead of Thr. In some cases, the variant PD-L1 polypeptide present in a multimeric polypeptide of the present disclosure comprises the amino acid sequence set forth in FIG. 2B, where amino acid 37 is Arg, His, or Lys, instead of Thr. In some cases, the variant PD-L1 polypeptide present in a multimeric polypeptide of the present disclosure comprises the amino acid sequence set forth in FIG. 2B, where amino acid 37 is Arg instead of Thr. In some cases, the variant PD-L1 polypeptide present in a multimeric polypeptide of the present disclosure comprises the amino acid sequence set forth in FIG. 2B, where amino acid 37 is Lys instead of Thr. In some cases, the variant PD-L1 polypeptide present in a multimeric polypeptide of the present disclosure comprises the amino acid sequence set forth in FIG. 2B, where amino acid 37 is His instead of Thr. In some cases, the variant PD-L1 polypeptide present in a multimeric polypeptide of the present disclosure comprises the amino acid sequence set forth in FIG. 2B, where amino acid 37 is Gly instead of Thr. In some cases, the variant PD-L1 polypeptide present in a multimeric polypeptide of the present disclosure comprises the amino acid sequence set forth in FIG. 2B, where amino acid 37 is Ala instead of Thr. In some cases, the variant PD-L1 polypeptide present in a multimeric polypeptide of the present disclosure comprises the amino acid sequence set forth in FIG. 2B, where amino acid 37 is Val instead of Thr. In some cases, the variant PD-L1 polypeptide present in a multimeric polypeptide of the present disclosure comprises the amino acid sequence set forth in FIG. 2B, where amino acid 37 is Leu instead of Thr. In some cases, the variant PD-L1 polypeptide present in a multimeric polypeptide of the present disclosure comprises the amino acid sequence set forth in FIG. 2B, where amino acid 37 is Ile instead of Thr.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at T19; i.e., where amino acid 19 is other than threonine. For example, in some cases, the variant PD-L1 polypeptide present in a multimeric polypeptide of the present disclosure comprises the amino acid sequence set forth in SEQ ID NO:2, where amino acid 19 is any amino acid other than threonine; for example, amino acid 19 can be Gly, Ala, Val, Leu, Ile, Pro, Phe, Tyr, Trp, Ser, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:2, where amino acid 19 is Gly, Ala, Val, Leu, Ile, Arg, His, or Lys instead of Thr. In some cases, the variant PD-L1 polypeptide present in a multimeric polypeptide of the present disclosure comprises the amino acid sequence set forth in SEQ ID NO:2, where amino acid 19 is Gly, Ala, Val, Leu, or Ile, instead of Thr. In some cases, the variant PD-L1 polypeptide present in a multimeric polypeptide of the present disclosure comprises the amino acid sequence set forth in SEQ ID NO:2, where amino acid 19 is Arg, His, or Lys instead of Thr. In some cases, the variant PD-L1 polypeptide present in a multimeric polypeptide of the present disclosure comprises the amino acid sequence set forth in SEQ ID NO:2, where amino acid 19 is Arg instead of Thr. In some cases, the variant PD-L1 polypeptide present in a multimeric polypeptide of the present disclosure comprises the amino acid sequence set forth in SEQ ID NO:2, where amino acid 19 is Lys instead of Thr. In some cases, the variant PD-L1 polypeptide present in a multimeric polypeptide of the present disclosure comprises the amino acid sequence set forth in SEQ ID NO:2, where amino acid 54 is His instead of 19. In some cases, the variant PD-L1 polypeptide present in a multimeric polypeptide of the present disclosure comprises the amino acid sequence set forth in SEQ ID NO:2, where amino acid 19 is Gly instead of Thr. In some cases, the variant PD-L1 polypeptide present in a multimeric polypeptide of the present disclosure comprises the amino acid sequence set forth in SEQ ID NO:2, where amino acid 19 is Ala instead of Thr. In some cases, the variant PD-L1 polypeptide present in a multimeric polypeptide of the present disclosure comprises the amino acid sequence set forth in SEQ ID NO:2, where amino acid 19 is Val instead of Thr. In some cases, the variant PD-L1 polypeptide present in a multimeric polypeptide of the present disclosure comprises the amino acid sequence set forth in SEQ ID NO:2, where amino acid 19 is Leu instead of Thr. In some cases, the variant PD-L1 polypeptide present in a multimeric polypeptide of the present disclosure comprises the amino acid sequence set forth in SEQ ID NO:2, where amino acid 19 is Ile instead of Thr.

I54 Substitution

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is an amino acid other than isoleucine, e.g., where amino acid 54 is Gly, Ala, Val, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is an amino acid other than isoleucine or valine, e.g., where amino acid 54 is Gly, Ala, Leu, Pro, Phe, Tyr, Trp, Ser, Thr, Cys, Met, Asn, Gin, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Ala, Gly, Leu, Glu, Arg, or Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Glu or Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Ala. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Gly. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Leu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 54 is Arg. In some cases, a multimeric polypeptide of the present disclosure exhibits from about 70% to about 100% of the binding affinity to PD-1 (e.g., to a PD-1 polypeptide comprising the amino acid sequence depicted in FIG. 2B) exhibited by a control multimeric polypeptide comprising a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 40% to about 90% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is an amino acid other than valine, e.g., where amino acid 54 is Gly, Ala, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is an amino acid other than isoleucine or valine, e.g., where amino acid 54 is Gly, Ala, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Ala, Gly, Leu, Glu, Arg, or Asp. I In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Glu or Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Ala. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Gly. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Leu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2A, where amino acid 54 is Arg. In some cases, a multimeric polypeptide of the present disclosure exhibits from about 70% to about 100% of the binding affinity to PD-1 (e.g., to a PD-1 polypeptide comprising the amino acid sequence depicted in FIG. 3A) exhibited by a control multimeric polypeptide comprising a PD-L1 polypeptide comprising the amino acid sequence set forth in FIG. 2A (or set forth in SEQ ID NO:1) for the PD-1 polypeptide; and exhibits reduced binding affinity to B7-1 (e.g., exhibits from about 40% to about 90% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 2A or in SEQ ID NO:1) for a wild-type B7-1 polypeptide (e.g., a B7-1 polypeptide comprising the amino acid sequence depicted in FIG. 3C).

In some cases, the variant PD-L1 polypeptide present in a multimeric polypeptide of the present disclosure comprises the amino acid sequence set forth in FIG. 2B, with an amino acid substitution at I54. In some cases, the variant PD-L1 polypeptide present in a multimeric polypeptide of the present disclosure comprises the amino acid sequence set forth in SEQ ID NO:2, with an amino acid substitution at I36. For example, in some cases, the variant PD-L1 polypeptide present in a multimeric polypeptide of the present disclosure comprises the amino acid sequence set forth in FIG. 2B, where amino acid 54 is any amino acid other than isoleucine; for example, amino acid 54 can be Gly, Ala, Val, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2B, where amino acid 54 is any amino acid other than isoleucine or valine; for example, amino acid 54 can be Gly, Ala, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2B, where amino acid 54 is Ala, Gly, Leu, Arg, or Asp, instead of Ile. In some cases, the variant PD-L1 polypeptide present in a multimeric polypeptide of the present disclosure comprises the amino acid sequence set forth in FIG. 2B, where amino acid 54 is Ala instead of Ile. In some cases, the variant PD-L1 polypeptide present in a multimeric polypeptide of the present disclosure comprises the amino acid sequence set forth in FIG. 2B, where amino acid 54 is Leu instead of Ile. In some cases, the variant PD-L1 polypeptide present in a multimeric polypeptide of the present disclosure comprises the amino acid sequence set forth in FIG. 2B, where amino acid 54 is Gly instead of Ile. In some cases, the variant PD-L1 polypeptide present in a multimeric polypeptide of the present disclosure comprises the amino acid sequence set forth in FIG. 2B, where amino acid 54 is Asp instead of Ile. In some cases, the variant PD-L1 polypeptide present in a multimeric polypeptide of the present disclosure comprises the amino acid sequence set forth in FIG. 2B, where amino acid 54 is Arg instead of Ile.

In some cases, the variant PD-L1 polypeptide present in a multimeric polypeptide of the present disclosure comprises the amino acid sequence set forth in FIG. 2A, with an amino acid substitution at V54. In some cases, the variant PD-L1 polypeptide present in a multimeric polypeptide of the present disclosure comprises the amino acid sequence set forth in SEQ ID NO:1, with an amino acid substitution at V36. For example, in some cases, the variant PD-L1 polypeptide present in a multimeric polypeptide of the present disclosure comprises the amino acid sequence set forth in FIG. 2A, where amino acid 54 is any amino acid other than valine; for example, amino acid 54 can be Gly, Ala, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2A, where amino acid 54 is any amino acid other than isoleucine or valine; for example, amino acid 54 can be Gly, Ala, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2A, where amino acid 54 is Ala, Gly, Leu, Glu, Arg, or Asp, instead of Val. In some cases, the variant PD-L1 polypeptide present in a multimeric polypeptide of the present disclosure comprises the amino acid sequence set forth in FIG. 2A, where amino acid 54 is Glu or Asp, instead of Val. In some cases, the variant PD-L1 polypeptide present in a multimeric polypeptide of the present disclosure comprises the amino acid sequence set forth in FIG. 2A, where amino acid 54 is Ala instead of Val. In some cases, the variant PD-L1 polypeptide present in a multimeric polypeptide of the present disclosure comprises the amino acid sequence set forth in FIG. 2A, where amino acid 54 is Leu instead of Val. In some cases, the variant PD-L1 polypeptide present in a multimeric polypeptide of the present disclosure comprises the amino acid sequence set forth in FIG. 2A, where amino acid 54 is Gly instead of Val. In some cases, the variant PD-L1 polypeptide present in a multimeric polypeptide of the present disclosure comprises the amino acid sequence set forth in FIG. 2A, where amino acid 54 is Asp instead of Val. In some cases, the variant PD-L1 polypeptide present in a multimeric polypeptide of the present disclosure comprises the amino acid sequence set forth in FIG. 2A, where amino acid 54 is Glu instead of Val. In some cases, the variant PD-L1 polypeptide present in a multimeric polypeptide of the present disclosure comprises the amino acid sequence set forth in FIG. 2A, where amino acid 54 is Arg instead of Val.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at Ile-36; i.e., where amino acid 36 is other than isoleucine. For example, in some cases, the variant PD-L1 polypeptide present in a multimeric polypeptide of the present disclosure comprises the amino acid sequence set forth in SEQ ID NO:2, where amino acid 36 is any amino acid other than isoleucine; for example, amino acid 36 can be Gly, Ala, Val, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:2, where amino acid 36 is any amino acid other than isoleucine or valine; for example, amino acid 36 can be Gly, Ala, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:2, where amino acid 36 is Ala, Gly, Leu, Arg, or Asp instead of Ile. In some cases, the variant PD-L1 polypeptide present in a multimeric polypeptide of the present disclosure comprises the amino acid sequence set forth in SEQ ID NO:2, where amino acid 36 is Ala instead of Ile. In some cases, the variant PD-L1 polypeptide present in a multimeric polypeptide of the present disclosure comprises the amino acid sequence set forth in SEQ ID NO:2, where amino acid 36 is Leu instead of Ile. In some cases, the variant PD-L1 polypeptide present in a multimeric polypeptide of the present disclosure comprises the amino acid sequence set forth in SEQ ID NO:2, where amino acid 36 is Gly instead of Ile. In some cases, the variant PD-L1 polypeptide present in a multimeric polypeptide of the present disclosure comprises the amino acid sequence set forth in SEQ ID NO:2, where amino acid 36 is Asp instead of Ile. In some cases, the variant PD-L1 polypeptide present in a multimeric polypeptide of the present disclosure comprises the amino acid sequence set forth in SEQ ID NO:2, where amino acid 36 is Arg instead of Ile.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:1, with an amino acid substitution at V36. For example, in some cases, the variant PD-L1 polypeptide present in a multimeric polypeptide of the present disclosure comprises the amino acid sequence set forth in SEQ ID NO:1, where amino acid 36 is any amino acid other than valine; for example, amino acid 36 can be Gly, Ala, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:1, where amino acid 36 is any amino acid other than isoleucine or valine; for example, amino acid 36 can be Gly, Ala, Leu, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:1, where amino acid 36 is Ala, Gly, Leu, Glu, or Asp instead of Val. In some cases, a variant PD-L1 polypeptide of the present disclosure comprises the amino acid sequence set forth in SEQ ID NO:1, where amino acid 36 is Glu or Asp instead of Val. In some cases, the variant PD-L1 polypeptide present in a multimeric polypeptide of the present disclosure comprises the amino acid sequence set forth in SEQ ID NO:1, where amino acid 36 is Ala instead of Val. In some cases, the variant PD-L1 polypeptide present in a multimeric polypeptide of the present disclosure comprises the amino acid sequence set forth in SEQ ID NO:1, where amino acid 36 is Leu instead of Val. In some cases, the variant PD-L1 polypeptide present in a multimeric polypeptide of the present disclosure comprises the amino acid sequence set forth in SEQ ID NO:1, where amino acid 36 is Gly instead of Val. In some cases, the variant PD-L1 polypeptide present in a multimeric polypeptide of the present disclosure comprises the amino acid sequence set forth in SEQ ID NO:1, where amino acid 36 is Asp instead of Val. In some cases, the variant PD-L1 polypeptide present in a multimeric polypeptide of the present disclosure comprises the amino acid sequence set forth in SEQ ID NO:1, where amino acid 36 is Glu instead of Val. In some cases, the variant PD-L1 polypeptide present in a multimeric polypeptide of the present disclosure comprises the amino acid sequence set forth in SEQ ID NO:1, where amino acid 36 is Arg instead of Val.

In some cases, the variant PD-L1 polypeptide present in a multimeric polypeptide of the present disclosure comprises the amino acid sequence depicted in FIG. 2H. In some cases, the variant PD-L1 polypeptide present in a multimeric polypeptide of the present disclosure comprises the amino acid sequence depicted in FIG. 2I.

Q66 Substitution

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 66 is an amino acid other than glutamine, e.g., where amino acid 66 is Gly, Ala, Val, Leu, Ile, Pro, Phe, Tyr, Trp, Ser, Thr, Cys, Met, Asn, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 66 is Glu or Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 66 is Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 66 is Asp. In some cases, a multimeric polypeptide of the present disclosure exhibits from about 80% to about 100% of the binding affinity to PD-1 (e.g., to a PD-1 polypeptide comprising the amino acid sequence depicted in FIG. 3B) exhibited by a control multimeric polypeptide comprising a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 40% to about 90% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises the amino acid sequence set forth in FIG. 2B, with an amino acid substitution at Q66. In some cases, the variant PD-L1 polypeptide present in a multimeric polypeptide of the present disclosure comprises the amino acid sequence set forth in SEQ ID NO:2, with an amino acid substitution at Q48. For example, in some cases, the variant PD-L1 polypeptide present in a multimeric polypeptide of the present disclosure comprises the amino acid sequence set forth in FIG. 2B, where amino acid 66 is any amino acid other than glutamine; for example, amino acid 66 can be Gly, Ala, Val, Leu, Ile, Pro, Phe, Tyr, Trp, Ser, Thr, Cys, Met, Asn, Lys, Arg, His, Asp, or Glu. In some cases, the variant PD-L1 polypeptide present in a multimeric polypeptide of the present disclosure comprises the amino acid sequence set forth in FIG. 2B, where amino acid 66 is Ala, Gly, Leu, Glu, or Asp, instead of Gln. In some cases, the variant PD-L1 polypeptide present in a multimeric polypeptide of the present disclosure comprises the amino acid sequence set forth in FIG. 2B, where amino acid 66 is Glu or Asp, instead of Gln. In some cases, the variant PD-L1 polypeptide present in a multimeric polypeptide of the present disclosure comprises the amino acid sequence set forth in FIG. 2B, where amino acid 66 is Ala instead of Gln. In some cases, the variant PD-L1 polypeptide present in a multimeric polypeptide of the present disclosure comprises the amino acid sequence set forth in FIG. 2B, where amino acid 66 is Leu instead of Gln. In some cases, the variant PD-L1 polypeptide present in a multimeric polypeptide of the present disclosure comprises the amino acid sequence set forth in FIG. 2B, where amino acid 66 is Gly instead of Gln. In some cases, the variant PD-L1 polypeptide present in a multimeric polypeptide of the present disclosure comprises the amino acid sequence set forth in FIG. 2B, where amino acid 66 is Asp instead of Gln. In some cases, the variant PD-L1 polypeptide present in a multimeric polypeptide of the present disclosure comprises the amino acid sequence set forth in FIG. 2B, where amino acid 66 is Glu instead of Gln.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at Q48; i.e., where amino acid 48 is other than glutamine. For example, in some cases, the variant PD-L1 polypeptide present in a multimeric polypeptide of the present disclosure comprises the amino acid sequence set forth in SEQ ID NO:2, where amino acid 48 is any amino acid other than glutamine; for example, amino acid 48 can be Gly, Ala, Val, Leu, Ile, Pro, Phe, Tyr, Trp, Ser, Thr, Cys, Met, Asn, Lys, Arg, His, Asp, or Glu. In some cases, the variant PD-L1 polypeptide present in a multimeric polypeptide of the present disclosure comprises the amino acid sequence set forth in SEQ ID NO:2, where amino acid 48 is Ala, Gly, Leu, Glu, or Asp instead of Gln. In some cases, the variant PD-L1 polypeptide present in a multimeric polypeptide of the present disclosure comprises the amino acid sequence set forth in SEQ ID NO:2, where amino acid 48 is Glu or Asp instead of Gln. In some cases, the variant PD-L1 polypeptide present in a multimeric polypeptide of the present disclosure comprises the amino acid sequence set forth in SEQ ID NO:2, where amino acid 48 is Ala instead of Gln. In some cases, the variant PD-L1 polypeptide present in a multimeric polypeptide of the present disclosure comprises the amino acid sequence set forth in SEQ ID NO:2, where amino acid 48 is Leu instead of Gln. In some cases, the variant PD-L1 polypeptide present in a multimeric polypeptide of the present disclosure comprises the amino acid sequence set forth in SEQ ID NO:2, where amino acid 48 is Gly instead of Gln. In some cases, the variant PD-L1 polypeptide present in a multimeric polypeptide of the present disclosure comprises the amino acid sequence set forth in SEQ ID NO:2, where amino acid 48 is Asp instead of Gln. In some cases, the variant PD-L1 polypeptide present in a multimeric polypeptide of the present disclosure comprises the amino acid sequence set forth in SEQ ID NO:2, where amino acid 48 is Glu instead of Gln.

In some cases, the variant PD-L1 polypeptide present in a multimeric polypeptide of the present disclosure comprises the amino acid sequence depicted in FIG. 2J. In some cases, the variant PD-L1 polypeptide present in a multimeric polypeptide of the present disclosure comprises the amino acid sequence depicted in FIG. 2K.

E72 Substitution

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 72 is an amino acid other than glutamic acid, e.g., where amino acid 72 is Gly, Ala, Val, Leu, Ile, Pro, Phe, Tyr, Trp, Ser, Thr, Cys, Met, Asn, Gln, Lys, Arg, His, or Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 72 is Arg, Lys, or His. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 72 is Asp, Arg, Lys, or His. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 72 is Arg. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 72 is Lys. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 72 is His. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 72 is Asp. In some cases, a multimeric polypeptide of the present disclosure exhibits from about 30% to about 60% of the binding affinity to PD-1 (e.g., to a PD-1 polypeptide comprising the amino acid sequence depicted in FIG. 3B) exhibited by a control multimeric polypeptide comprising a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 40% to about 90% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises the amino acid sequence set forth in FIG. 2B, with an amino acid substitution at E72. In some cases, the variant PD-L1 polypeptide present in a multimeric polypeptide of the present disclosure comprises the amino acid sequence set forth in SEQ ID NO:2, with an amino acid substitution at E54. For example, in some cases, the variant PD-L1 polypeptide present in a multimeric polypeptide of the present disclosure comprises the amino acid sequence set forth in FIG. 2B, where amino acid 72 is any amino acid other than glutamic acid; for example, amino acid 72 can be Gly, Ala, Val, Leu, Ile, Pro, Phe, Tyr, Trp, Ser, Thr, Cys, Met, Asn, Gln, Lys, Arg, His, or Asp. In some cases, the variant PD-L1 polypeptide present in a multimeric polypeptide of the present disclosure comprises the amino acid sequence set forth in FIG. 2B, where amino acid 72 is Asp, Arg, His, or Lys, instead of Glu. In some cases, the variant PD-L1 polypeptide present in a multimeric polypeptide of the present disclosure comprises the amino acid sequence set forth in FIG. 2B, where amino acid 72 is Arg, His, or Lys, instead of Glu. In some cases, the variant PD-L1 polypeptide present in a multimeric polypeptide of the present disclosure comprises the amino acid sequence set forth in FIG. 2B, where amino acid 72 is Arg instead of Glu. In some cases, the variant PD-L1 polypeptide present in a multimeric polypeptide of the present disclosure comprises the amino acid sequence set forth in FIG. 2B, where amino acid 72 is Lys instead of Glu. In some cases, the variant PD-L1 polypeptide present in a multimeric polypeptide of the present disclosure comprises the amino acid sequence set forth in FIG. 2B, where amino acid 72 is His instead of Glu. In some cases, the variant PD-L1 polypeptide present in a multimeric polypeptide of the present disclosure comprises the amino acid sequence set forth in FIG. 2B, where amino acid 72 is Asp instead of Glu.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at E54; i.e., where amino acid 54 is other than a glutamic acid. For example, in some cases, the variant PD-L1 polypeptide present in a multimeric polypeptide of the present disclosure comprises the amino acid sequence set forth in SEQ ID NO:2, where amino acid 54 is any amino acid other than glutamic acid; for example, amino acid 54 can be Gly, Ala, Val, Leu, Ile, Pro, Phe, Tyr, Trp, Ser, Thr, Cys, Met, Asn, Gln, Lys, Arg, His, or Asp. In some cases, the variant PD-L1 polypeptide present in a multimeric polypeptide of the present disclosure comprises the amino acid sequence set forth in SEQ ID NO:2, where amino acid 54 is Asp, Arg, His, or Lys instead of Glu. In some cases, the variant PD-L1 polypeptide present in a multimeric polypeptide of the present disclosure comprises the amino acid sequence set forth in SEQ ID NO:2, where amino acid 54 is Arg, His, or Lys instead of Glu. In some cases, the variant PD-L1 polypeptide present in a multimeric polypeptide of the present disclosure comprises the amino acid sequence set forth in SEQ ID NO:2, where amino acid 54 is Arg instead of Glu. In some cases, the variant PD-L1 polypeptide present in a multimeric polypeptide of the present disclosure comprises the amino acid sequence set forth in SEQ ID NO:2, where amino acid 54 is Lys instead of Glu. In some cases, the variant PD-L1 polypeptide present in a multimeric polypeptide of the present disclosure comprises the amino acid sequence set forth in SEQ ID NO:2, where amino acid 54 is His instead of Glu. In some cases, the variant PD-L1 polypeptide present in a multimeric polypeptide of the present disclosure comprises the amino acid sequence set forth in SEQ ID NO:2, where amino acid 54 is Asp instead of Glu.

In some cases, the variant PD-L1 polypeptide present in a multimeric polypeptide of the present disclosure comprises the amino acid sequence depicted in FIG. 2L. In some cases, the variant PD-L1 polypeptide present in a multimeric polypeptide of the present disclosure comprises the amino acid sequence depicted in FIG. 2M.

Y56

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is an amino acid other than tyrosine, e.g., where amino acid 56 is Gly, Ala, Val, Leu, Ile, Pro, Phe, Trp, Ser, Thr, Cys, Met, Asn, Gln, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is Ala, Gly, Val, Leu, or Ile. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is Asp or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is Arg, His, or Lys. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is Ala, Asp, or Arg. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is Arg. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is Ala. In some cases, a multimeric polypeptide of the present disclosure exhibits from about 50% to about 100% of the binding affinity to PD-1 (e.g., to a PD-1 polypeptide comprising the amino acid sequence depicted in FIG. 3B) exhibited by a control multimeric polypeptide comprising a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 60% to about 95% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises the amino acid sequence set forth in FIG. 2B, with an amino acid substitution at Y56. In some cases, the variant PD-L1 polypeptide present in a multimeric polypeptide of the present disclosure comprises the amino acid sequence set forth in SEQ ID NO:2, with an amino acid substitution at Y38. For example, in some cases, the variant PD-L1 polypeptide present in a multimeric polypeptide of the present disclosure comprises the amino acid sequence set forth in FIG. 2B, where amino acid 56 is any amino acid other than tyrosine; for example, amino acid 56 can be Gly, Ala, Val, Leu, Ile, Pro, Phe, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2B, where amino acid 56 is Ala, Val, Gly, Leu, or Ile, instead of Tyr. In some cases, the variant PD-L1 polypeptide present in a multimeric polypeptide of the present disclosure comprises the amino acid sequence set forth in FIG. 2B, where amino acid 56 is Arg, His, or Lys, instead of Tyr. In some cases, the variant PD-L1 polypeptide present in a multimeric polypeptide of the present disclosure comprises the amino acid sequence set forth in FIG. 2B, where amino acid 56 is Asp or Glu, instead of Tyr. In some cases, the variant PD-L1 polypeptide present in a multimeric polypeptide of the present disclosure comprises the amino acid sequence set forth in FIG. 2B, where amino acid 56 is Arg instead of Tyr. In some cases, the variant PD-L1 polypeptide present in a multimeric polypeptide of the present disclosure comprises the amino acid sequence set forth in FIG. 2B, where amino acid 56 is Asp instead of Tyr. In some cases, the variant PD-L1 polypeptide present in a multimeric polypeptide of the present disclosure comprises the amino acid sequence set forth in FIG. 2B, where amino acid 56 is Ala instead of Tyr.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at Y38; i.e., where amino acid 38 is other than tyrosine. For example, in some cases, the variant PD-L1 polypeptide present in a multimeric polypeptide of the present disclosure comprises the amino acid sequence set forth in SEQ ID NO:2, where amino acid 38 is any amino acid other than tyrosine; for example, amino acid 38 can be Gly, Ala, Val, Leu, Ile, Pro, Phe, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:2, where amino acid 38 is Arg, His, or Lys instead of Tyr. In some cases, the variant PD-L1 polypeptide present in a multimeric polypeptide of the present disclosure comprises the amino acid sequence set forth in SEQ ID NO:2, where amino acid 38 is Asp or Glu instead of Tyr. In some cases, the variant PD-L1 polypeptide present in a multimeric polypeptide of the present disclosure comprises the amino acid sequence set forth in SEQ ID NO:2, where amino acid 38 is Ala, Gly, Val, Leu, or Ile instead of Tyr. In some cases, the variant PD-L1 polypeptide present in a multimeric polypeptide of the present disclosure comprises the amino acid sequence set forth in SEQ ID NO:2, where amino acid 38 is Arg instead of Tyr. In some cases, the variant PD-L1 polypeptide present in a multimeric polypeptide of the present disclosure comprises the amino acid sequence set forth in SEQ ID NO:2, where amino acid 38 is Ala instead of Tyr. In some cases, the variant PD-L1 polypeptide present in a multimeric polypeptide of the present disclosure comprises the amino acid sequence set forth in SEQ ID NO:2, where amino acid 38 is Asp instead of Tyr.

G119

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is an amino acid other than glycine, e.g., where amino acid 119 is Ala, Val, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is Ala, Val, Leu, or Ile. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is Asp or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is Arg, His, or Lys. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is Arg. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is Ala. In some cases, a multimeric polypeptide of the present disclosure exhibits from about 20% to about 50%, or from about 50% to 100%, of the binding affinity to PD-1 (e.g., to a PD-1 polypeptide comprising the amino acid sequence depicted in FIG. 3B) exhibited by a control multimeric polypeptide comprising a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 60% to about 95% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises the amino acid sequence set forth in FIG. 2B, with an amino acid substitution at G119. In some cases, the variant PD-L1 polypeptide present in a multimeric polypeptide of the present disclosure comprises the amino acid sequence set forth in SEQ ID NO:2, with an amino acid substitution at G101. For example, in some cases, the variant PD-L1 polypeptide present in a multimeric polypeptide of the present disclosure comprises the amino acid sequence set forth in FIG. 2B, where amino acid 119 is any amino acid other than glycine; for example, amino acid 119 can be Ala, Val, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2B, where amino acid 119 is Ala, Val, Leu, or Ile, instead of Gly. In some cases, the variant PD-L1 polypeptide present in a multimeric polypeptide of the present disclosure comprises the amino acid sequence set forth in FIG. 2B, where amino acid 119 is Arg, His, or Lys, instead of Gly. In some cases, the variant PD-L1 polypeptide present in a multimeric polypeptide of the present disclosure comprises the amino acid sequence set forth in FIG. 2B, where amino acid 119 is Asp or Glu, instead of Gly. In some cases, the variant PD-L1 polypeptide present in a multimeric polypeptide of the present disclosure comprises the amino acid sequence set forth in FIG. 2B, where amino acid 119 is Arg instead of Gly. In some cases, the variant PD-L1 polypeptide present in a multimeric polypeptide of the present disclosure comprises the amino acid sequence set forth in FIG. 2B, where amino acid 119 is Asp instead of Gly. In some cases, the variant PD-L1 polypeptide present in a multimeric polypeptide of the present disclosure comprises the amino acid sequence set forth in FIG. 2B, where amino acid 119 is Ala instead of Gly.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at G101; i.e., where amino acid 101 is other than glycine. For example, in some cases, the variant PD-L1 polypeptide present in a multimeric polypeptide of the present disclosure comprises the amino acid sequence set forth in SEQ ID NO:2, where amino acid 101 is any amino acid other than glycine; for example, amino acid 101 can be Ala, Val, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:2, where amino acid 101 is Arg, His, or Lys instead of Gly. In some cases, the variant PD-L1 polypeptide present in a multimeric polypeptide of the present disclosure comprises the amino acid sequence set forth in SEQ ID NO:2, where amino acid 101 is Asp or Glu instead of Gly. In some cases, the variant PD-L1 polypeptide present in a multimeric polypeptide of the present disclosure comprises the amino acid sequence set forth in SEQ ID NO:2, where amino acid 101 is Ala, Val, Leu, or Ile instead of Gly. In some cases, the variant PD-L1 polypeptide present in a multimeric polypeptide of the present disclosure comprises the amino acid sequence set forth in SEQ ID NO:2, where amino acid 101 is Arg instead of Gly. In some cases, the variant PD-L1 polypeptide present in a multimeric polypeptide of the present disclosure comprises the amino acid sequence set forth in SEQ ID NO:2, where amino acid 101 is Ala instead of Gly. In some cases, the variant PD-L1 polypeptide present in a multimeric polypeptide of the present disclosure comprises the amino acid sequence set forth in SEQ ID NO:2, where amino acid 101 is Asp instead of Gly.

G120

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 120 is an amino acid other than glycine, e.g., where amino acid 120 is Ala, Val, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 120 is Ala, Val, Leu, or Ile. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 120 is Asp or Glu. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 120 is Arg, His, or Lys. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 120 is Asp. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 120 is Arg. In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 120 is Ala. In some cases, a multimeric polypeptide of the present disclosure exhibits from about 20% to about 50%, or from about 50% to 100%, of the binding affinity to PD-1 (e.g., to a PD-1 polypeptide comprising the amino acid sequence depicted in FIG. 3B) exhibited by a control multimeric polypeptide comprising a PD-L1 polypeptide comprising the amino acid sequence set forth in FIG. 2B (or set forth in SEQ ID NO:2) for the PD-1 polypeptide; and exhibits reduced binding affinity to B7-1 (e.g., exhibits from about 60% to about 95% reduced binding affinity to B7-1) compared to the binding affinity of a control multimeric polypeptide comprising a wild-type PD-L1 polypeptide (e.g., a PD-L1 polypeptide comprising the amino acid sequence set forth in FIG. 3B or in SEQ ID NO:2) for a wild-type B7-1 polypeptide (e.g., a B7-1 polypeptide comprising the amino acid sequence depicted in FIG. 3D).

In some cases, the variant PD-L1 polypeptide present in a multimeric polypeptide of the present disclosure comprises the amino acid sequence set forth in FIG. 2B, with an amino acid substitution at G120. In some cases, the variant PD-L1 polypeptide present in a multimeric polypeptide of the present disclosure comprises the amino acid sequence set forth in SEQ ID NO:2, with an amino acid substitution at G102. For example, in some cases, the variant PD-L1 polypeptide present in a multimeric polypeptide of the present disclosure comprises the amino acid sequence set forth in FIG. 2B, where amino acid 120 is any amino acid other than glycine; for example, amino acid 120 can be Ala, Val, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in FIG. 2B, where amino acid 120 is Ala, Val, Leu, or Ile, instead of Gly. In some cases, the variant PD-L1 polypeptide present in a multimeric polypeptide of the present disclosure comprises the amino acid sequence set forth in FIG. 2B, where amino acid 120 is Arg, His, or Lys, instead of Gly. In some cases, the variant PD-L1 polypeptide present in a multimeric polypeptide of the present disclosure comprises the amino acid sequence set forth in FIG. 2B, where amino acid 120 is Asp or Glu, instead of Gly. In some cases, the variant PD-L1 polypeptide present in a multimeric polypeptide of the present disclosure comprises the amino acid sequence set forth in FIG. 2B, where amino acid 120 is Arg instead of Gly. In some cases, the variant PD-L1 polypeptide present in a multimeric polypeptide of the present disclosure comprises the amino acid sequence set forth in FIG. 2B, where amino acid 120 is Asp instead of Gly. In some cases, the variant PD-L1 polypeptide present in a multimeric polypeptide of the present disclosure comprises the amino acid sequence set forth in FIG. 2B, where amino acid 120 is Ala instead of Gly.

In some cases, the variant PD-L1 polypeptide present in a multimeric polypeptide of the present disclosure comprises an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, with an amino acid substitution at G102; i.e., where amino acid 102 is other than glycine. For example, in some cases, the variant PD-L1 polypeptide present in a multimeric polypeptide of the present disclosure comprises the amino acid sequence set forth in SEQ ID NO:2, where amino acid 102 is any amino acid other than glycine; for example, amino acid 101 can be Ala, Val, Leu, Ile, Pro, Phe, Tyr, Trp, Ser, Thr, Cys, Met, Asn, Gln, Lys, Arg, His, Asp, or Glu. In some cases, the variant PD-L1 polypeptide present in a multimeric polypeptide of the present disclosure comprises the amino acid sequence set forth in SEQ ID NO:2, where amino acid 102 is Arg, His, or Lys instead of Gly. In some cases, the variant PD-L1 polypeptide present in a multimeric polypeptide of the present disclosure comprises the amino acid sequence set forth in SEQ ID NO:2, where amino acid 102 is Asp or Glu instead of Gly. In some cases, the variant PD-L1 polypeptide present in a multimeric polypeptide of the present disclosure comprises the amino acid sequence set forth in SEQ ID NO:2, where amino acid 102 is Ala, Val, Leu, or Ile instead of Gly. In some cases, the variant PD-L1 polypeptide present in a multimeric polypeptide of the present disclosure comprises the amino acid sequence set forth in SEQ ID NO:2, where amino acid 102 is Arg instead of Gly. In some cases, the variant PD-L1 polypeptide present in a multimeric polypeptide of the present disclosure comprises the amino acid sequence set forth in SEQ ID NO:2, where amino acid 102 is Ala instead of Gly. In some cases, the variant PD-L1 polypeptide present in a multimeric polypeptide of the present disclosure comprises the amino acid sequence set forth in SEQ ID NO:2, where amino acid 102 is Asp instead of Gly.

Multiple Variant PD-L1 Immunomodulatory Domains

In some cases, a multimeric polypeptide of the present disclosure includes a single variant PD-L1 immunomodulatory polypeptide.

In some cases, a multimeric polypeptide of the present disclosure includes two variant PD-L1 immunomodulatory polypeptides. In some cases, the two variant PD-L1 immunomodulatory polypeptides are in tandem in a polypeptide chain. In some cases, the two variant PD-L1 immunomodulatory polypeptides are in separate polypeptide chains. In some cases, the two variant PD-L1 immunomodulatory polypeptides are in separate polypeptide chains of the multimeric polypeptide. In some cases, the two variant PD-L1 polypeptides have the same amino acid sequence as one another. In some cases, the two variant PD-L1 polypeptides have different amino acid sequences (e.g., the two differ from one another by at least one amino acid).

In some cases, a multimeric polypeptide of the present disclosure includes three variant PD-L1 immunomodulatory polypeptides. In some cases, the three variant PD-L1 immunomodulatory polypeptides are in tandem in a polypeptide chain. In some cases, one of the three variant PD-L1 immunomodulatory polypeptides is on a separate polypeptide chain of the multimeric polypeptide from the other two variant PD-L1 immunomodulatory polypeptides. In some cases, the three variant PD-L1 polypeptides have the same amino acid sequence as one another. In some cases, each of the three variant PD-L1 polypeptides has a different amino acid sequence (e.g., each differs from the other two by at least one amino acid).

Scaffold Polypeptides

A T-cell modulatory multimeric polypeptide of the present disclosure comprises an Fc polypeptide, or another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly), where X any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be a half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life (e.g., the serum half-life) of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first and/or the second polypeptide chain of a multimeric polypeptide of the present disclosure comprises an Fc polypeptide. The Fc polypeptide of a multimeric polypeptide of the present disclosure can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIG. 4A-4C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A; and comprises a substitution of N77; e.g., the Fc polypeptide comprises an N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 4B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 4B. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 4C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 4C.

Additional Polypeptides

A polypeptide chain of a multimeric polypeptide of the present disclosure can include one or more polypeptides in addition to those described above. Suitable additional polypeptides include epitope tags and affinity domains. The one or more additional polypeptide can be included at the N-terminus of a polypeptide chain of a multimeric polypeptide of the present disclosure, at the C-terminus of a polypeptide chain of a multimeric polypeptide of the present disclosure, or internally within a polypeptide chain of a multimeric polypeptide of the present disclosure.

Epitope Tag

Suitable epitope tags include, but are not limited to, hemagglutinin (HA; e.g., YPYDVPDYA (SEQ ID NO:22); FLAG (e.g., DYKDDDDK (SEQ ID NO:23); c-myc (e.g., EQKLISEEDL; SEQ ID NO:24), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:25), His×6 (HHHHHH) (SEQ ID NO:26), C-myc (EQKLISEEDL) (SEQ ID NO:27), Flag (DYKDDDDK) (SEQ ID NO:28), StrepTag (WSHPQFEK) (SEQ ID NO:29), hemagglutinin, e.g., HA Tag (YPYDVPDYA) (SEQ ID NO:30), glutathione-S-transferase (GST), thioredoxin, cellulose binding domain, RYIRS (SEQ ID NO:31), Phe-His-His-Thr (SEQ ID NO:32), chitin binding domain, S-peptide, T7 peptide, SH2 domain, C-end RNA tag, WEAAAREACCRECCARA (SEQ ID NO:33), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Exemplary Multimeric Polypeptides

Exemplary multimeric polypeptides of the present disclosure are described below.

D26 Substitution

In some cases, a multimeric polypeptide of the present disclosure comprises: a) a first polypeptide comprising, in order from N-terminus to C-terminus: i) an epitope; ii) a β2M polypeptide; and iii) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is an amino acid other than an aspartic acid, e.g., where amino acid 26 is Gly, Ala, Val, Leu, Ile, Pro, Phe, Tyr, Trp, Ser, Thr, Cys, Met, Asn, Gln, Lys, Arg, His, or Glu; e.g., where amino acid 26 is Ala or Arg; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 8 is an amino acid other than an aspartic acid, e.g., where amino acid 8 is Gly, Ala, Val, Leu, Ile, Pro, Phe, Tyr, Trp, Ser, Thr, Cys, Met, Asn, Gln, Lys, Arg, His, or Glu; e.g., where amino acid 8 is Ala or Arg; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is an amino acid other than an aspartic acid, e.g., where amino acid 26 is Gly, Ala, Val, Leu, Ile, Pro, Phe, Tyr, Trp, Ser, Thr, Cys, Met, Asn, Gln, Lys, Arg, His, or Glu; e.g., where amino acid 26 is Ala or Arg; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 8 is an amino acid other than an aspartic acid, e.g., where amino acid 8 is Gly, Ala, Val, Leu, Ile, Pro, Phe, Tyr, Trp, Ser, Thr, Cys, Met, Asn, Gln, Lys, Arg, His, or Glu; e.g., where amino acid 8 is Ala or Arg; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant PD-L1 polypeptide of the present disclosure; iv) a second variant PD-L1 polypeptide of the present disclosure; and v) a third variant PD-L1 polypeptide of the present disclosure; and b) a second polypeptide comprising, in order from N-terminus to C-terminus: i) a Class I MHC heavy chain; and ii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is an amino acid other than an aspartic acid, e.g., where amino acid 26 is Gly, Ala, Val, Leu, Ile, Pro, Phe, Tyr, Trp, Ser, Thr, Cys, Met, Asn, Gln, Lys, Arg, His, or Glu; e.g., where amino acid 26 is Ala or Arg; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 8 is an amino acid other than an aspartic acid, e.g., where amino acid 8 is Gly, Ala, Val, Leu, Ile, Pro, Phe, Tyr, Trp, Ser, Thr, Cys, Met, Asn, Gln, Lys, Arg, His, or Glu; e.g., where amino acid 8 is Ala or Arg. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a second variant PD-L1 polypeptide of the present disclosure; and iii) a third variant PD-L1 polypeptide of the present disclosure; iv) a Class I MHC heavy chain; and v) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is an amino acid other than an aspartic acid, e.g., where amino acid 26 is Gly, Ala, Val, Leu, Ile, Pro, Phe, Tyr, Trp, Ser, Thr, Cys, Met, Asn, Gln, Lys, Arg, His, or Glu; e.g., where amino acid 26 is Ala or Arg; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 8 is an amino acid other than an aspartic acid, e.g., where amino acid 8 is Gly, Ala, Val, Leu, Ile, Pro, Phe, Tyr, Trp, Ser, Thr, Cys, Met, Asn, Gln, Lys, Arg, His, or Glu; e.g., where amino acid 8 is Ala or Arg. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a linker; iii) a second variant PD-L1 polypeptide of the present disclosure; iv) a linker; v) a third variant PD-L1 polypeptide of the present disclosure; vi) a Class I MHC heavy chain; and vii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 26 is an amino acid other than an aspartic acid, e.g., where amino acid 26 is Gly, Ala, Val, Leu, Ile, Pro, Phe, Tyr, Trp, Ser, Thr, Cys, Met, Asn, Gln, Lys, Arg, His, or Glu; e.g., where amino acid 26 is Ala or Arg; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 8 is an amino acid other than an aspartic acid, e.g., where amino acid 8 is Gly, Ala, Val, Leu, Ile, Pro, Phe, Tyr, Trp, Ser, Thr, Cys, Met, Asn, Gln, Lys, Arg, His, or Glu; e.g., where amino acid 8 is Ala or Arg. In some cases, the linker comprises a (GSSSS)n sequence, where n is 1, 2, 3, 4, or 5. In some cases, n is 4. In some cases, n is 5.

T37 Substitution

In some cases, a multimeric polypeptide of the present disclosure comprises: a) a first polypeptide comprising, in order from N-terminus to C-terminus: i) an epitope; ii) a β2M polypeptide; and iii) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is an amino acid other than threonine, e.g., where amino acid 37 is Gly, Ala, Val, Leu, Ile, Pro, Phe, Tyr, Trp, Ser, Cys, Met, Asn, Gln, Lys, Arg, His, Asp, or Glu; e.g., where amino acid 37 is Gly, Ala, Val, Leu, Ile, Arg, Lys, or His; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 19 is any amino acid other than threonine; for example, amino acid 19 can be Gly, Ala, Val, Leu, Ile, Pro, Phe, Tyr, Trp, Ser, Cys, Met, Asn, Gln, Lys, Arg, His, Asp, or Glu; e.g., where amino acid 19 is Gly, Ala, Val, Leu, Ile, Arg, Lys, or His; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is an amino acid other than threonine, e.g., where amino acid 37 is Gly, Ala, Val, Leu, Ile, Pro, Phe, Tyr, Trp, Ser, Cys, Met, Asn, Gln, Lys, Arg, His, Asp, or Glu; e.g., where amino acid 37 is Gly, Ala, Val, Leu, Ile, Arg, Lys, or His; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 19 is any amino acid other than threonine; for example, amino acid 19 can be Gly, Ala, Val, Leu, Ile, Pro, Phe, Tyr, Trp, Ser, Cys, Met, Asn, Gln, Lys, Arg, His, Asp, or Glu; e.g., where amino acid 19 is Gly, Ala, Val, Leu, Ile, Arg, Lys, or His; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant PD-L1 polypeptide of the present disclosure; iv) a second variant PD-L1 polypeptide of the present disclosure; and v) a third variant PD-L1 polypeptide of the present disclosure; and b) a second polypeptide comprising, in order from N-terminus to C-terminus: i) a Class I MHC heavy chain; and ii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is an amino acid other than threonine, e.g., where amino acid 37 is Gly, Ala, Val, Leu, Ile, Pro, Phe, Tyr, Trp, Ser, Cys, Met, Asn, Gln, Lys, Arg, His, Asp, or Glu; e.g., where amino acid 37 is Gly, Ala, Val, Leu, Ile, Arg, Lys, or His; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 19 is any amino acid other than threonine; for example, amino acid 19 can be Gly, Ala, Val, Leu, Ile, Pro, Phe, Tyr, Trp, Ser, Cys, Met, Asn, Gln, Lys, Arg, His, Asp, or Glu; e.g., where amino acid 19 is Gly, Ala, Val, Leu, Ile, Arg, Lys, or His. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a second variant PD-L1 polypeptide of the present disclosure; and iii) a third variant PD-L1 polypeptide of the present disclosure; iv) a Class I MHC heavy chain; and v) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is an amino acid other than threonine, e.g., where amino acid 37 is Gly, Ala, Val, Leu, Ile, Pro, Phe, Tyr, Trp, Ser, Cys, Met, Asn, Gln, Lys, Arg, His, Asp, or Glu; e.g., where amino acid 37 is Gly, Ala, Val, Leu, Ile, Arg, Lys, or His; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 19 is any amino acid other than threonine; for example, amino acid 19 can be Gly, Ala, Val, Leu, Ile, Pro, Phe, Tyr, Trp, Ser, Cys, Met, Asn, Gln, Lys, Arg, His, Asp, or Glu; e.g., where amino acid 19 is Gly, Ala, Val, Leu, Ile, Arg, Lys, or His. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a linker; iii) a second variant PD-L1 polypeptide of the present disclosure; iv) a linker; v) a third variant PD-L1 polypeptide of the present disclosure; vi) a Class I MHC heavy chain; and vii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 37 is an amino acid other than threonine, e.g., where amino acid 37 is Gly, Ala, Val, Leu, Ile, Pro, Phe, Tyr, Trp, Ser, Cys, Met, Asn, Gln, Lys, Arg, His, Asp, or Glu; e.g., where amino acid 37 is Gly, Ala, Val, Leu, Ile, Arg, Lys, or His; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 19 is any amino acid other than threonine; for example, amino acid 19 can be Gly, Ala, Val, Leu, Ile, Pro, Phe, Tyr, Trp, Ser, Cys, Met, Asn, Gln, Lys, Arg, His, Asp, or Glu; e.g., where amino acid 19 is Gly, Ala, Val, Leu, Ile, Arg, Lys, or His. In some cases, the linker comprises a (GSSSS)n sequence, where n is 1, 2, 3, 4, or 5. In some cases, n is 4. In some cases, n is 5.

Y56 Substitution

In some cases, a multimeric polypeptide of the present disclosure comprises: a) a first polypeptide comprising, in order from N-terminus to C-terminus: i) an epitope; ii) a β2M polypeptide; and iii) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is an amino acid other than tyrosine, e.g., where amino acid 56 is Gly, Ala, Val, Leu, Ile, Pro, Phe, Trp, Ser, Thr, Cys, Met, Asn, Gln, Lys, Arg, His, Asp, or Glu, where amino acid 56 is Ala, Gly, Val, Leu, or Ile, where amino acid 56 is Asp or Glu, or where amino acid 56 is Arg, His, or Lys; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 38 is an amino acid other than tyrosine, e.g., where amino acid 56 is Gly, Ala, Val, Leu, Ile, Pro, Phe, Trp, Ser, Thr, Cys, Met, Asn, Gln, Lys, Arg, His, Asp, or Glu, where amino acid 38 is Ala, Gly, Val, Leu, or Ile, where amino acid 38 is Asp or Glu, or where amino acid 38 is Arg, His, or Lys; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is an amino acid other than tyrosine, e.g., where amino acid 56 is Gly, Ala, Val, Leu, Ile, Pro, Phe, Trp, Ser, Thr, Cys, Met, Asn, Gin, Lys, Arg, His, Asp, or Glu, where amino acid 56 is Ala, Gly, Val, Leu, or Ile, where amino acid 56 is Asp or Glu, or where amino acid 56 is Arg, His, or Lys; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 38 is an amino acid other than tyrosine, e.g., where amino acid 38 is Gly, Ala, Val, Leu, Ile, Pro, Phe, Trp, Ser, Thr, Cys, Met, Asn, Gln, Lys, Arg, His, Asp, or Glu, where amino acid 38 is Ala, Gly, Val, Leu, or Ile, where amino acid 38 is Asp or Glu, or where amino acid 38 is Arg, His, or Lys; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant PD-L1 polypeptide of the present disclosure; iv) a second variant PD-L1 polypeptide of the present disclosure; and v) a third variant PD-L1 polypeptide of the present disclosure; and b) a second polypeptide comprising, in order from N-terminus to C-terminus: i) a Class I MHC heavy chain; and ii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is an amino acid other than tyrosine, e.g., where amino acid 56 is Gly, Ala, Val, Leu, Ile, Pro, Phe, Trp, Ser, Thr, Cys, Met, Asn, Gln, Lys, Arg, His, Asp, or Glu, where amino acid 56 is Ala, Gly, Val, Leu, or Ile, where amino acid 56 is Asp or Glu, or where amino acid 56 is Arg, His, or Lys; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 38 is an amino acid other than tyrosine, e.g., where amino acid 38 is Gly, Ala, Val, Leu, Ile, Pro, Phe, Trp, Ser, Thr, Cys, Met, Asn, Gln, Lys, Arg, His, Asp, or Glu, where amino acid 38 is Ala, Gly, Val, Leu, or Ile, where amino acid 38 is Asp or Glu, or where amino acid 38 is Arg, His, or Lys. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a second variant PD-L1 polypeptide of the present disclosure; and iii) a third variant PD-L1 polypeptide of the present disclosure; iv) a Class I MHC heavy chain; and v) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is an amino acid other than tyrosine, e.g., where amino acid 56 is Gly, Ala, Val, Leu, Ile, Pro, Phe, Trp, Ser, Thr, Cys, Met, Asn, Gin, Lys, Arg, His, Asp, or Glu, where amino acid 56 is Ala, Gly, Val, Leu, or Ile, where amino acid 56 is Asp or Glu, or where amino acid 56 is Arg, His, or Lys; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 38 is an amino acid other than tyrosine, e.g., where amino acid 38 is Gly, Ala, Val, Leu, Ile, Pro, Phe, Trp, Ser, Thr, Cys, Met, Asn, Gln, Lys, Arg, His, Asp, or Glu, where amino acid 38 is Ala, Gly, Val, Leu, or Ile, where amino acid 38 is Asp or Glu, or where amino acid 38 is Arg, His, or Lys. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a linker; iii) a second variant PD-L1 polypeptide of the present disclosure; iv) a linker; v) a third variant PD-L1 polypeptide of the present disclosure; vi) a Class I MHC heavy chain; and vii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 56 is an amino acid other than tyrosine, e.g., where amino acid 56 is Gly, Ala, Val, Leu, Ile, Pro, Phe, Trp, Ser, Thr, Cys, Met, Asn, Gln, Lys, Arg, His, Asp, or Glu, where amino acid 56 is Ala, Gly, Val, Leu, or Ile, where amino acid 56 is Asp or Glu, or where amino acid 56 is Arg, His, or Lys; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 38 is an amino acid other than tyrosine, e.g., where amino acid 38 is Gly, Ala, Val, Leu, Ile, Pro, Phe, Trp, Ser, Thr, Cys, Met, Asn, Gln, Lys, Arg, His, Asp, or Glu, where amino acid 38 is Ala, Gly, Val, Leu, or Ile, where amino acid 38 is Asp or Glu, or where amino acid 38 is Arg, His, or Lys. In some cases, the linker comprises a (GSSSS)n sequence, where n is 1, 2, 3, 4, or 5. In some cases, n is 4. In some cases, n is 5.

G119 Substitution

In some cases, a multimeric polypeptide of the present disclosure comprises: a) a first polypeptide comprising, in order from N-terminus to C-terminus: i) an epitope; ii) a β2M polypeptide; and iii) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is an amino acid other than glycine, e.g., where amino acid 119 is Ala, Val, Leu, Ile, Pro, Phe, Tyr, Trp, Ser, Thr, Cys, Met, Asn, Gln, Lys, Arg, His, Asp, or Glu, where amino acid 119 is Ala, Val, Leu, or Ile, where amino acid 119 is Arg, His, or Lys, or where amino acid 119 is Glu or Asp; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 101 is an amino acid other than glycine, e.g., where amino acid 101 is Ala, Val, Leu, Ile, Pro, Phe, Tyr, Trp, Ser, Thr, Cys, Met, Asn, Gln, Lys, Arg, His, Asp, or Glu, where amino acid 101 is Ala, Val, Leu, or Ile, where amino acid 101 is Arg, His, or Lys, or where amino acid 101 is Glu or Asp; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is an amino acid other than glycine, e.g., where amino acid 119 is Ala, Val, Leu, Ile, Pro, Phe, Tyr, Trp, Ser, Thr, Cys, Met, Asn, Gln, Lys, Arg, His, Asp, or Glu, where amino acid 119 is Ala, Val, Leu, or Ile, where amino acid 119 is Arg, His, or Lys, or where amino acid 119 is Glu or Asp; or a variant PD-L1 polypeptide comprising an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 101 is an amino acid other than glycine, e.g., where amino acid 101 is Ala, Val, Leu, Ile, Pro, Phe, Tyr, Trp, Ser, Thr, Cys, Met, Asn, Gln, Lys, Arg, His, Asp, or Glu, where amino acid 101 is Ala, Val, Leu, or Ile, where amino acid 101 is Arg, His, or Lys, or where amino acid 101 is Glu or Asp; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant PD-L1 polypeptide of the present disclosure; iv) a second variant PD-L1 polypeptide of the present disclosure; and v) a third variant PD-L1 polypeptide of the present disclosure; and b) a second polypeptide comprising, in order from N-terminus to C-terminus: i) a Class I MHC heavy chain; and ii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is an amino acid other than glycine, e.g., where amino acid 119 is Ala, Val, Leu, Ile, Pro, Phe, Tyr, Trp, Ser, Thr, Cys, Met, Asn, Gln, Lys, Arg, His, Asp, or Glu, where amino acid 119 is Ala, Val, Leu, or Ile, where amino acid 119 is Arg, His, or Lys, or where amino acid 119 is Glu or Asp; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 101 is an amino acid other than glycine, e.g., where amino acid 101 is Ala, Val, Leu, Ile, Pro, Phe, Tyr, Trp, Ser, Thr, Cys, Met, Asn, Gln, Lys, Arg, His, Asp, or Glu, where amino acid 101 is Ala, Val, Leu, or Ile, where amino acid 101 is Arg, His, or Lys, or where amino acid 101 is Glu or Asp. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a second variant PD-L1 polypeptide of the present disclosure; and iii) a third variant PD-L1 polypeptide of the present disclosure; iv) a Class I MHC heavy chain; and v) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is an amino acid other than glycine, e.g., where amino acid 119 is Ala, Val, Leu, Ile, Pro, Phe, Tyr, Trp, Ser, Thr, Cys, Met, Asn, Gln, Lys, Arg, His, Asp, or Glu, where amino acid 119 is Ala, Val, Leu, or Ile, where amino acid 119 is Arg, His, or Lys, or where amino acid 119 is Glu or Asp; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 101 is an amino acid other than glycine, e.g., where amino acid 101 is Ala, Val, Leu, Ile, Pro, Phe, Tyr, Trp, Ser, Thr, Cys, Met, Asn, Gln, Lys, Arg, His, Asp, or Glu, where amino acid 101 is Ala, Val, Leu, or Ile, where amino acid 101 is Arg, His, or Lys, or where amino acid 101 is Glu or Asp. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant PD-L1 polypeptide of the present disclosure; ii) a linker; iii) a second variant PD-L1 polypeptide of the present disclosure; iv) a linker; v) a third variant PD-L1 polypeptide of the present disclosure; vi) a Class I MHC heavy chain; and vii) an Fc polypeptide. In some cases, each of the first, second, and third variant PD-L1 polypeptides comprises: i) an amino acid sequence having at least 70%, at least 75%, at least 80%, at least 85%, at least 90%, at least 95%, at least 98%, or at least 99%, amino acid sequence identity to the amino acid sequence depicted in FIG. 2B, where amino acid 119 is an amino acid other than glycine, e.g., where amino acid 119 is Ala, Val, Leu, Ile, Pro, Phe, Tyr, Trp, Ser, Thr, Cys, Met, Asn, Gln, Lys, Arg, His, Asp, or Glu, where amino acid 119 is Ala, Val, Leu, or Ile, where amino acid 119 is Arg, His, or Lys, or where amino acid 119 is Glu or Asp; or ii) an amino acid sequence having at least 70%, at least 75%, at least 80%, at least 85%, at least 90%, at least 95%, at least 98%, or at least 99%, amino acid sequence identity to the amino acid sequence set forth in SEQ ID NO:2, where amino acid 101 is an amino acid other than glycine, e.g., where amino acid 101 is Ala, Val, Leu, Ile, Pro, Phe, Tyr, Trp, Ser, Thr, Cys, Met, Asn, Gln, Lys, Arg, His, Asp, or Glu, where amino acid 101 is Ala, Val, Leu, or Ile, where amino acid 101 is Arg, His, or Lys, or where amino acid 101 is Glu or Asp. In some cases, the linker comprises a (GSSSS)n sequence, where n is 1, 2, 3, 4, or 5. In some cases, n is 4. In some cases, n is 5.

In any of the above-described embodiments, the variant PD-L1 polypeptide present in the multimeric polypeptide can comprise a substitution of an amino acid as set out in FIG. 10 or FIG. 11. The following are examples. In some cases, a variant PD-L1 polypeptide present in a multimeric polypeptide of the present disclosure comprises a substitution of D26 of the amino acid sequence depicted in FIG. 2B; or D8 of the amino acid sequence set forth in SEQ ID NO:2. In some cases, a variant PD-L1 polypeptide present in a multimeric polypeptide of the present disclosure comprises a substitution of T37 of the amino acid sequence depicted in FIG. 2B; or T19 of the amino acid sequence set forth in SEQ ID NO:2. In some cases, a variant PD-L1 polypeptide present in a multimeric polypeptide of the present disclosure comprises a substitution of D49 of the amino acid sequence depicted in FIG. 2B; or D31 of the amino acid sequence set forth in SEQ ID NO:2. In some cases, a variant PD-L1 polypeptide present in a multimeric polypeptide of the present disclosure comprises a substitution of L53 of the amino acid sequence depicted in FIG. 2B; or L35 of the amino acid sequence set forth in SEQ ID NO:2. In some cases, a variant PD-L1 polypeptide present in a multimeric polypeptide of the present disclosure comprises a substitution of I54 (V54 in mouse PD-L1) of the amino acid sequence depicted in FIG. 2B; or I36 of the amino acid sequence set forth in SEQ ID NO:2. In some cases, a variant PD-L1 polypeptide present in a multimeric polypeptide of the present disclosure comprises a substitution of Y56 of the amino acid sequence depicted in FIG. 2B; or Y38 of the amino acid sequence set forth in SEQ ID NO:2. In some cases, a variant PD-L1 polypeptide present in a multimeric polypeptide of the present disclosure comprises a substitution of Y56 of the amino acid sequence depicted in FIG. 2B; or Y38 of the amino acid sequence set forth in SEQ ID NO:2. In some cases, a variant PD-L1 polypeptide present in a multimeric polypeptide of the present disclosure comprises a substitution of Q66 of the amino acid sequence depicted in FIG. 2B; or Q48 of the amino acid sequence set forth in SEQ ID NO:2. In some cases, a variant PD-L1 polypeptide present in a multimeric polypeptide of the present disclosure comprises a substitution of Q66 of the amino acid sequence depicted in FIG. 2B; or Q48 of the amino acid sequence set forth in SEQ ID NO:2. In some cases, a variant PD-L1 polypeptide present in a multimeric polypeptide of the present disclosure comprises a substitution of E72 of the amino acid sequence depicted in FIG. 2B; or E54 of the amino acid sequence set forth in SEQ ID NO:2. In some cases, a variant PD-L1 polypeptide present in a multimeric polypeptide of the present disclosure comprises a substitution of M115 (I115 of mouse PD-L1) of the amino acid sequence depicted in FIG. 2B; or M97 of the amino acid sequence set forth in SEQ ID NO:2. In some cases, a variant PD-L1 polypeptide present in a multimeric polypeptide of the present disclosure comprises a substitution of I116 of the amino acid sequence depicted in FIG. 2B; or I98 of the amino acid sequence set forth in SEQ ID NO:2. In some cases, a variant PD-L1 polypeptide present in a multimeric polypeptide of the present disclosure comprises a substitution of G119 of the amino acid sequence depicted in FIG. 2B; or G101 of the amino acid sequence set forth in SEQ ID NO:2. In some cases, a variant PD-L1 polypeptide present in a multimeric polypeptide of the present disclosure comprises a substitution of G120 of the amino acid sequence depicted in FIG. 2B; or G102 of the amino acid sequence set forth in SEQ ID NO:2. In some cases, a variant PD-L1 polypeptide present in a multimeric polypeptide of the present disclosure comprises a substitution of G120 of the amino acid sequence depicted in FIG. 2B; or G102 of the amino acid sequence set forth in SEQ ID NO:2. In some cases, a variant PD-L1 polypeptide present in a multimeric polypeptide of the present disclosure comprises a substitution of A121 of the amino acid sequence depicted in FIG. 2B; or A103 of the amino acid sequence set forth in SEQ ID NO:2. In some cases, a variant PD-L1 polypeptide present in a multimeric polypeptide of the present disclosure comprises a substitution of D122 of the amino acid sequence depicted in FIG. 2B; or D104 of the amino acid sequence set forth in SEQ ID NO:2. In some cases, a variant PD-L1 polypeptide present in a multimeric polypeptide of the present disclosure comprises a substitution of Y123 of the amino acid sequence depicted in FIG. 2B; or Y105 of the amino acid sequence set forth in SEQ ID NO:2. In some cases, a variant PD-L1 polypeptide present in a multimeric polypeptide of the present disclosure comprises a substitution of K124 of the amino acid sequence depicted in FIG. 2B; or K106 of the amino acid sequence set forth in SEQ ID NO:2. In some cases, a variant PD-L1 polypeptide present in a multimeric polypeptide of the present disclosure comprises a substitution of R125 of the amino acid sequence depicted in FIG. 2B; or K107 of the amino acid sequence set forth in SEQ ID NO:2.

Nucleic Acids

The present disclosure provides a nucleic acid comprising a nucleotide sequence encoding a variant PD-L1 polypeptide of the present disclosure. The present disclosure provides a nucleic acid comprising a nucleotide sequence encoding a PD-L1 fusion polypeptide of the present disclosure.

The present disclosure provides nucleic acids comprising nucleotide sequences encoding a multimeric polypeptide of the present disclosure. In some cases, the individual polypeptide chains of a multimeric polypeptide of the present disclosure are encoded in separate nucleic acids. In some cases, all polypeptide chains of a multimeric polypeptide of the present disclosure are encoded in a single nucleic acid. In some cases, a first nucleic acid comprises a nucleotide sequence encoding a first polypeptide of a multimeric polypeptide of the present disclosure; and a second nucleic acid comprises a nucleotide sequence encoding a second polypeptide of a multimeric polypeptide of the present disclosure. In some cases, single nucleic acid comprises a nucleotide sequence encoding a first polypeptide of a multimeric polypeptide of the present disclosure and a second polypeptide of a multimeric polypeptide of the present disclosure.

Separate Nucleic Acids Encoding Individual Polypeptide Chains of a Multimeric Polypeptide The present disclosure provides nucleic acids comprising nucleotide sequences encoding a multimeric polypeptide of the present disclosure. As noted above, in some cases, the individual polypeptide chains of a multimeric polypeptide of the present disclosure are encoded in separate nucleic acids. In some cases, nucleotide sequences encoding the separate polypeptide chains of a multimeric polypeptide of the present disclosure are operably linked to transcriptional control elements, e.g., promoters, such as promoters that are functional in a eukaryotic cell, where the promoter can be a constitutive promoter or an inducible promoter. Thus, the present disclosure provides a composition comprising a first nucleic acid and a second nucleic acid, where the first nucleic acid comprises a nucleotide sequence encoding a first polypeptide chain of a multimeric polypeptide of the present disclosure, and where the second nucleic acid comprises a nucleotide sequence encoding a second polypeptide chain of a multimeric polypeptide of the present disclosure.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); b) a first MHC polypeptide; and c) an immunomodulatory polypeptide (e.g., a variant PD-L1 polypeptide of the present disclosure); and where the second nucleic acid comprises a nucleotide sequence encoding a second polypeptide of a multimeric polypeptide of the present disclosure, where the second polypeptide comprises, in order from N-terminus to C-terminus: a) a second MHC polypeptide; and b) an Ig Fc polypeptide. Suitable T-cell epitopes, MHC polypeptides, immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); and b) a first MHC polypeptide; and where the second nucleic acid comprises a nucleotide sequence encoding a second polypeptide of a multimeric polypeptide of the present disclosure, where the second polypeptide comprises, in order from N-terminus to C-terminus: a) an immunomodulatory polypeptide (e.g., a variant PD-L1 polypeptide of the present disclosure); b) a second MHC polypeptide; and c) an Ig Fc polypeptide. Suitable T-cell epitopes, MHC polypeptides, variant PD-L1 immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

Nucleic Acid Encoding Two or More Polypeptides Present in a Multimeric Polypeptide The present disclosure provides a nucleic acid comprising nucleotide sequences encoding at least the first polypeptide and the second polypeptide of a multimeric polypeptide of the present disclosure. In some cases, where a multimeric polypeptide of the present disclosure includes a first, second, and third polypeptide, the nucleic acid includes a nucleotide sequence encoding the first, second, and third polypeptides. In some cases, the nucleotide sequences encoding the first polypeptide and the second polypeptide of a multimeric polypeptide of the present disclosure include a proteolytically cleavable linker interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes an internal ribosome entry site (IRES) interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes a ribosome skipping signal (or cis-acting hydrolase element, CHYSEL) interposed between the nucleotide sequence encoding the first polypeptide and the nucleotide sequence encoding the second polypeptide. Examples of nucleic acids are described below, where a proteolytically cleavable linker is provided between nucleotide sequences encoding the first polypeptide and the second polypeptide of a multimeric polypeptide of the present disclosure; in any of these embodiments, an IRES or a ribosome skipping signal can be used in place of the nucleotide sequence encoding the proteolytically cleavable linker.

In some cases, a first nucleic acid (e.g., a recombinant expression vector, an mRNA, a viral RNA, etc.) comprises a nucleotide sequence encoding a first polypeptide chain of a multimeric polypeptide of the present disclosure; and a second nucleic acid (e.g., a recombinant expression vector, an mRNA, a viral RNA, etc.) comprises a nucleotide sequence encoding a second polypeptide chain of a multimeric polypeptide of the present disclosure. In some cases, the nucleotide sequence encoding the first polypeptide, and the second nucleotide sequence encoding the second polypeptide, are each operably linked to transcriptional control elements, e.g., promoters, such as promoters that are functional in a eukaryotic cell, where the promoter can be a constitutive promoter or an inducible promoter.

The present disclosure provides a nucleic acid comprising a nucleotide sequence encoding a recombinant polypeptide, where the recombinant polypeptide comprises, in order from N-terminus to C-terminus: a) an epitope (e.g., a T-cell epitope); b) a first MHC polypeptide; c) an immunomodulatory polypeptide (e.g., a variant PD-L1 polypeptide of the present disclosure); d) a proteolytically cleavable linker; e) a second MHC polypeptide; and f) an immunoglobulin (Ig) Fc polypeptide. The present disclosure provides a nucleic acid comprising a nucleotide sequence encoding a recombinant polypeptide, where the recombinant polypeptide comprises, in order from N-terminus to C-terminus: a) a first leader peptide; b) the epitope; c) the first MHC polypeptide; d) the immunomodulatory polypeptide (e.g., a variant PD-L1 polypeptide of the present disclosure); e) the proteolytically cleavable linker; f) a second leader peptide; g) the second MHC polypeptide; and h) the Ig Fc polypeptide. The present disclosure provides a nucleic acid comprising a nucleotide sequence encoding a recombinant polypeptide, where the recombinant polypeptide comprises, in order from N-terminus to C-terminus: a) an epitope; b) a first MHC polypeptide; c) a proteolytically cleavable linker; d) an immunomodulatory polypeptide (e.g., a variant PD-L1 polypeptide of the present disclosure); e) a second MHC polypeptide; and f) an Ig Fc polypeptide. In some cases, the first leader peptide and the second leader peptide is a β2-M leader peptide. In some cases, the nucleotide sequence is operably linked to a transcriptional control element. In some cases, the transcriptional control element is a promoter that is functional in a eukaryotic cell.

Suitable MHC polypeptides are described above. In some cases, the first MHC polypeptide is a β2-microglobulin polypeptide; and wherein the second MHC polypeptide is an MHC class I heavy chain polypeptide. In some cases, the β2-microglobulin polypeptide comprises an amino acid sequence having at least 85%, at least 90%, at least 95%, at least 98%, at least 99%, or 100%, amino acid sequence identity to any one of the amino acid sequences depicted in FIG. 6. In some cases, the MHC class I heavy chain polypeptide is an HLA-A, HLA-B, HLA-C, HLA-E, HLA-F, HLA-G, HLA-K, or HLA-L heavy chain. In some cases, the MHC class I heavy chain polypeptide comprises an amino acid sequence having at least 85% amino acid sequence identity to the amino acid sequence set forth in one of FIG. 5A-C. In some cases, the first MHC polypeptide is an MHC Class II alpha chain polypeptide; and wherein the second MHC polypeptide is an MHC class II beta chain polypeptide.

Suitable Fc polypeptides are described above. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85%, at least 90%, at least 95%, at least 98%, at least 99%, or 100%, amino acid sequence identity to an amino acid sequence depicted in FIG. 4A-4C.

Suitable variant PD-L1 immunomodulatory polypeptides are described above.

Suitable proteolytically cleavable linkers are described above. In some cases, the proteolytically cleavable linker comprises an amino acid sequence selected from: a) LEVLFQGP (SEQ ID NO:34); b) ENLYTQS (SEQ ID NO:35); c) DDDDK (SEQ ID NO:36); d) LVPR (SEQ ID NO:37); and e) GSGATNFSLLKQAGDVEENPGP (SEQ ID NO:38).

In some cases, a linker between the epitope and the first MHC polypeptide comprises a first Cys residue, and the second MHC polypeptide comprises an amino acid substitution to provide a second Cys residue, such that the first and the second Cys residues provide for a disulfide linkage between the linker and the second MHC polypeptide. In some cases, first MHC polypeptide comprises an amino acid substitution to provide a first Cys residue, and the second MHC polypeptide comprises an amino acid substitution to provide a second Cys residue, such that the first Cys residue and the second Cys residue provide for a disulfide linkage between the first MHC polypeptide and the second MHC polypeptide.

Recombinant Expression Vectors

The present disclosure provides recombinant expression vectors comprising nucleic acids of the present disclosure. In some cases, the recombinant expression vector is a non-viral vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, a nucleotide sequence encoding a DNA-targeting RNA and/or a site-directed modifying polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

Genetically Modified Host Cells

The present disclosure provides a genetically modified host cell, where the host cell is genetically modified with a nucleic acid of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), Chinese hamster ovary (CHO) cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, the host cell is a mammalian cell that has been genetically modified such that it does not synthesize endogenous MHC β2-M.

Methods of Producing a Multimeric Polypeptide

The present disclosure provides methods of producing a multimeric polypeptide of the present disclosure. The methods generally involve culturing, in a culture medium, a host cell that is genetically modified with a recombinant expression vector comprising a nucleotide sequence encoding the multimeric polypeptide; and isolating the multimeric polypeptide from the genetically modified host cell and/or the culture medium. A host cell that is genetically modified with a recombinant expression vector comprising a nucleotide sequence encoding the multimeric polypeptide is also referred to as an "expression host." As noted above, in some cases, the individual polypeptide chains of a multimeric polypeptide of the present disclosure are encoded in separate recombinant expression vectors. In some cases, all polypeptide chains of a multimeric polypeptide of the present disclosure are encoded in a single recombinant expression vector.

Isolation of the multimeric polypeptide from the expression host cell (e.g., from a lysate of the expression host cell) and/or the culture medium in which the host cell is cultured, can be carried out using standard methods of protein purification.

For example, a lysate may be prepared of the expression host and the lysate purified using high performance liquid chromatography (HPLC), exclusion chromatography, gel electrophoresis, affinity chromatography, or other purification technique. Alternatively, where the multimeric polypeptide is secreted from the expression host cell into the culture medium, the multimeric polypeptide can be purified from the culture medium using HPLC, exclusion chromatography, gel electrophoresis, affinity chromatography, or other purification technique. In some cases, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

In some cases, e.g., where the multimeric polypeptide comprises an affinity tag, the multimeric polypeptide can be purified using an immobilized binding partner of the affinity tag.

Compositions

The present disclosure provides compositions, including pharmaceutical compositions, comprising a variant PD-L1 polypeptide of the present disclosure. The present disclosure provides compositions, including pharmaceutical compositions, comprising a multimeric polypeptide of the present disclosure. The present disclosure provides compositions, including pharmaceutical compositions, comprising a nucleic acid or a recombinant expression vector of the present disclosure.

Compositions Comprising a Multimeric Polypeptide

A composition of the present disclosure can comprise, in addition to a multimeric polypeptide of the present disclosure, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise a multimeric polypeptide of the present disclosure, and a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a multimeric polypeptide of the present disclosure is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 *Ann. Rev. Biophys. Bioeng.* 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a multimeric polypeptide of the present disclosure in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

The present disclosure provides compositions, including pharmaceutical compositions, comprising a variant PD-L1 polypeptide of the present disclosure. A composition can comprise: a) a variant PD-L1 polypeptide of the present disclosure; and b) an excipient, as described above for the multimeric polypeptides. In some cases, the excipient is a pharmaceutically acceptable excipient.

Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) a subject nucleic acid or recombinant expression vector; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl) methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.). Suitable salts include, e.g., NaCl, $MgCl_2$, KCl, $MgSO_4$, etc.

A pharmaceutical formulation of the present disclosure can include a nucleic acid or recombinant expression vector of the present disclosure in an amount of from about 0.001% to about 90% (w/w). In the description of formulations, below, "subject nucleic acid or recombinant expression vector" will be understood to include a nucleic acid or recombinant expression vector of the present disclosure. For example, in some embodiments, a subject formulation comprises a nucleic acid or recombinant expression vector of the present disclosure.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

Treatment Methods

The present invention provides a method of selectively modulating the activity of an epitope-specific T cell in an individual, the method comprising administering to the individual an amount of the multimeric polypeptide of the present disclosure, or one or more nucleic acids encoding the multimeric polypeptide, effective to selectively modulate the activity of an epitope-specific T cell in an individual. In some cases, a treatment method of the present disclosure comprises administering to an individual in need thereof one or more recombinant expression vectors comprising nucleotide sequences encoding a multimeric polypeptide of the present disclosure. In some cases, a treatment method of the present disclosure comprises administering to an individual in need thereof one or more mRNA molecules comprising nucleotide sequences encoding a multimeric polypeptide of the present disclosure. In some cases, a treatment method of the present disclosure comprises administering to an individual in need thereof a multimeric polypeptide of the present disclosure.

The present disclosure provides a method of selectively modulating the activity of an epitope-specific T cell in an individual, the method comprising administering to the individual an effective amount of a multimeric polypeptide of the present disclosure, or one or more nucleic acids (e.g., expression vectors; mRNA; etc.) comprising nucleotide sequences encoding the multimeric polypeptide, where the multimeric polypeptide selectively modulates the activity of the epitope-specific T cell in the individual. Selectively modulating the activity of an epitope-specific T cell can treat a disease or disorder in the individual. Thus, the present disclosure provides a treatment method comprising administering to an individual in need thereof an effective amount of a multimeric polypeptide of the present disclosure.

In some cases, an immunomodulatory polypeptide (e.g., a variant PD-L1 polypeptide of the present disclosure) present in a multimeric polypeptide of the present disclosure is an inhibitory polypeptide, and the multimeric polypeptide comprising the variant PD-L1 polypeptide inhibits activity of an epitope-specific T cell. In some cases, the epitope is a self-epitope, and the multimeric polypeptide selectively inhibits the activity of a T cell specific for the self-epitope.

The present disclosure provides a method of treating an autoimmune disorder in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a self epitope, and where the multimeric polypeptide comprises a variant PD-L1 polypeptide of the present disclosure. In some cases, an "effective amount" of a multimeric polypeptide is an amount that, when administered in one or more doses to an individual in need thereof, reduces the number and/or activity of self-reactive T cells by at least 10%, at least 15%, at least 20%, at least 25%, at least 30%, at least 40%, at least 50%, at least 60%, at least 70%, at least 80%, at least 90%, or at least 95%, compared to number and/or activity of self-reactive T cells in the individual before administration of the multimeric polypeptide, or in the absence of administration with the multimeric polypeptide. In some cases, an "effective amount" of a multimeric polypeptide is an amount that, when administered in one or more doses to an individual in need thereof, reduces production of Th2 cytokines in the individual. In some cases, an "effective amount" of a multimeric polypeptide is an amount that, when administered in one or more doses to an individual in need thereof, ameliorates one or more symptoms associated with an autoimmune disease in the individual.

Autoimmune disorders that are amenable to treatment with a method of the present disclosure include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome (also known as limited cutaneous form of systemic sclerosis), cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), irritable bowel disease (IBD), IgA neuropathy, juvenile arthritis, lichen planus, lupus erthematosus, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatics, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

In some cases, an immunomodulatory polypeptide (e.g., a variant PD-L1 polypeptide of the present disclosure) present in a multimeric polypeptide of the present disclosure is an inhibitory polypeptide, and the multimeric polypeptide comprising the variant PD-L1 polypeptide inhibits activity of an epitope-specific T cell. In some cases, the epitope is an epitope on an allograft (e.g., a skin allograft, a liver allograft, a kidney allograft, a heart allograft, a bone allograft, a cartilage allograft, a lung allograft, a cell allograft (e.g., a bone marrow allograft), etc.); and the multimeric polypeptide selectively inhibits the activity of a T cell specific for an antigen present on the allograft.

The present disclosure provides a method of inhibiting allograft rejection in an individual, the method comprising administering to an individual (e.g., an individual who is a recipient of an allograft; or an individual who is about to become an allograft recipient) an effective amount of a multimeric polypeptide of the present disclosure, or one or more nucleic acids comprising nucleotide sequences encoding the multimeric polypeptide, where the multimeric polypeptide comprises a T-cell epitope that is an epitope present on an allograft, and where the multimeric polypeptide comprises a variant PD-L1 polypeptide of the present disclosure. In some cases, an "effective amount" of a multimeric polypeptide is an amount that, when administered in one or more doses to an individual in need thereof, reduces the number and/or activity of alloreactive (allograft reactive) T cells by at least 10%, at least 15%, at least 20%, at least 25%, at least 30%, at least 40%, at least 50%, at least 60%, at least 70%, at least 80%, at least 90%, or at least 95%, compared to number and/or activity of alloreactive (allograft reactive) T cells in the individual before administration of the multimeric polypeptide, or in the absence of administration with the multimeric polypeptide. In some cases, an "effective amount" of a multimeric polypeptide is an amount that, when administered in one or more doses to an individual in need thereof, increases the survival time of an allograft in the individual; e.g., the survival time of the allograft in the individual is increased by at least 25%, at least 50%, at least 2-fold, at least 5-fold, at least 10-fold, at least 50-fold, or at least 100-fold, compared to the allograft survival time in the individual in the absence of administration with the multimeric polypeptide. In some cases, an "effective amount" of a multimeric polypeptide is an amount that, when administered in one or more doses to an individual in need thereof, ameliorates one or more symptoms associated with allograft rejection in the individual.

As noted above, in some cases, in carrying out a subject treatment method, a multimeric polypeptide of the present disclosure is administered to an individual in need thereof, as the polypeptide per se. In other instances, in carrying out a subject treatment method, one or more nucleic acids comprising nucleotide sequences encoding a multimeric polypeptide of the present disclosure is/are administering to an individual in need thereof. Thus, in other instances, one or more nucleic acids of the present disclosure, e.g., one or more recombinant expression vectors of the present disclosure, is/are administered to an individual in need thereof.

Formulations

Suitable formulations are described above, where suitable formulations include a pharmaceutically acceptable excipient. In some cases, a suitable formulation comprises: a) a multimeric polypeptide of the present disclosure; and b) a pharmaceutically acceptable excipient. In some cases, a suitable formulation comprises: a) a nucleic acid comprising a nucleotide sequence encoding a multimeric polypeptide of the present disclosure; and b) a pharmaceutically acceptable excipient; in some instances, the nucleic acid is an mRNA. In some cases, a suitable formulation comprises: a) a first nucleic acid comprising a nucleotide sequence encoding the first polypeptide of a multimeric polypeptide of the present disclosure; b) a second nucleic acid comprising a nucleotide sequence encoding the second polypeptide of a multimeric polypeptide of the present disclosure; and c) a pharmaceutically acceptable excipient. In some cases, a suitable formulation comprises: a) a recombinant expression vector comprising a nucleotide sequence encoding a multimeric polypeptide of the present disclosure; and b) a pharmaceutically acceptable excipient. In some cases, a suitable formulation comprises: a) a first recombinant expression vector comprising a nucleotide sequence encoding the first polypeptide of a multimeric polypeptide of the present disclosure; b) a second recombinant expression vector comprising a nucleotide sequence encoding the second polypeptide of a multimeric polypeptide of the present disclosure; and c) a pharmaceutically acceptable excipient.

Suitable pharmaceutically acceptable excipients are described above.

Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide of the present disclosure may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

In some cases, a suitable dose of a multimeric polypeptide of the present disclosure is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide of the present disclosure is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide of the present disclosure, a nucleic acid of the present disclosure, or a recombinant expression vector of the present disclosure are administered. The frequency of administration of a multimeric polypeptide of the present disclosure, a nucleic acid of the present disclosure, or a recombinant expression vector of the present disclosure can vary depending on any of a variety of factors, e.g., severity of the symptoms, etc. For example, in some embodiments, a multimeric polypeptide of the present disclosure, a nucleic acid of the present disclosure, or a recombinant expression vector of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide of the present disclosure, a nucleic acid of the present disclosure, or a recombinant expression vector of the present disclosure, e.g., the period of time over which a multimeric polypeptide of the present disclosure, a nucleic acid of the present disclosure, or a recombinant expression vector of the present disclosure is administered, can vary, depending on any of a variety of factors, e.g., patient response, etc. For example, a multimeric polypeptide of the present disclosure, a nucleic acid of the present disclosure, or a recombinant expression vector of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

An active agent (a multimeric polypeptide of the present disclosure, a nucleic acid of the present disclosure, or a recombinant expression vector of the present disclosure) is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the multimeric polypeptide and/or the desired effect. A multimeric polypeptide of the present disclosure, or a nucleic acid or recombinant expression vector of the present disclosure, can be administered in a single dose or in multiple doses.

In some embodiments, a multimeric polypeptide of the present disclosure, a nucleic acid of the present disclosure, or a recombinant expression vector of the present disclosure is administered intravenously. In some embodiments, a multimeric polypeptide of the present disclosure, a nucleic acid of the present disclosure, or a recombinant expression vector of the present disclosure is administered intramuscularly. In some embodiments, a multimeric polypeptide of the present disclosure, a nucleic acid of the present disclosure, or a recombinant expression vector of the present disclosure is administered locally. In some embodiments, a multimeric polypeptide of the present disclosure, a nucleic acid of the present disclosure, or a recombinant expression vector of the present disclosure is administered intratumorally. In some embodiments, a multimeric polypeptide of the present disclosure, a nucleic acid of the present disclosure, or a recombinant expression vector of the present disclosure is administered peritumorally. In some embodiments, a multimeric polypeptide of the present disclosure, a nucleic acid of the present disclosure, or a recombinant expression vector of the present disclosure is administered intracranially. In some embodiments, a multimeric polypeptide of the present disclosure, a nucleic acid of the present disclosure, or a recombinant expression vector of the present disclosure is administered subcutaneously.

In some embodiments, a multimeric polypeptide of the present disclosure is administered intravenously. In some embodiments, a multimeric polypeptide of the present disclosure is administered intramuscularly. In some embodiments, a multimeric polypeptide of the present disclosure is administered locally. In some embodiments, a multimeric polypeptide of the present disclosure is administered intratumorally. In some embodiments, a multimeric polypeptide of the present disclosure is administered peritumorally. In some embodiments, a multimeric polypeptide of the present disclosure is administered intracranially. In some embodiments, a multimeric polypeptide is administered subcutaneously.

A multimeric polypeptide of the present disclosure, a nucleic acid of the present disclosure, or a recombinant expression vector of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of a multimeric polypeptide of the present disclosure, a nucleic acid of the present disclosure, or a recombinant expression vector of the present disclosure. Where systemic delivery is desired, administration typically involves invasive or systemically absorbed topical or mucosal administration of pharmaceutical preparations.

Subjects Suitable For Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment. Subjects suitable for treatment with a method of the present disclosure include individuals who have an infection (e.g., an infection with a pathogen such as a bacterium, a virus, a protozoan, etc.), including individuals who have been diagnosed as having an infection, and individuals who have been treated for an infection but who failed to respond to the treatment. Subjects suitable for treatment with a method of the present disclosure include individuals who have bacterial infection, including individuals who have been diagnosed as having a bacterial infection, and individuals who have been treated for a bacterial infection but who failed to respond to the treatment. Subjects suitable for treatment with a method of the present disclosure include individuals who have a viral infection, including individuals who have been diagnosed as having a viral infection, and individuals who have been treated for a viral infection but who failed to respond to the treatment. Subjects suitable for treatment with a method of the present disclosure include individuals who have an autoimmune disease, including individuals who have been diagnosed as having an autoimmune disease, and individuals who have been treated for a autoimmune disease but who failed to respond to the treatment.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Generation and Characterization of PD-L1 Variants

Materials and Methods

PD-L1 Mutagenesis

Full-length mouse PD-L1 was cloned into the SacI and BamHI sites of the Clontech N1 mCherry vector. The native leader peptide sequence was replaced by the EPO leader peptide sequence to improve localization and expression level. Site-specific mutagenesis was performed using high fidelity KOD polymerase, 2 mM dNTPs and 4 mM $MgCl_2$. Positions for mutagenesis were selected based on the crystal structure of complex formed by human PD-L1 and PD-1 (PDB: 3BIK). Equivalent surface accessible positions in mouse PD-L1 were identified by sequence alignment to human PD-L1 (36 positions total). Mutagenesis was attempted such that each chosen position was mutated to an Ala, Glu or Arg residue. The overall mutagenesis success rate was ~70%, and for some positions not all substitutions (A, E and R) were obtained. The sequence validated mutants were expression tested by transient transfection of 1 mL of suspension HEK 293 cells. Only those mutants that showed comparable expression to wild-type PD-L1 and correct membrane localization were subsequently utilized in the microarray and FACS binding studies yielding a final set of 60 PD-L1 mutants to assay.

Microbead FACS Binding Assay

PD-L1 mCherry mutant constructs were transiently transfected into HEK 293S cells and subsequently challenged with protein A microbeads (Milltenyi) pre-saturated with a 4:1 mixture of PD-1 Fc-fusion and FITC-Fc protein. A total Fc protein to bead ratio of 5 ug/10 uL microbeads was utilized on the basis of a previous report from Genentech (16). The FITC-Fc served to make the otherwise non-fluorescent microbeads show green fluorescence. For each titration experiment, 500 μL of protein A microbeads were loaded with a mixture of 10 μg fluorescein isothiocyanate (FITC)-Fc and 40 μg of either PD-1-Fc or B7-1-Fc protein in a total volume of 5 mL 1× phosphate buffered saline (PBS). The beads were incubated overnight (~16 hours) at 4° C. Loaded beads were stored for up to two weeks prior to use. Initial experiments determined that 75 μL of the loaded beads were sufficient to saturate 150,000 cells transfected with wild type PD-L1, (transfection efficiency being consistently 60-70%). For titration experiments, sets of wild type and mutant PD-L1 constructs were transfected in 24-well tissue culture plates containing 1 mL of suspension HEK-293 cells. Three days post transfection cells were counted, diluted to $1\times10^6$ cell/mL with 1×PBS with 2% BSA. 150K cells (150 μL) were transferred to Eppendorf tubes, and 75 μL of loaded microbeads added along with an additional 100 μL 1×PBS with 2% bovine serum albumin (BSA). Reactions were mixed end over end for 1 hour at 4° C., 4',6-diamidino-2-phenylindole (DAPI) was added and samples were immediately analyzed by flow cytometry on a BD Aria III cytometer. Data were analyzed by gating first for live cells (DAPI negative) then for mCherry positive cells (PD-L1 expression). The percentage of mCherry positive cells that were FITC positive (microbeads bound) was used as "percent bound". For each experiment, the percent bound was normalized to wild type binding.

Purification of Recombinant Fc-Fusion Protein

To clone mPD-L1 Fc-fusion protein, full-length wild type or mutant PD-L1 ectodomains (residues F19-R237) were sub-cloned into a LIC vector containing a C-terminal his-tagged Fc domain (mIgG2a-10×His). These constructs and an isotope only control were transiently expressed in 1 L of HEK 293 suspension cells. Four days post transfection, the media was harvested, 50 mM MES was added to adjust the pH and 100 mM Arg-Cl (pH 7.6) was added to improve solubility. Fc-fusions were subsequently purified over $Ni^{2+}$-NTA resin (GE) using a batch binding method followed by gravity flow over a 600 mL capacity glass column with a 10 mL resin bed volume. The $Ni^{2+}$-nitroloacetic acid (NTA) resin was washed with 100 column volumes of wash buffer (50 mM MES pH 6.5, 100 mM Arg-Cl, 5 mM imidazole, 150 mM NaCl, 10% Glycerol) and the bound protein eluted with the same buffer containing 500 mM immidizole. Nickel elutes were concentrated and further purified by gel filtration on an S200 sephadex column (GE) in 50 mM MES pH 6.5, 100 mM Arg-Cl, 150 mM NaCl, 10% Glycerol. Wild-type mPD-1 Fc (residues L25-Q167) and mB7-1 Fc (residues D37-K245) constructs were cloned into a lentiviral expression LIC vector that also contains the mIgG2a-10×His tag. The constructs were co-transfected with lentiviral packaging plasmids and viral supernatants collected after 2-days. Large-scale transductions were started in 125 mL baffled flasks with $20\times10^6$ cells and 5-10 mL of viral supernatant. A complete media change was performed on day 3 post transduction and starting on day 5 the cultures were scaled up ending with to a final volume of 1.5 L. Supernatants were collected for purification on day 12. Purification of supernatant obtained from the lentiviral produced PD-1 and B7-1 were purified as described for mPD-L1.

FACS Titration Assay

Fluorescence activated cell sorting (FACS) titration assays were performed with PD-1 Fc and B7-1 Fc fusion proteins purified in house as described above. HEK 293 suspension cells were transfected with the wild type or mutant PD-L1 constructs. Three days post transfection cells were counted and diluted to $1\times10^6$ cells/mL in 1×PBS. Premixed reactions containing a final concentration of 1 μM Fc-fusion protein and 1.5 μM Alexa 488 goat anti-mouse secondary antibody were incubated on ice for 30 min. Subsequently, increasing amounts of the premixed reaction was added to wells of a 96-well plate and the volume adjusted to 50 μL. 150 μL of diluted cells (150,000 cells total) were then added to the wells. Binding was performed at 4° C. for 1 hour and the cells washed 3× with PBS by centrifugation and subsequently analyzed by FACS. Gated live cells were sub-gated for mCherry and mCherry positive cells sub-gated for Alexa-488. The percent bound represents the percentage of mCherry cells that were Alexa-488 positive. Data represents the average of three independent experiments fit to the single site binding equation $Y=B_{max}*X/(EC_{50}+X)$.

T-Cell Activation Assay

Spleens were harvested from C57BL/6 mice and $CD4^+$ T-cells isolated using mouse anti-CD4 microbeads (Milltenyi). The $CD4^+$ T-cells were collected in complete RPMI media supplemented with 10% fetal bovine serum (FBS), pen/strep antibiotics, 2 mM L-glutamine and 0.1% BME. The cells were counted, stained with carboxyfluorescein N-succinimidyl ester (CFSE) (Invitrogen) using the manufacture's protocol and recounted. On the same day, 75,000 cells were plated per well in a 96-well TC plates in complete RPMI media and either left inactivated, activated with 33.3 nM (~5 ug/mL) anti-CD3, or activated with 33.3 nM anti-CD3 in the presence of a ~5-fold molar excess (174.3 nM) of either control Fc, WT PD-L1-Fc or mutant PD-L1 Fc proteins. Four days post activation, proliferation was determined by FACS by analyzing CSFE dilution by gating on the non-activated T-cells. The data from each experiment were normalized to the control Fc population and a total of three independent experiments were averaged.

PD-1/B7-1 Competition Binding Experiment

A mB7-1 hIgG1 Fc fusion construct was cloned which used the same erythropoietin (EPO) leader, mB7-1 ecto domain boundaries and linker sequence as the original mIgG2a construct described above. This construct was transiently expressed in HEK 293 cells and purified as described above for the other Fc fusion proteins used. For the completion experiment, HEK 293 suspension cells were transiently transfected with wild-type mPD-L1 mCherry. Three days post transfection transfected cells were counted and diluted to $1\times10^6$ cells/mL. B7-1 hIgG1 fusion protein was added to 100,000 transfected cells at a final concentration of 5 nM dimer, in either the absence or presence of increasing concentrations of PD-1 mIgG2a protein (0.01-250 nM dimer). Parallel experiments were carried out in which purified mIgG2a isotype control was titrated at equivalent molar concentrations. Protein binding was carried out at 22° C. shaking at 900 rpm on a 96-well plate shaker for 1 hour. After binding, plates were washed two times with 1×PBS with 0.2% BSA and anti-human (H+L) Alexa 488 labeled secondary antibody (Invitrogen) was added at 0.01 μg/μL (1 μg total) and incubated for 30 min. Cells were subsequently washed two more times with 1×PBS with 0.2% BSA. Samples were immediately analyzed by FACS and the data gated for the percent of mCherry positive cells (FL4-PD-L1 expression) that were also Alexa 488 positive (FL1-B7-1 Binding). Competition data was normalized to 5 nM B7-1 binding in the absence of mPD-1 and plotted as a function of log [mPD-1]. Average data from three independent experiments was fit using a one-site competition model equation $Y=\min+(\max-\min)/(1+10^{x-\log EC50})$.

Results

Mechanistic Dissection by Microarray Analysis

To generate selective PD-L1 reagents, the X-ray structure of the PD-1:PD-L1 complex was used as a framework to identify residues for mutagenesis—identifying 36 solvent exposed residues within the PD-L1 Ig variable domain (24). Each residue was changed to an alanine, arginine and glutamic acid to sample a range of side chain physicochemical characteristic properties. The cell microarray platform was used initially to challenge a set of wild-type and mutant PD-L1 constructs with PD-1 or B7-1 Fc-fusion protein. These experiments identified mutants that affected only PD-1 binding (D122A, Y123A, Y123R, K124A, K124D, R125A, R125D), only B7-1 binding (Y56A, Y56D, E72R, G119D, G120D) or both (L53R, G119R, A121R) (Table 1; provided in FIG. 10). However, consistent quantification of the PD-1/B7-1 binding proved difficult using the cell microarrays for the following reasons: (1) the lower affinity of B7-1 for PD-L1 reduced the signal to noise for these arrays compared to those challenged with PD-1; (2) the complete loss of binding was easily identified but modest reductions in binding were often more variable; (3) the inherent slide to slide variably associated with independently printed, transfected and treated slides added to signal to noise variations and made direct comparisons more difficult.

Validation by FACS Analysis

Figure 7A:
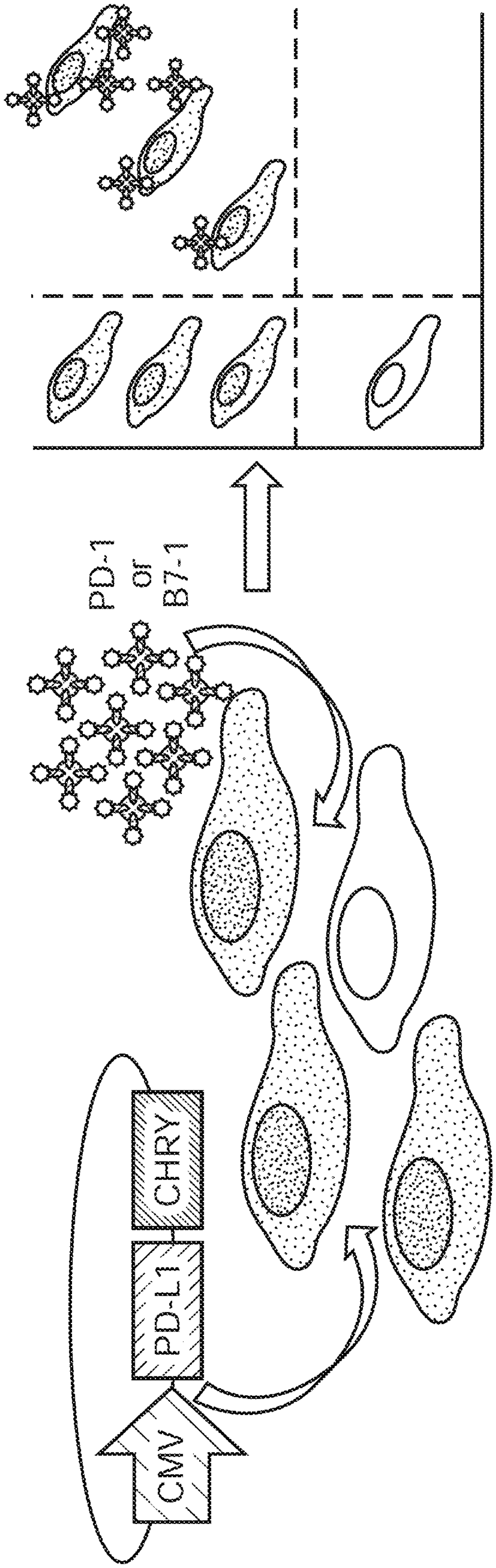
FIG. 7A-7C depict screening of PD-L1 mutants using a high-throughput microbead binding FACS assay (FIGS. 7A and 7B); and FACS microbead binding data for PD-L1 mutants (FIG. 7C).

To validate and more quantitatively evaluate the binding characteristics of PD-L1 mutants we implemented a high-throughput fluorescence activated cell sorting (FACS) assay, which enables the interrogation of 96 samples every ~15 minutes. This FACs platform affords an enhanced dynamic range compared to cell microarrays. Notably, the mode of query protein presentation is modified. While bivalent Ig-fusions, as used in the microarray platform, are effective for the identification of interactions with moderate affinities, weaker interactions might be missed. To support detection of the wide range of apparent affinities anticipated in analysis of the library of PD-L1 mutants the higher valency afforded by magnetic microbead capture and presentation was exploited (FIG. 7A). For example probing the microarray presenting PD-L1 required higher concentrations of B7-1 Fc than PD-1 Fc, resulting in greater background signal. The increase in dynamic range observed using the FACS microbeads assay is at least in part due to the reduction in background due to non-specific binding. This is likely for two reasons: (1) no secondary antibody is used in the microbead assay; (2) higher avidity means lower amounts of protein can be used to challenge the cells. The microbead assay has the added benefit of not requiring any wash steps, which minimizes loss of bound sample and makes the assay a much more direct measure of protein binding. Additionally, for some lower affinity interactions, such as that between B7-1 and PD-L1, achieving saturation with soluble B7-1 Fc is difficult in FACS assay, whereas B7-1 Fc conjugated microbeads resulted in significant improvement.

Figure 7B:
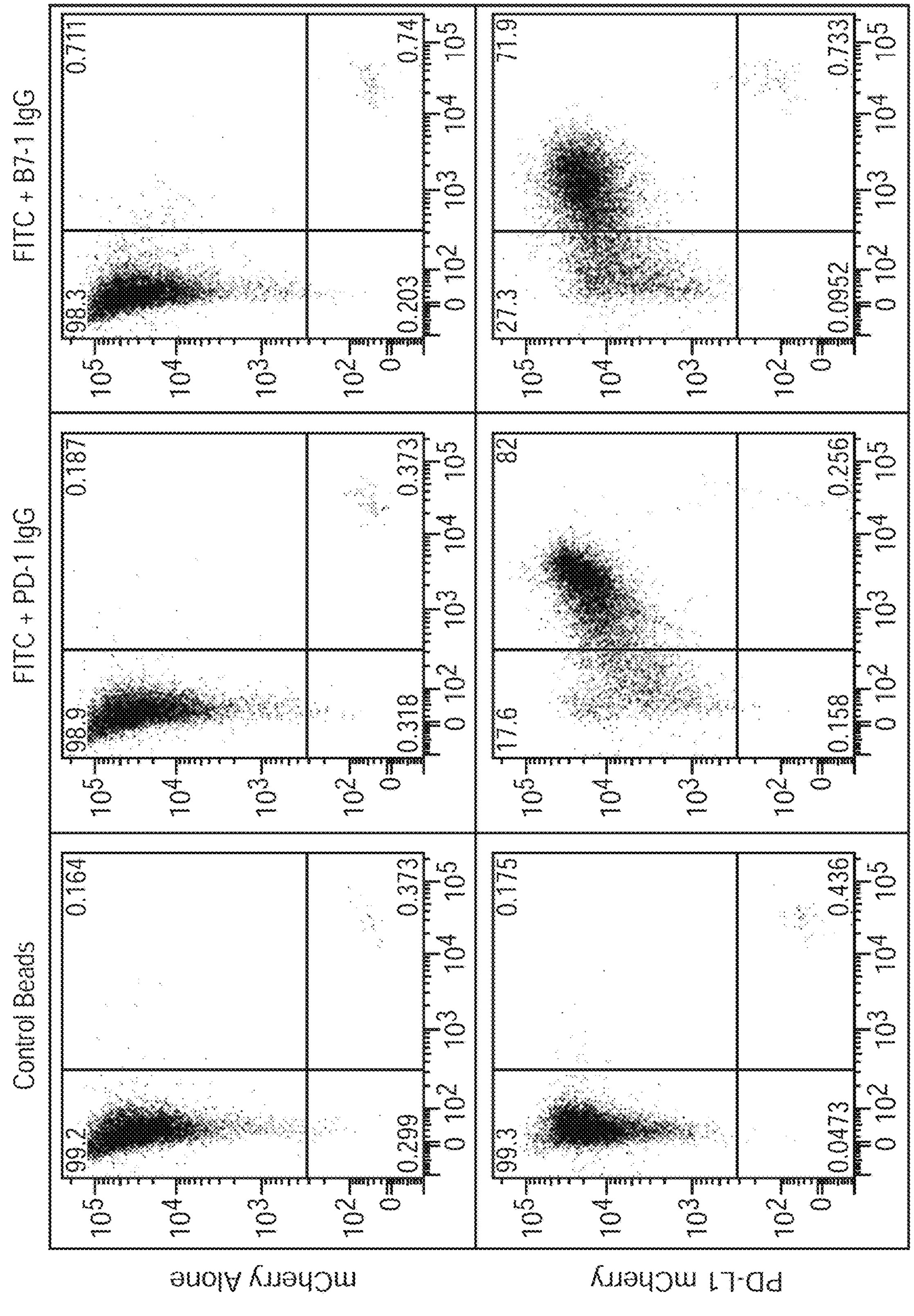

Briefly, HEK293 cell lines were individually transiently transfected with 55 different surface displayed mutant PD-L1-mCherry fusions. These cells were probed by flow cytometry for their ability to bind either FITC-loaded microbeads decorated with wild type PD-1 Ig-fusion or wild type B7-1 Ig-fusion proteins (FIG. 7B). Importantly, it is unlikely that these mutations caused global changes to the structure or stability of PD-L1, as the transient protein expression levels were similar to wild-type for all the mutants used for analysis. Also, fluorescence microscopy of the wild-type and mutant PD-L1 variants showed correct membrane localization of the C-terminal mCherry fusion protein suggesting the mutant proteins were being correctly folded, processed and inserted into the membrane. These studies resulted in the identification of PD-L1 mutants that either bound specifically to PD-1 (D49R, V54D, V54R, Y56A, Y56D, Y56R, Q66D, E72R, G119D, G120D) or B7-1 (D122A, Y123R, Y123A, K124A, K124D, K124R, R125A, R125D) or neither PD-1 or B7-1 (L53D, L53R, I115D, I116R, G119R, G120A, G120R, A121D, A121R, D122R). The affected residues were mapped onto the crystal structure of the PD-1:PD-L1 complex and shows the overlapping but distinct PD-L1 surfaces responsible for PD-1 and B7-1 binding. These results validated those obtained by the initial cell microarray experiments and provided a more quantitative assessment of PD-1 and B7-1 binding especially for those mutants that showed significantly reduced but not obliterated binding to PD-1 or B7-1 (Table 1 (FIG. 10), Table 2

(FIG. 11)). For example, in the cell microarray experiments levels of PD-1 and B7-1 binding to the V54D and Q66D PD-L1 mutants were similar whereas in the context of the microbead FACS assay these same two mutants showed wild-type levels of PD-1 binding and significantly reduced B7-1 binding.

Sequence alignment analysis of PD-L1 and PD-L2 also hints at the relative importance of these residues to PD-1 and B7-1 binding. In general the PD-1 binding specific residues are highly conserved in both PD-L1 and PD-L2, which is expected as both ligands bind to PD-1. However many of the identified B7-1-specific binding residues are only highly conserved in PD-L1 not PD-L2, which is logical as PD-L2 does not bind B7-1. This supports the data highlighting V54 and Y56 as especially critical for B7-1 binding.

Biological Activity of PD-L1 Mutants in a T-Cell Proliferation Assay

High-throughput transient transfection of HEK 293 cells in 24-well suspension tissue culture plates was optimized for the production of recombinant secreted Fc-fusion proteins in amounts consistent with screening. Utilizing this method, Fc-fusion proteins for a subset of the PD-L1 mutants with altered binding characteristics were purified. Following small-scale nickel purification of the PD-L1 proteins analytical gel filtration demonstrated that the selected mutants behaved similar to wild type protein. Prior to activity testing in T cell proliferation studies, the quality of each mutant protein was evaluated by FACS analysis for binding to HEK cells expressing surface-resident PD-1 or B7-1 (GFP fusions) to confirm that the soluble reagents behaved as expected (i.e. PD-L1_Y56A_Fc binds to cells expressing PD-1, but not to those expressing B7-1).

Figure 8A:
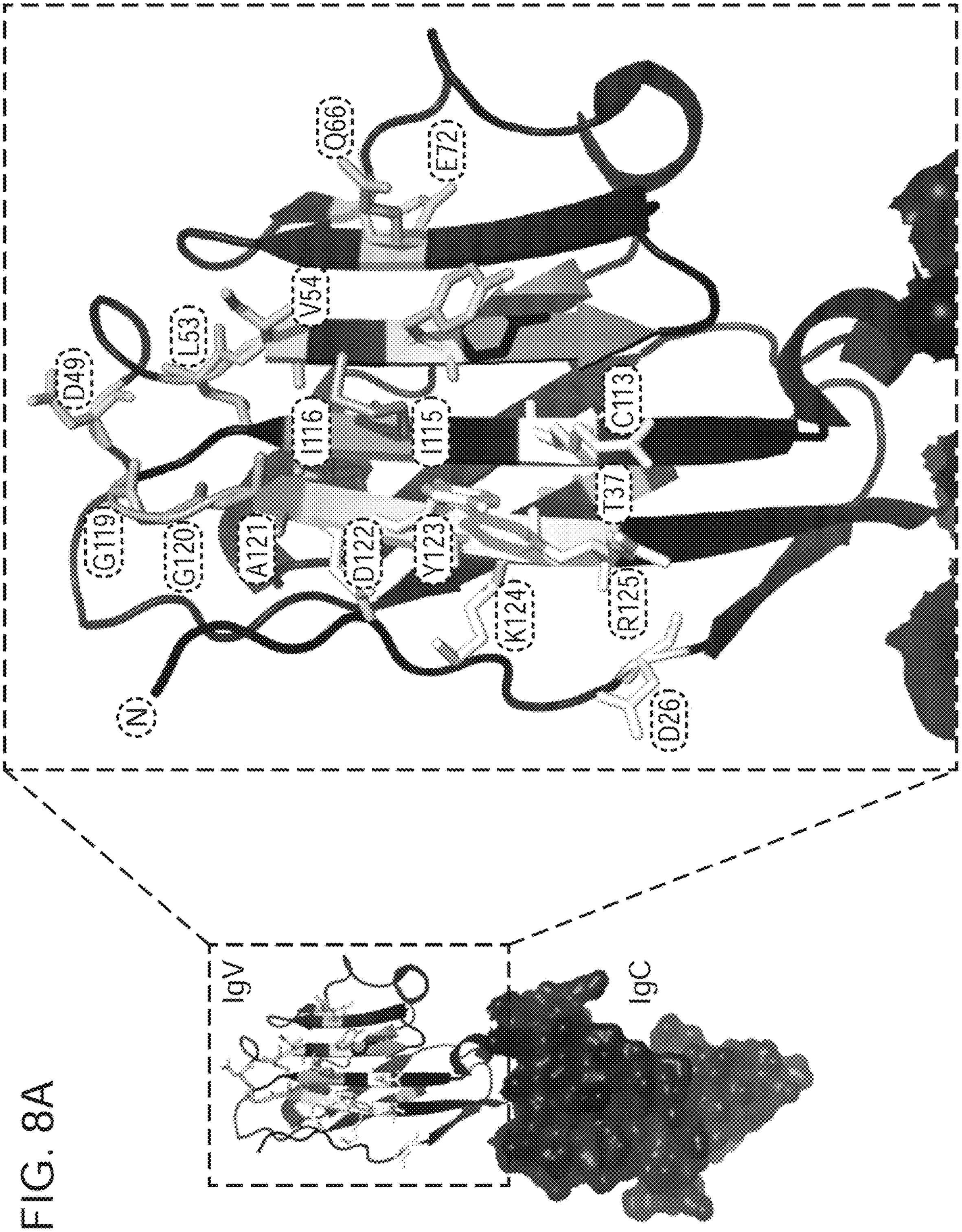
FIG. 8A-8D depict characterization of PD-L1 mutants with altered binding to PD-1 or B7-1.
Figure 8B:
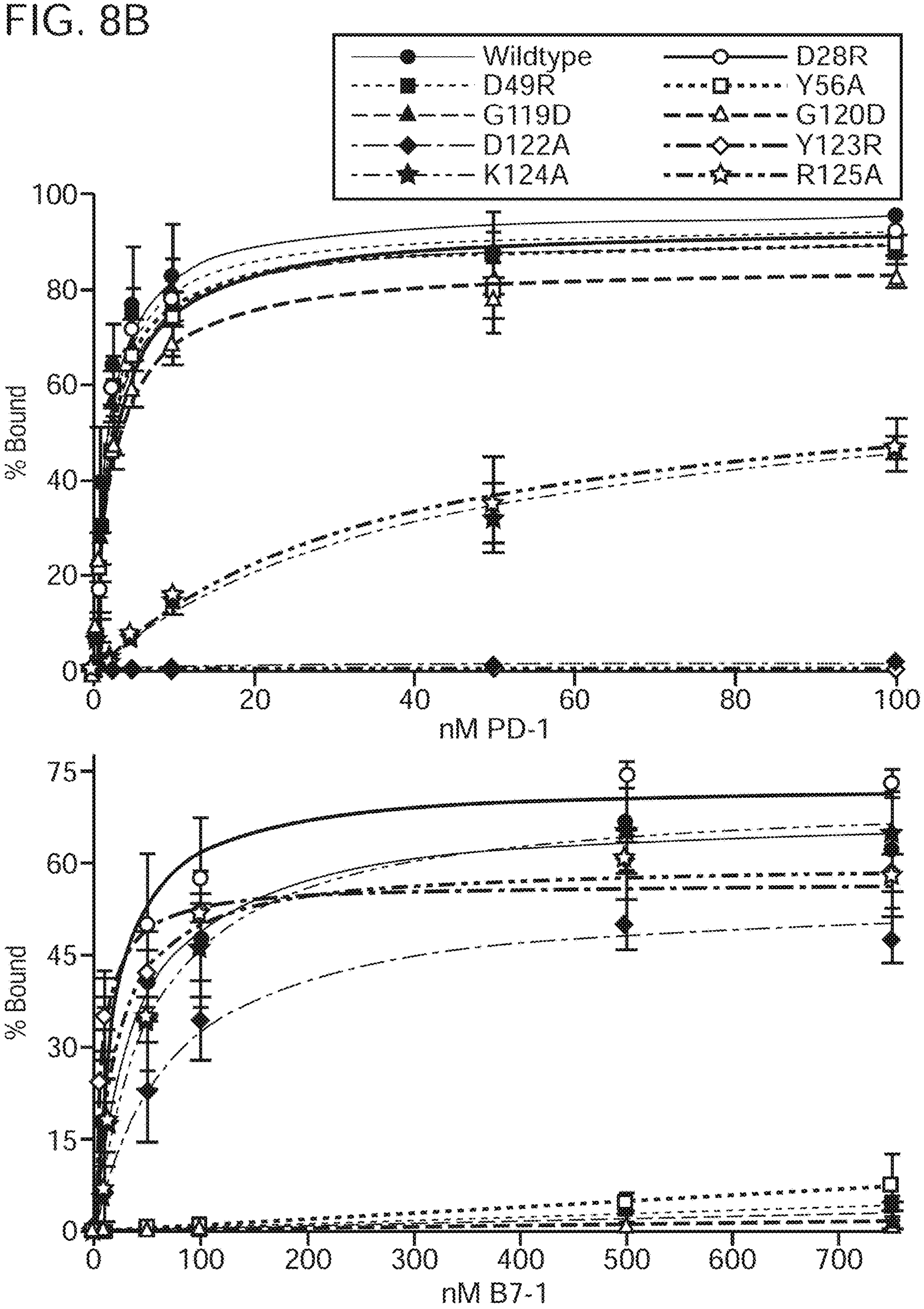
Figures 8C, 8D:
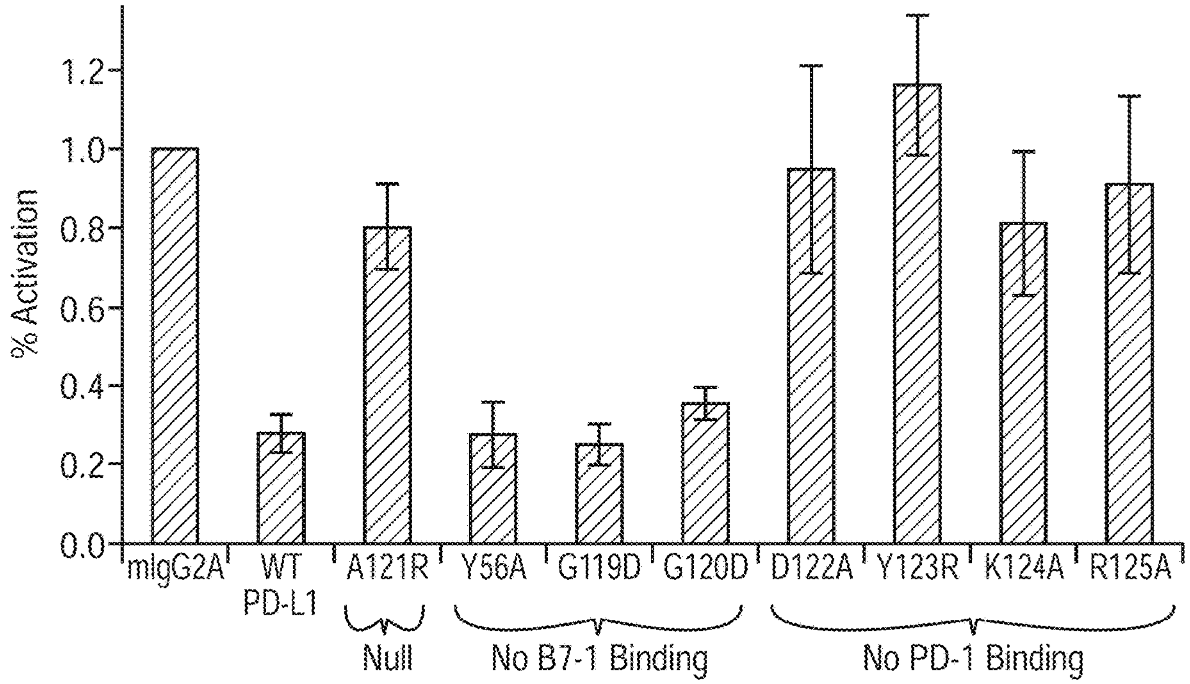

To characterize the biological activity of the functionally dissected PD-L1 mutants, an in vitro T-cell activation assay was used. This widely employed assay uses plate-bound anti-CD3 antibody to simulate activation of T-cells via the T-cell receptor. Anti-CD3 was co-plated in the presence of either IgG control, wild type PD-L1 or PD-L1 mutants and measured activation of CSFE labeled primary $CD4^+$ mouse T-cells. In the context of anti-CD3-mediated $CD4^+$ T-cell activation, wild type PD-L1 inhibits activation compared to isotype control (FIG. 8D) PD-L1 mutants with reduced levels of PD-1 binding showed a significantly reduced ability to inhibit T-cell activation. In contrast, PD-L1 mutants with reduced B7-1 activity elicited effects comparable to wild type PD-L1. These data suggest that under the in vitro experimental system employed, PD-L1-induced inhibition of $CD4^+$ T-cell activation occurs primarily via its interaction with PD-1. These data demonstrate the feasibility of generating mutants with specific biological activities that can aid in defining the distinct contributions of the PD-L1: PD-1 and PD-L1:B7-1 interactions to mammalian immunity.

PD-1 can Compete with B7-1 for Binding to PD-L1.

Figure 9A:
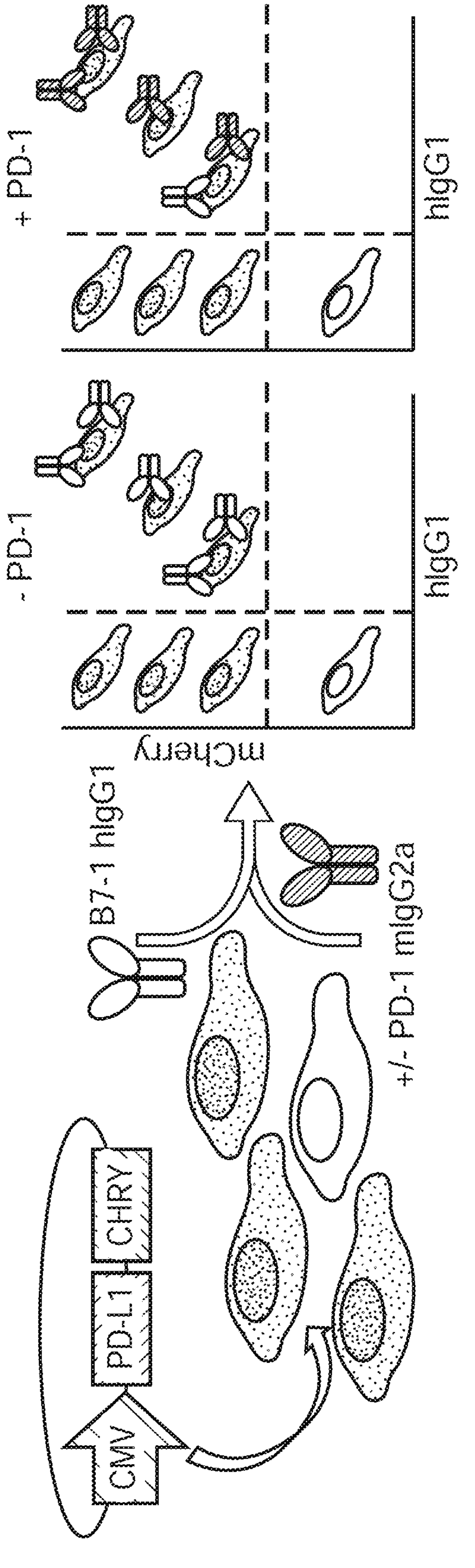
FIG. 9A-9B depicts PD-1 competing with B7-1 for binding to PD-L1.

The mutagenesis data showed that the binding surfaces on PD-L1 that bind PD-1 and B7-1 overlap but are distinct suggesting that PD-1 and B7-1 should compete for binding to PD-L1. This hypothesis was tested using a cell based FACS competition assay utilizing B7-1 and PD-1 Fc-fusion protein that we purified using two different Fc fusion isotypes. With these reagents, increasing concentrations of PD-1 (mIgG2a) were titrated, while the loss of B7-1 (hIgG1) that was bound to HEK cells expressing wild-type PD-L1 was selectively monitored using an anti-human Alexa 488 secondary antibody (FIG. 9A). The result shows that PD-1 binding efficiently displaces B7-1 from cells expressing PD-L1, which supports the finding, based on the PD-L1 mutagenesis, that the binding sites overlap.

Figure 7C:
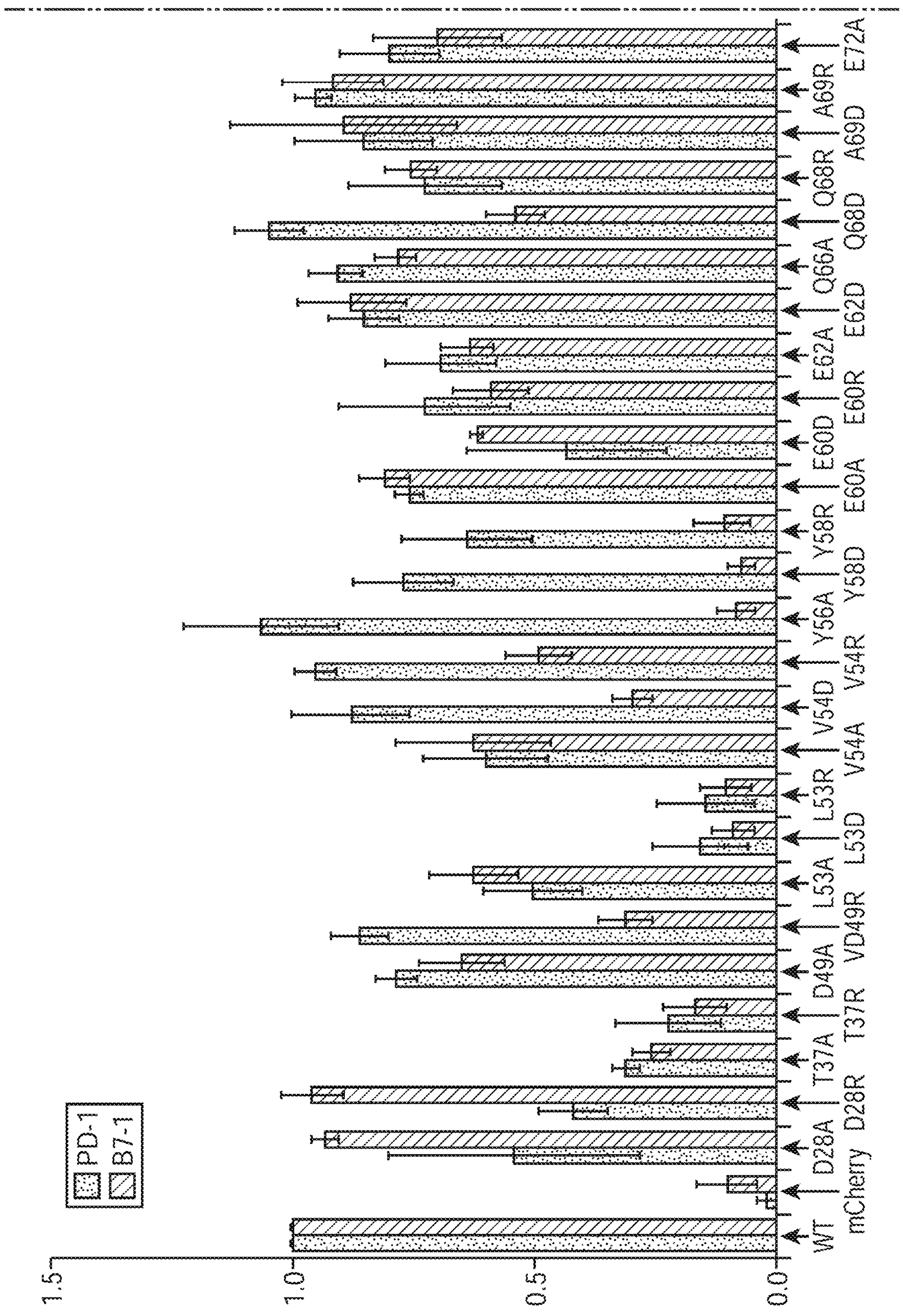
Figure 7C:
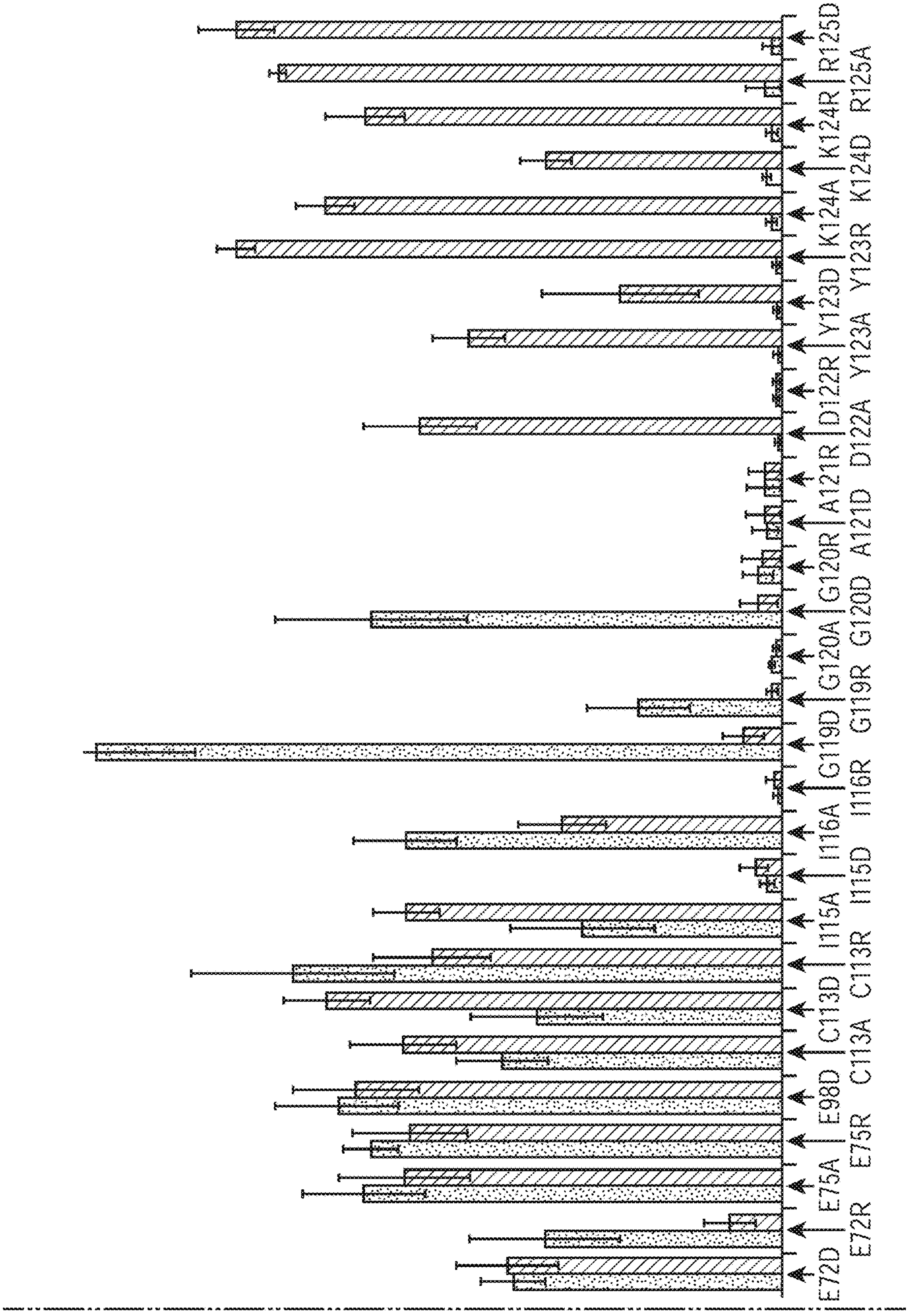

FIG. 7A-7C: Screening PD-L1 Mutants Using a High-Throughput Microbead Binding FACS Assay.

A) Schematic of the microbead FACS binding assay. B) Representative control microbead experiment. Cells expressing either mCherry alone (-control) or PD-L1 mCherry were challenged with microbeads conjugated with control Fc, PD-1 Fc or B7-1 Fc fusion protein. The FACS data was gated for all live cells and shows binding of both PD-1 and B7-1 coated microbeads (upper right quadrant) to cells expressing wild type PD-L1. C) FACS microbead binding data for a panel of 54 PD-L1 mutants. Data shows the fraction of mCherry positive cells (PD-L1 expressing) bound to microbeads coated in either PD-1 (Blue) or B7-1 (Red) with binding normalized to wild type. PD-1 and B7-1 binding was done in parallel triplicate experiments with error bars representing the standard deviation.

FIG. 8A-8D: Characterization of PD-L1 Mutants with Altered Binding to PD-1 or B7-1.

A) The crystal structure of the PD-1: PD-L1 complex (PDB: 3SBW) showing just the PD-L1 IgC and IgV domains. The IgV domain was enlarged and residue that when mutated resulted in altered binding are labeled and colored accordingly, green=PD-1 binding affected, red=B7-1 binding affected, gray=both PD-1 and B7-1 binding affected. B) Data obtained from FACS titration experiments in which cells expressing either wild type PD-L1 or a mutant were titrated with increasing concentrations of recombinant PD-1 or B7-1 Fc-fusion protein. Binding was detected using an anti-mouse Alexa 488 secondary antibody. Data points show the average of three independent experiments with error bars showing the standard deviation. Curves show the fit of the data to a single-site binding model. C) Table of $EC_{50}$ and $B_{max}$ values obtained from the FACS titration experiments in B. Stars denote those titrations for which binding was so low (baseline) that the data could not be fit. D) Data shows the fraction of CSFE labeled $CD4^+$ T-cells isolated from C57BL/6 mice activated after 4 days of stimulation with anti-CD3 in the presence of isotype control, wild type of mutant PD-L1 Fc-fusion protein. Activation was normalized to isotype control and represents three independent experiments.

Figure 9B:
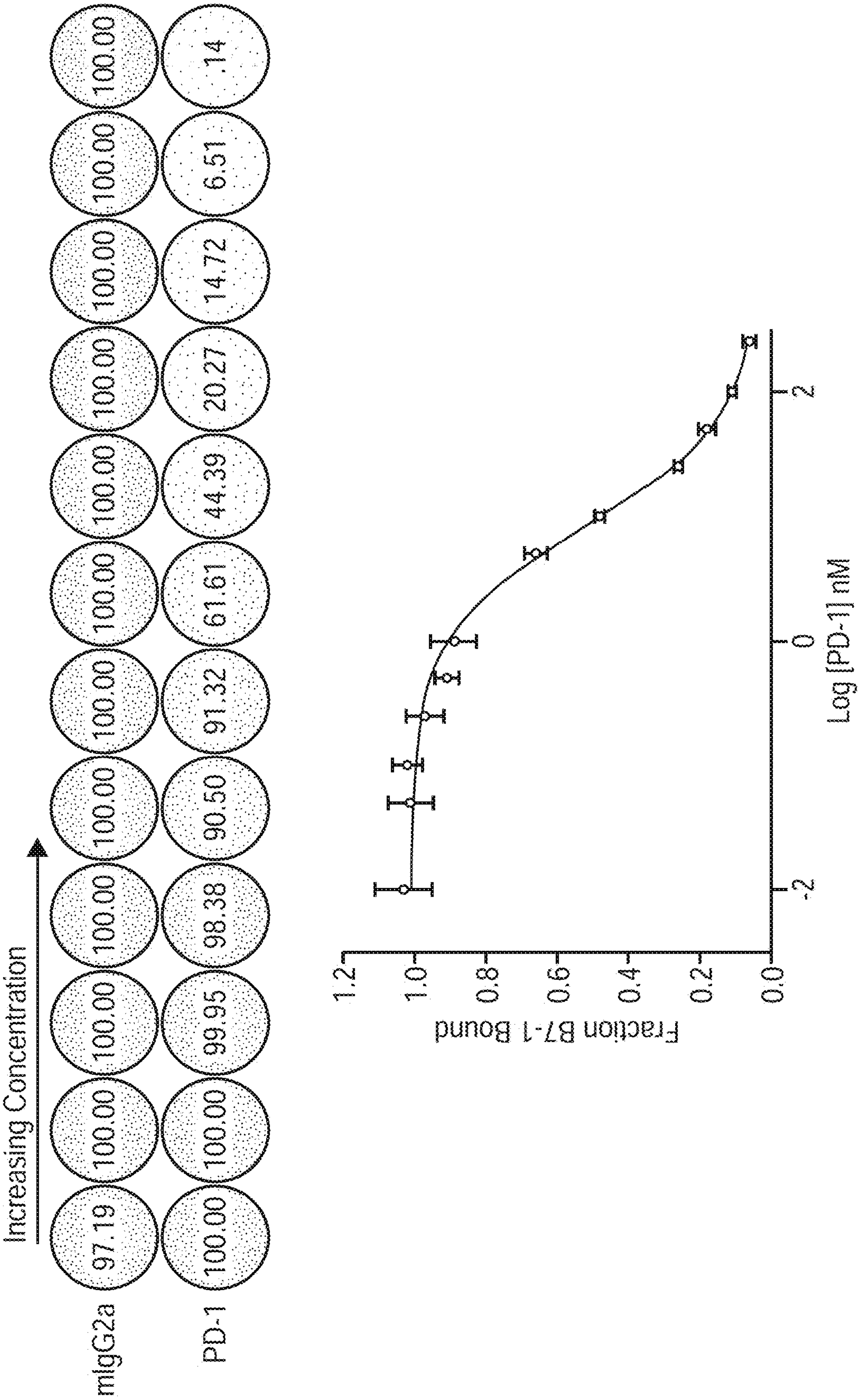

FIG. 9A-9B: PD-1 Competes with B7-1 for Binding to PD-L1.

A) Cartoon depiction of the competition assay. Briefly, HEK 293 cells transiently transfected with PD-L1 mCherry were incubated with mB7-1 hIgG1 protein in the absence or presence of increasing concentrations of mPD-1 mIgG2a. The amount of mB7-1 hIgG1 bound to cells was then monitored by FACS analysis using an anti-human Alexa 488 antibody. B) Heat map showing results from one representative experiment. In the presence of control mIgG2a no loss of mB7-1 hIgG1 binding was observed. The graph shows the average and standard deviation for data from three independent experiments. This data was fit using a one-site competition model equation in the software Prism and the calculated $EC_{50}$ was 8.3±1.5 nM.

Example 2: In Vivo Activity of a PD-L1/synTac

The NY8.3 TCR transgenic NOD model of type 1 diabetes (NOD 8.3) develops aggressive T cell autoimmunity directed against the pancreatic beta cell antigen $Igrp_{206-214}$ in the context of the MHC class I allele H-$2K^d$. NOD 8.3 mice have circulating transgenic (Igrp-specific) T cells at high frequency. A PD-L1/synTac bearing $Igrp_{206-214}$/H-$2K^d$ and PD-L1 (G119R variant) was administered to NOD 8.3 mice to determine the effect on the frequency of pathogenic transgenic T cells in the spleen. As shown in FIG. 12, a PD-L1(G119R)/synTac effects a dose dependent depletion of $Igrp_{206-214}$/H-$2K^{d}$ specific T cells, but not non-specific T cells.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A multimeric polypeptide comprising: a heterodimer comprising:

a) a first polypeptide comprising, in order from N-terminus to C-terminus:

i) a peptide epitope having a length of from 4 amino acids to 25 amino acids;

ii) a first major histocompatibility complex (MHC) polypeptide; and b) a second polypeptide comprising, in order from N-terminus to C-terminus:

i) a second MHC polypeptide; and ii) optionally an immunoglobulin (Ig) Fc polypeptide or a non-Ig scaffold, wherein the first and/or the second polypeptide comprises at least one immunomodulatory polypeptide, optionally, wherein the multimeric polypeptide comprises an immunoglobulin (Ig) Fc polypeptide or a non-Ig scaffold, wherein the at least one immunomodulatory polypeptide comprises an amino acid sequence having at least 95% amino acid sequence identity to the ectodomain of the PD-L1 amino acid sequence set forth in SEQ ID NO:71 or SEQ ID NO:72, wherein the variant PD-L1 immunomodulatory polypeptide comprises an amino acid substitution selected from D49R, Y56A, Y56D, Y56R, Q66D, E72R, G120D, Y123R, K124D, K124R, R125D, L53D, L53R, and E72D, and wherein the variant PD-L1 immunomodulatory polypeptide exhibits:

a) reduced binding affinity to a PD1 polypeptide having an amino acid sequence set forth in SEQ ID NO:56 or SEQ ID NO:57, compared to the binding affinity of the PD-L1 amino acid sequence as set forth in SEQ ID NO:1 or SEQ ID NO:2, for the PD1 polypeptide; and/or b) reduced binding affinity to a B7-1 polypeptide having an amino acid sequence set forth in SEQ ID NO:58 or SEQ ID NO:59, compared to the binding affinity of the PD-L1 amino acid sequence as set forth in SEQ ID NO:1 or SEQ ID NO:2, for the B7-1 polypeptide.

2. The multimeric polypeptide of claim 1, wherein:

a) the first polypeptide comprises, in order from N-terminus to C-terminus:

i) the peptide epitope;

ii) the first MHC polypeptide; and iii) the immunomodulatory polypeptide; and b) the second polypeptide comprises, in order from N-terminus to C-terminus:

i) the second MHC polypeptide; and ii) the Ig Fc polypeptide; or c) the first polypeptide comprises, in order from N-terminus to C-terminus:

i) the peptide epitope; and ii) the first MHC polypeptide; and d) the second polypeptide comprises, in order from N-terminus to C-terminus:

i) the immunomodulatory polypeptide;

iii) the second MHC polypeptide; and ii) the Ig Fc polypeptide; or e) the first polypeptide comprises, in order from N-terminus to C-terminus:

i) the peptide epitope; and ii) the first MHC polypeptide; and f) the second polypeptide comprises, in order from N-terminus to C-terminus:

i) the second MHC polypeptide; and ii) the Ig Fc polypeptide; and iii) the immunomodulatory polypeptide; or g) the first polypeptide comprises, in order from N-terminus to C-terminus:

i) the peptide epitope; and ii) the first MHC polypeptide; and h) the second polypeptide comprises, in order from N-terminus to C-terminus:

i) the second MHC polypeptide; and ii) the immunomodulatory polypeptide; or i) the first polypeptide comprises, in order from N-terminus to C-terminus:

i) the peptide epitope; and ii) the first MHC polypeptide; and j) the second polypeptide comprises, in order from N-terminus to C-terminus:

i) the immunomodulatory polypeptide; and ii) the second MHC polypeptide; or k) the first polypeptide comprises, in order from N-terminus to C-terminus:

i) the peptide epitope;

ii) the first MHC polypeptide; and iii) the immunomodulatory polypeptide; and l) the second polypeptide comprises, in order from N-terminus to C-terminus:

i) the second MHC polypeptide.

3. The multimeric polypeptide of claim 1, wherein the non-Ig scaffold is an XTEN polypeptide, a transferrin polypeptide, an elastin-like polypeptide, a silk-like polypeptide, or a silk-elastin-like polypeptide.

4. The multimeric polypeptide of claim 1, wherein the first MHC polypeptide is a β2-microglobulin polypeptide; and wherein the second MHC polypeptide is an MHC class I heavy chain polypeptide.

5. The multimeric polypeptide of claim 1, wherein:

(a) the first MHC polypeptide is an MHC Class II alpha chain polypeptide; and wherein the second MHC polypeptide is an MHC class II beta chain polypeptide; or (b) the first MHC polypeptide is an MHC Class II beta chain polypeptide; and wherein the second MHC polypeptide is an MHC class II alpha chain polypeptide.

6. The multimeric polypeptide of claim 1, wherein the first polypeptide and the second polypeptide are non-covalently associated.

7. The multimeric polypeptide of claim 1, wherein the first polypeptide and the second polypeptide are covalently linked.

8. The multimeric polypeptide of claim 7, wherein the covalent linkage is via a disulfide bond.

9. The multimeric polypeptide of claim 1, comprising 2 or more variant PD-L1 immunomodulatory polypeptides.

10. The multimeric polypeptide of claim 9, wherein the 2 or more immunomodulatory polypeptides are in tandem.

11. The multimeric polypeptide of claim 1, wherein the peptide epitope is a self epitope.

12. A protein comprising a homodimer of two molecules of the multimeric polypeptide of claim 1, wherein each molecule comprises an Ig Fc polypeptide, and wherein the two molecules are disulfide linked to one another via the Ig Fc polypeptide present in the two molecules.

13. A composition comprising:

a) the multimeric polypeptide of claim 1; and b) a pharmaceutically acceptable excipient.

14. The multimeric polypeptide of claim 2, wherein each multimeric polypeptide comprises one or more independently selected linker peptides interposed between one or more components of the first polypeptide, and wherein each multimeric polypeptide comprises one or more independently selected linker peptides interposed between one or more components of the second polypeptide.

15. The multimeric polypeptide of claim 2, wherein c) the first polypeptide comprises, in order from N-terminus to C-terminus:

i) the epitope; and ii) the first MHC polypeptide; and d) the second polypeptide comprises, in order from N-terminus to C-terminus:

i) the immunomodulatory polypeptide;

iii) the second MHC polypeptide; and ii) the Ig Fc polypeptide, wherein the first MHC polypeptide is an MHC Class II beta chain polypeptide; and wherein the second MHC polypeptide is an MHC class II alpha chain polypeptide; or e) the first polypeptide comprises, in order from N-terminus to C-terminus:

i) the epitope; and ii) the first MHC polypeptide; and f) the second polypeptide comprises, in order from N-terminus to C-terminus:

i) the second MHC polypeptide; and ii) the Ig Fc polypeptide; and iii) the immunomodulatory polypeptide, wherein the first MHC polypeptide is an MHC Class II beta chain polypeptide; and wherein the second MHC polypeptide is an MHC class II alpha chain polypeptide.

16. A protein comprising a homodimer of two molecules of the multimeric polypeptide of claim 14, wherein each molecule comprises an Ig Fc polypeptide, and wherein the two molecules are disulfide linked to one another via the Ig Fc polypeptide present in the two molecules.

17. A composition comprising:

a) the protein of claim 12; and b) a pharmaceutically acceptable excipient.

18. A composition comprising:

a) the protein of claim 16; and b) a pharmaceutically acceptable excipient.

* * * * *